(12) United States Patent
MacLeod et al.

(10) Patent No.: US 6,221,600 B1
(45) Date of Patent: Apr. 24, 2001

(54) COMBINATORIAL OLIGONUCLEOTIDE PCR: A METHOD FOR RAPID, GLOBAL EXPRESSION ANALYSIS

(75) Inventors: Michael C. MacLeod; C. Marcelo Aldaz; Sara S. Gaddis, all of Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/414,847

(22) Filed: Oct. 8, 1999

(51) Int. Cl.⁷ .............................. C12Q 1/68; C12P 19/34; C07H 21/02; C07H 21/04
(52) U.S. Cl. .......................... 435/6; 435/91.2; 536/23.1; 536/24.3
(58) Field of Search ..................... 435/6, 91.2; 531/23.1, 531/24.3

(56) References Cited

U.S. PATENT DOCUMENTS

| | | | |
|---|---|---|---|
| 5,053,336 | * 10/1991 | Vanderlaan et al. | 435/240.27 |
| 5,290,677 | * 3/1994 | Robertson et al. | 435/5 |
| 5,521,084 | * 5/1996 | Kowalski et al. | 435/240.2 |
| 5,656,470 | * 8/1997 | Martinis et al. | 435/183 |
| 5,688,648 | * 11/1997 | Mathies et al. | 435/6 |
| 5,736,330 | * 4/1998 | Fulton | 435/6 |
| 5,767,288 | * 6/1998 | Rock et al. | 549/22 |
| 5,770,716 | * 6/1998 | Khan et al. | 536/23.1 |
| 5,804,380 | * 9/1998 | Harley et al. | 435/6 |
| 5,817,462 | * 10/1998 | Garini et al. | 435/6 |
| 5,837,836 | * 11/1998 | Friderici et al. | 536/23.1 |
| 5,843,773 | * 12/1998 | Shin et al. | 435/320.1 |
| 5,851,772 | * 12/1998 | Mirzabekov et al. | 435/6 |
| 5,853,992 | * 12/1998 | Glazer et al. | 435/6 |
| 5,866,330 | 2/1999 | Kinzler et al. | 436/6 |
| 5,871,697 | 2/1999 | Rothberg et al. | 422/68.1 |
| 5,874,215 | 2/1999 | Kuiper et al. | 435/6 |
| 5,945,290 | * 8/1999 | Cowsert | 435/6 |
| 6,002,817 | * 12/1999 | Kopelman et al. | 385/12 |
| 6,007,996 | * 12/1999 | McNamara et al. | 435/6 |

FOREIGN PATENT DOCUMENTS

| | | |
|---|---|---|
| 0 534 858 A1 | 9/1992 | (EP). |
| WO 98/08981 | 3/1998 | (WO). |

OTHER PUBLICATIONS

Arrand JR et al, "Molecular cloning of the complete Epstein– Barr virus genome as a set of overlapping restriction endonuclease fragments", Nucleic Acids Research, vol. 9, No. 13, Jul. 10, 1981, pp. 2999–3014.*

An G et al, "Organization and nucleotide sequence of a new ribosomal operon in *Escherichia coli* containing the genes for ribosomal protein S2 and elongation factor Ts", Nucleic Acids Research, vol. 9, No. 16, Aug. 25, 1981, pp. 4163–4172.*

Adams et al., "Rapid cDNA sequencing (expressed sequence tags) from a directionally cloned human infant brain cDNA library," *Nat Genet*, 4:373–80, 1993.

Bachem et al., "Visualization of differential gene expression using a novel method of RNA fingerprinting based on AFLP: analysis of gene expression during potato tuber development," *The Plant Journal*, 9:745–753, 1996.

Bertioli et al., "An analysis of differential display shows a strong bias towards high copy number mRNAs," *Nucleic Acids Res.*, 23:4520–3, 1995.

DeRisi et al., "Use of a cDNA microarray to analyse gene expression patterns in human cancer," *Nature Genetics*, 14:457–460, 1996.

Habu et al., "Amplified Restriction Fragment Length Polymorphism–based mRNA fingerprinting using a single restriction enzyme that recognizes a 4–bp sequence," *Biochemcial and Biophysical Research Communications*, 234:516–521, 1997.

Hedrick et al., "Sequence relationships between putative T–cell receptor polypeptides and immunoglobulins," *Nature*, 308:153–1588 1984.

Hsieh et al., E2F1–induced apoptosis requires DNA binding but not transactivation and isinhibited by the retinoblastoma protein through directinteraction, *Genes Dev.*, 11:1840–1852, 1997.

Ito et al., "Flourescent differential display: arbitrarily primed RT–PCR fingerprinting on an automated DNA sequencer," *FEBS Lett.*, 351:231–236, 1994.

Ivanova and Belyavsky, Identification of differentially expressed genes by restriction endonuclease–based gene expression fingerprinting, 23:2954–2958, 1995.

Liang and Pardee, "Differentail display of eukaryotic messenger RNA by means of the polymerase chain reaction," *Science*, 257:967–971, 1992.

(List continued on next page.)

*Primary Examiner*—John S. Brusca
*Assistant Examiner*—Stephen Siu
(74) *Attorney, Agent, or Firm*—Fulbright & Jaworski, LLP

(57) ABSTRACT

The present invention relates to a method for the detection of gene expression and analysis of both known and unknown genes. The invention is a highly sensitive, rapid and cost-effective means of monitoring gene expression, as well as for the analysis and quantitation of changes in gene expression for a defined set of genes and in response to a wide variety of events. It is an important feature of the present invention that no single molecular species of cDNA gives rise to more than one fragment in the collection of products which are subsequently amplified and representative of each expressed gene. This achievement is facilitated by immobilizing the cDNA prior to digesting and then digesting with sequentially with two frequently cutting enzymes. Linker oligomers are ligated to each cut site following the respective digestion. Primers, complementary to the oligomer sequence with an additional 3' variable sequence are used to amplify the fragments. Using an array of fragments theoretically facilitates the amplification of all of the possible messages in a given sample.

84 Claims, 16 Drawing Sheets

OTHER PUBLICATIONS

Figure 1:
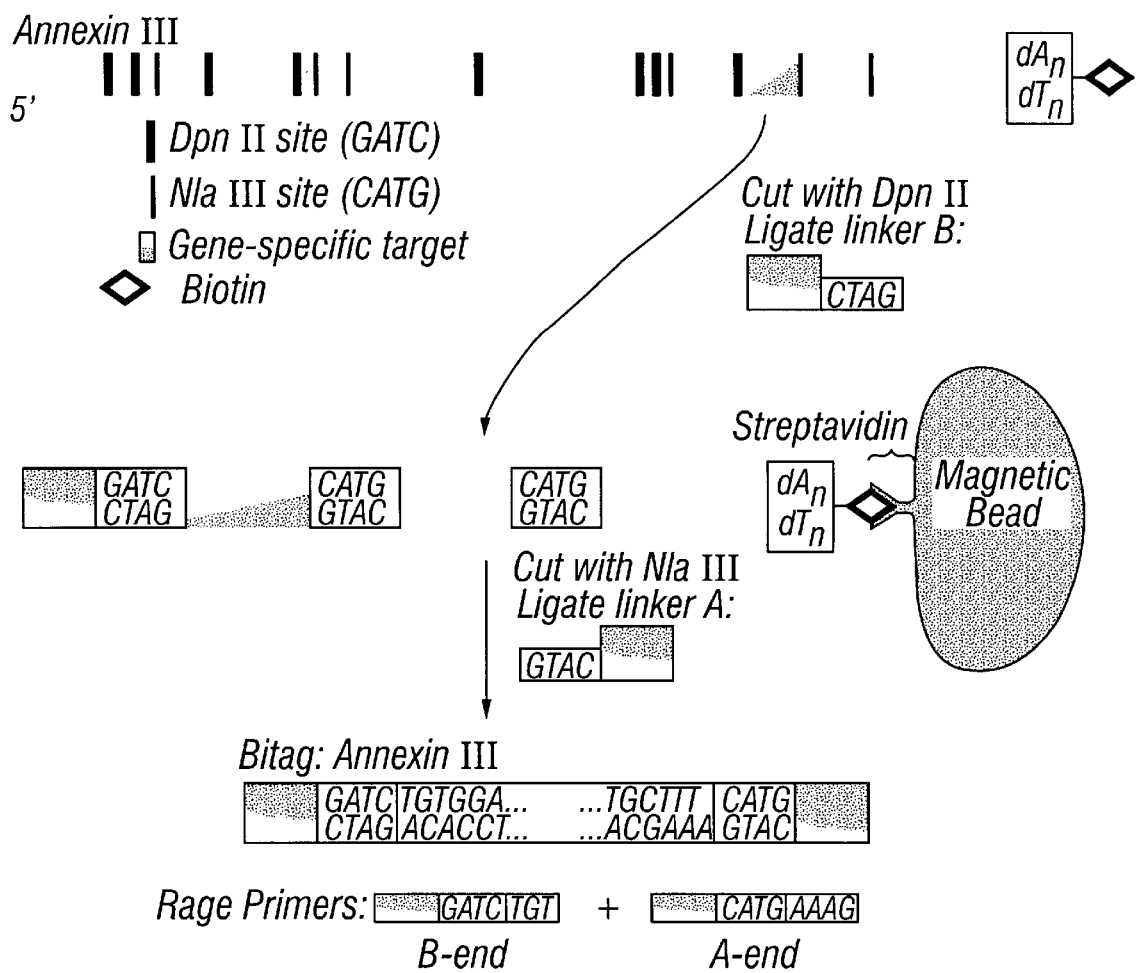

MacLeod et al., "Binding of the transcription factor, Sp1, to non–target sites in DNA modified by benzo[a]pyrene diol epoxide," *Carcinogenesis* 16:975–983, 1995.

MacLeod et al., "Interference of benzo[a]pyrene Diol epoxide–deoxyguanosine adductsin a GC box with binding of the transcrption factor Sp1," *Mol. Carcinogenesis* 16:44–52, 1996.

MacLeod, "A possible role in chemical carcinogenesis for epigenetic, heritable changes in gene expression," *Mol. Carcinogenesis* 15:241–250, 1996.

Money et al., "AFLP–based mRNA fingerprinting," *Nucleic Acids Research*, 24:2616–2617, 1996.

Okubo et al., "Large scale cDNA sequencing for analysis o quantitative and qualitative aspects of gene expression," *Nat Genet.*, 2:173–179, 1992.

Pierce et al, "Deregulated expression of E2F1 induces hyperplasia and cooperates with ras in skin tumor development," *Oncogene*, 16:1267–1276, 1998.

Pierce et al., "Increased E2F1 activity induces skin tumors in mice heterozygous and nullizygous for p53," *Proc. Nat'l Acad. Sci. USA*, 95:8858–8863, 1998.

Schena et al., "Quantitative monitoring of gene expression patterns with a complementary DNA microarray," *Science*, 270:467–470, 1995.

Shimkets et al., "Gene expression analysis by transcript profiling coupled to a gene databank query," *Nat Biotechnol.* 17:798–803, 1999.

Song and Osborn, "A method for examining expression of homologous genes in plant polyploids," *Plant Mol Biol.* 26:1065–1071, 1994.

Stone and Wharton, "Targeted RNA fingerprinting: the cloning of differentially–expressed cDNA fragments enriched for members of the zinc finger gene family," *Nucleic Acids Res.*, 22:2612–2618, 1994.

Velculescu et al, "Characterization of the yeast transcriptome," *Cell*, 88:243–251, 1997.

Velculescu et al., "Serial analysis of gene expression," *Science*, 270:484–487, 1995.

Vos et al., "AFLP: a new technique for DNA fingerprinting," *Nucleic Acids Research*, 23:4407–4414, 1995.

Wang and Feuerstein, "Direct Sequencing of DNA isolated from mRNA differential display," *Biotechniques*, 18:448–453, 1995.

Wang et al., "Rapid analysis of gene expression (RAGE) facilitates universal expression profiling," *Nucleic Acids Research*, 27(23):4609–4618, 1999.

Zhang et al., "Gene expression profiles in normal and cancer cells," *Science*, 276:1268–1272, 1997.

\* cited by examiner

```
1751  TAGGGCAGAC ATGCCTTGGT GCCGGTCACA CTCTACACGG ACTGAGGTGC
1801  CTGCTCAGGT GCTATGTCCC AAGAGCCATA AGGGGGTGGG AATTGGGGAG
1851  GGAGAAAGGG TAGTTCAAAG AGTCTGTCTT GAGATCTGAT TTTTTCCCCC
1901  TTTACCTAGC TGTGCCCCCT CTGGTTATTT ATTTCCCTAG TGCCAGGAGG
1951  GCACAGCAGG GGAGCCCTGA TTTTTAATAA ATCCGGAATT GTATTTATT
```

FIG. 8

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 1
gctgtctaga cg                                                              12

<210> SEQ ID NO 2
<211> LENGTH: 12
<212> TYPE: DNA
<213> ORGANISM: Artificial Sequence
<220> FEATURE:
```

```
<223> OTHER INFORMATION: Description of Artificial Sequence:  Synthetic
      Primer

<400> SEQUENCE: 2
cggtgatgca tc                                                              12
```

COMBINATORIAL OLIGONUCLEOTIDE PCR: A METHOD FOR RAPID, GLOBAL EXPRESSION ANALYSIS

BACKGROUND OF THE INVENTION

The government may own rights in the present invention pursuant to grant number P30ES07784-01 from NIEHS and grant number CA35581-12 from National Cancer Institute.

1. Field of the Invention

The present invention relates generally to detection of gene expression and analysis of both known and unknown genes. More particularly, it provides a method that can be used for global monitoring of gene expression, as well as for the analysis and quantitation of changes in gene expression for a defined set of genes and in response to a wide variety of events. The method is highly sensitive, rapid and cost-effective.

2. Description of Related Art

The degree of differentiation or physiological state of a cell, a tissue or an organism is characterized by a specific expression status, i.e., the degree of transcriptional activation of all genes or particular groups of genes. The molecular basis for numerous biological processes that result in a change in this state is the coordinated transcriptional activation or inactivation of particular genes or groups of genes in a cell, an organ or an organism. Characterization of this expression status is of key importance for answering many biological questions. Changes in gene expression in response to a stimulus, a developmental stage, a pathological state or a physiological state are important in determining the nature and mechanism of the change and in finding cures that could reverse a pathological condition. Patterns of gene expression are also expected to be useful in the diagnosis of pathological conditions, and for example, may provide a basis for the subclassification of functionally different subtypes of cancerous conditions.

Several methods that can analyze the expression status of genes are known in the art. Differential display RT-PCR™ (DDRT) is one method for analyzing differential gene expression in which subpopulations of complementary DNA (cDNA) are generated by reverse transcription of mRNA by using a cDNA primer with a 3' extension (preferably two bases). Random 10base primers are then used to generate PCR™ products of transcript-specific lengths. If the number of primer combinations used is large enough, it is statistically possible to detect almost all transcripts present in any given sample. PCR™ products obtained from two or more samples are then electrophoresed next to one another on a gel and differences in expression are directly compared. Differentially expressed bands can be cut out of the gel, reamnplified and cloned for filter analysis.

It is possible to enrich the PCR™ amplification products for a particular subgroup of all mRNA molecules, e.g., members of a particular gene family by using one primer which has a sequence specific for a gene family in combination with one of the 10 base random primers. This technique of DDRT is described by (Liang and Pardee, 1992; Liang et al., 1993; Bauer et al., 1993; Stone and Wharton, 1994; Wang and Feuerstein, 1995; WO 93/18176; and DE 43 17 414).

There are a number of disadvantages to the experimental design of DDRT. The differential banding patterns are often only poorly reproducible. Due to the design of the primers even the use of longer random primers of, erg., 20 bases in length does not satisfactorily solve the problem of reproducibility (Ito et al., 1994). In order to evaluate a significant portion of differentially expressed genes, a large number of primer combinations must be used and multiple replicates of each study must be done. The method often results in a high proportion of false positive results and rare transcripts cannot be detected in many DDRT studies (Bertioli et al., 1995.)

Due to the non-stringent PCR™ conditions and the use of only one arbitrary primer further analysis by sequencing is necessary to identify the gene. Sequencing of selected bands is problematic since the same primer often flanks DDRT products at both ends so that direct sequencing is not possible and an additional cloning step is necessary. Due to the use of short primers, a further reamplification step with primer molecules extended on the 5' side is necessary even if two different primers flank the product. Finally, due to the use of random primers, it is never quite possible to be sure that the primer combinations recognize all transcripts of a cell. This applies, even when using a high number of primers, to studies which are intended to detect the entirety of all transcripts as well as to studies which are directed towards the analysis of a subpopulation of transcripts such as a gene family (Bertioli et al., 1995).

A variant of DDRT, known as GeneCalling, has recently been described (Shimkets et al., 1999) which addresses some of these problems. In this method, multiple pairs of restriction endonucleases are used to prepare specific fragments of a cDNA population prior to amplification with pairs of universal primers. This improves the reproducibility of the measurements and the false positive rate, but the patterns are very complex and identification of individual transcripts requires the synthesis of a unique oligonucleotide for each gene to be tested. In addition, the quantitative data obtained are apparently significant only for changes above 4-fold (Shimkets et al. 1999) and only a weak correlation with other techniques is obtained. The ability of the technique to distinguish the gene-specific band from the complex background for any arbitrarily chosen gene has not been documented (Shimkets et al., 1999).

AFLP based niRNA fingerprinting further addresses some of the deficiencies of DDRT. AFLP allows for the systematic comparison of the differential expression of genes between RNA samples (Habu, 1997) The technique involves the endonuclease digestion of immobilized cDNA by a single restriction enzyme. The digested fragments are then ligated with a linker specific for the restriction cut site. The tailed fragments are subsequently amplified by PCR™ employing primers complementary to the linkers added to the digest with the addition of variable nucleotides at the 3' end of the primers. The products of the amplification are visualized by PAGE and banding patterns compared to reveal differences in RNA transcription patterns between samples. Although AFPTP based RNA fingerprinting provides a indication of the RNA message present in a given sample, it fails to restrict the potential number of signals produced by each individual RNA strand. With this technique, each RNA strand may potentially produce multiple fragments and therefore multiple signals upon amplification. This failure to restrict the number of signals from each message complicates the results that must be evaluated.

Song and Osborn, 1994, describe a method for examining the expression of homologous genes in plant polyploids in which the techniques of RT-PCR™ and RFLP (restriction fragment length polymorphism) analysis are combined with one another. In this method a cDNA is produced from RNA by reverse transcription, then amplified by using two gene-specific primers. The amplification products are transcript-specifically shortened by endonuclease cleavage, separated by electrophoresis according to their length, cloned, and then analyzed by sequencing. This method has the disadvantage of low sensitivity, as a cloning step is necessary to characterize the expression products. A further disadvantage of this method is that gene specific sequence information must be available on at least two regions within the analyzed genes in order to design suitable primers.

In principle, gene expression data for a particular biological sample could be obtained by large-scale sequencing of a cDNA library. The role of sequencing cDNA, generated by reverse transcription from mRNA, has been debated for its value in the human genome project. Proponents of genomic sequencing have argued the difficulty of finding every mRNA expressed in all tissues, cell types, and developmental stages. It is also believed that cDNA libraries do not provide all sequences corresponding to structural and regulatory polypeptides (Putney et al., 1983). In addition, libraries of cDNA may to be dominated by repetitive elements, mnitochondrial genes, ribosomal RNA genes, and other nuclear genes comprising common or housekeeping sequences. While some mRNAs are abundant, others are rare, resulting in cellular quantities of mRNA from various genes that can vary by several orders of magnitude. Therefore, sequencing of transcribed regions of the genome using cDNA libraries has been considered unsatisfactory.

Techniques based on cDNA subtraction or differential display can be used to compare gene expression patterns between two cell types (Hedrick et al., 1984; Liang and Pardee, 1992), but provide only a partial analysis, with no quantitative information regarding the abundance of messenger RNA. Expressed sequence tags (EST) have been valuable for gene discovery (Adams et al., 1993; Okubo et al., 1992), but like Northern blotting, RNase protection, and reverse transcriptase-polymerase chain reaction (RT-PCR™) analysis (Alwine et al., 1977; Zinn et al, 1983; Veres et al., 1987) the approach only evaluates a limited number of genes at a time.

Two major strategies for global gene expression analysis have recently become available. Serial analysis of gene expression (SAGE) (U.S. Pat. No. 5,866,330, Kinzler, et al., 1995) is based on the use of short (ie. 9–10 base pair) nucleotide sequence tags that identify a defined position in an mRNA and are used to ascertain the identity of the corresponding transcript and gene. The cDNA tags are generated from mRNA samples, randomly paired, concatenated, cloned, and sequenced. While this method allows the analysis of a large number of transcripts, the identification of individual genes requires sequencing of tens of thousands of tags for comparison of even a small number of samples. Although SAGE provides a comprehensive picture of gene expression, it cannot be specifically directed at a small subset of the transcriptome (Zhang et al., 1997; Velculescu et al., 1995). Data on the most abundant transcripts is the easiest and fastest to obtain, while about a megabase of sequencing data is needed for confident analysis of low abundance transcripts.

The second method utilizes hybridization of cDNAs or mRNAs to microarrays containing hundreds or thousands of individual cDNA fragments or oligonucleotides specific for particular genes or ESTs. The matrix for hybridization is either a DNA chip, a slide or a membrane. This method can be used to direct a search towards specific subsets of genes, but cannot be used to identify novel genes. In addition, arrays are expensive to produce (DeRisi et al., 1996; Schena et al., 1995). For those methods using cDNA arrays, a library of individually cloned DNA fragments must be maintained with at least one clone for each gene to be analyzed Because much of the expense of utilizing microarrays lies in maintaining the fragment libraries and programming equipment to construct the microarray, it is only cost-efficient to produce large numbers of identical arrays. These two techniques lack the flexibility to easily change the subset of the transcriptome being analyzed or to focus on smaller subsets of genes for more detailed analyses.

As described above, current techniques for analysis of gene expression either monitor one gene at a time, are designed for the simultaneous and therefore more laborious analysis of thousands of genes or do not adequately restrict the signal to message ratio. There is a need for improved methods which encompass both rapid, detailed analysis of global expression patterns of genes as well as expression patterns of defined sets of genes for the investigation of a variety of biological applications. This is particularly true for establishing changes in the pattern of gene expression in the same cell type, for example, in different developmental stages, under different physiologic or pathologic conditions, when treated with different pharmaceuticals, mutagens, carcinogens, etc. Identification of differential patterns of expression has several utilities, including the identification of appropriate therapeutic targets, candidate genes for gene therapy (including gene replacement), tissue typing, forensic identification, mapping locations of disease-associated genes, and for the identification of diagnostic and prognostic indicator genes.

The object of the present invention is to provide a method for gene expression analysis which exceeds the capabilities of the state of the art. The optimal method should be rapid and cost-effective, allow easily reproducible and quantitative results, have an adequate sensitivity in order to detect and quantify rare transcripts, and enable identification of amplification products by techniques that do not require an additional cloning or sequencing step. The technique should allow flexibility to analyze either a subset or the complete transcxiptome, and should be useful for both gene discovery and to analyze previously identified genes.

SUMMARY OF THE INVENTION

In the present disclosure, a method has been developed which allows for the determination of changes in gene expression in multiple genes, known and unknown, in a rapid, quantitative and cost-effective fashion. This method has the capability for detecting the frequency distribution of all polyadenylated mRNAs in a sample at any selected time. The invention reduces the complexity of analysis by ensuring that only a single unique fragment is derived from each molecular species of polyadenylated mRNA. Either the entire genome or a subset can be analyzed, and a single set of reagents and reaction conditions is sufficient for analysis of the complete genome. The technique allows for multiple samples to be analyzed simultaneously. The results generated from this invention are quantitative and proportional to the level of expression of the particular gene.

A unique feature of this method that distinguishes it from all DDRT methods is that a one-to-one correspondence exists between each molecular species of polyadenylated RNA and a PCR™-product of a particular length derived with a particular pair of PCR™ primers. Knowledge of a gene sequence therefore can be used to pick the correct pair of primers to use for amplification and to predict the length of the corresponding product. This feature is also advantageous when combinatorially surveying the entire (genome) transcriptome. The length of the amplimer products, along with the information on the primers used, can be plugged into the database to identify the differentially expressed genes.

One embodiment of the invention involves a method comprising obtaining an DNA molecule, which includes an anchorable moiety, and cleaving the DNA molecule with a first restriction endonuclease. A linker is then ligated to the cut end of the DNA fragment, and the fragment is immobilized to an anchor via the anchorable moiety. The immobilized fragment is then digested with a second restriction enzyme, cleaving it from the anchor. A second linker is subsequently added to the second digest site, and the fragment is then amplified. The order of restriction digests may be reversed to isolate those fragments in which the order of restriction sites is reversed, thereby representing a more complete share of the DNA present in a sample. It is envisioned that the DNA molecule may be immobilized at its 5' end or at its 3' end.

It is envisioned that this technique may be used in the detection of specific DNA, be it genomic, non-genomic or synthetic as well as cDNA, reversed transcribed from RNA.

Where the DNA is cDNA, the immobilization of the DNA may take place prior to the reverse transcription of mRNA to cDNA, or the molecule may be subsequently immobilized.

In another embodiment, the immobilization of the DNA may take place subsequent to the initial restriction digestion. In a further embodiment, the immobilization of the DNA may take place subsequent to the initial restriction digestion and linker ligation.

It is envisioned that the immobilization will occur at the anchorable moiety via a means of adhering. The means of adhering may facilitate either a covalent or non-covalent interaction. It is envisioned that the anchorable moiety may be located at either the 5' or 3' end of the DNA. The anchorable moiety may be a ligand, for example biotin or an antibody. Where the anchorable moiety includes a ligand, it is envisioned that this ligand is the means through which the DNA is immobilized to a substrate. Where the ligand is biotin, the biotin may be attached to streptavidin.

In a further embodiment of the invention, mRNA is reverse transcribed to cDNA with an oligo-dT primer. It is further envisioned that reverse transcription may also be initiated at a random hexamer. The oligo-dT primer may be attached to a ligand, for example biotin or an antibody. Where the oligo-dT includes a ligand, it is envisioned that this ligand is the means through which the cDNA is immobilized to a substrate. Where the ligand is biotin, the biotin may be attached to streptavidin.

In another embodiment of the invention, it is envisioned that the amplification of the fragment is initiated at primers of a sequence complementary to the first and second linkers respectively. It is further envisioned that this amplification reaction may include: a first amplification primer in which the 5' sequence of the primer is complementary to the first linker sequence and the 3' sequence comprises a specificity region; a second amplification primer, wherein the 5' sequence of said primer is complementary to said second linker sequence and the 3' sequence comprises a specificity region. This method may be further modified to consist of an array of combinations of alternate amplification primers such that the specificity region facilitates the amplification of a substantial percentage of the different sequences within a sample. Such an array may be simplified by carrying it out in a multi-well plate.

Amplification of the samples may be further enhanced by pre-amplification with primer pairs complementary to the first and second linker sequences, respectively, prior to amplification with said amplification primers. Further, a partial nucleotide sequence identification of the amplified products may be facilitated by the sequence of the primers used for the amplification. It is envisioned that such identification may be carried out with the aid of a computer program. It is further envisioned that the identification of the amplified DNA may be based on length.

It is envisioned that the 3' specificity region of the first and second primers may be 3 nucleotides long. It is further envisioned that such 3' regions may be either 4,5,6,7 or even 8 base pairs long.

Amplification of the fragments may occur through either the polymerase chain reaction, nucleic acid sequence based amplification, transcription mediated amplification, strand displacement amplification, ligase chain reaction or any other method recognized by a person of ordinary skill in the art to be useful in the amplification of nucleic acid.

It is envisioned that the one or both of the restriction enzymes used to digest the immobilized DNA molecule have either a four, five, six, seven or eight base recognition site. In a preferred embodiment of the invention, the one or both of the restriction enzymes will have a four base pair recognition site. It is envisioned that such restriction enzymes might include but are not limited to: NlaIII, DpnII, Sau3AI, Hsp92II, MboI, NdeII, Bsp143I, Tsp509 I, HhaI, HinP1I, HpaII, MspI, TaqalphaI, MaeII or K2091.

In an additional embodiment of the invention, the amplified product will incorporate a means of detection such that the amplification may be detected and quantified. In a preferred embodiment the means of detection will be a label incorporated into one of the primers used to amplify the fragment or alternatively as a labeled nucleotide incorporated during amplification. It is envisioned that the label may be used to partially identify the sequence information of the amplified product.

It is envisioned that this label could include a chromophore, a flurophore, an affinity label or a dye. In a further embodiment of the invention a primer would contain an amino moiety and to which a flurophore could be covalently attached by the reaction of a succinimido ester of the flurophore to the 5' amino-modified primer. In this embodiment, the flurophore could include but is not limited to: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In another additional embodiment, the means of detection may be a nucleotide label incorporated into the product during amplification. It is envisioned that the label attached to the nucleotide could be biotin, DIG, AP, HRP, a fluorescent compound as mentioned in the paragraph above, DNP, or AMCA, to which any of these labels could be attached to after amplification.

While the products of amplification may be labeled for analysis, it is envisioned that other means of analysis may also be employed. The amplification products may be analyzed by polyacrylamide gel electrophoresis, capillary gel electrophoresis, mass spectrophotometry, energy transfer, real time PCR™, or the Biostar or Luminex technologies.

Analysis may occur to quantify the products. Such quantification may be facilitated by measuring the ratio of each amplified product to a co-amplified reference-gene, or by measuring the ratio of each amplified product to a panel of co-amplified reference-genes.

Analysis of the amplification products may be performed in a multi-well plate, on a gel, on a membrane, or on a solid matrix. Where the analysis takes place on a solid substrate, it is envisioned that the solid substrate may be a DNA chip.

In a preferred embodiment of the invention, the method will be used to compare DNA in a normal cell to DNA in a different cell or tissue, or alternatively to an altered, modified or treated cell. It is envisioned that such alterations, modifications or treatments could include a cell or tissue treated with a pharmaceutical compound, a cell or tissue treated with a teratogenic compound, a cell or tissue treated with a carcinogenic compound, a cell or tissue treated with a toxic compound, a cell or tissue treated with a biological response modifier, a cell or tissue treated with a hormone, a hormone agonist or a hormone antagonist, a cell or tissue treated with a cytokine, a cell or tissue treated with a growth factor, a cell or tissue treated with the ligand of a known biological receptor, a cell or tissue type obtained from different species, a cell or tissue at different stages of development, or a cell or tissue cultured in vitro under different conditions. It is further envisioned that the method could be used to compare a cell or tissue from two organisms of the same species. Such organisms could further have a known genetic difference. The method may also be used to compare gene expression in a normal cell with gene expression in a diseased cell. It is envisioned that such diseases could include diseases that are infectious, metabolic, genetic, congenital, adaptational, constitutional, drug-related or hereditary.

In an additional embodiment of the invention, the means necessary for performing the method of this invention are included in a kit for detection of gene expression. In a preferred embodiment, such a kit would consist essentially of a first restriction enzyme, a second restriction enzyme, a first, ligatable oligonucleotide tag, a second, ligatable oligonucleotide tag, a first amplification primer, wherein the 5' sequence of said primer is complementary to said first linker sequence and the 3' sequence comprises a specificity region, a second amplification primer, wherein the 5' sequence of said primer is complementary to said second linker sequence and the 3' sequence comprises a specificity region, and software capable of analyzing data generated from use of the kit. It is envisioned that the kit may contain as the first primer, a primer including the sequence GCTGTCIAGACG (SEQ ID NO: 1). It is further envisioned that the kit may contain as the second primer a primer including the sequence CGGTGATGCATC (SEQ ID NO:2). The kit may also include restriction enzymes of a type as previously described.

It is contemplated that the method described herein and suitable modifications thereof will be used for determining global changes in gene expression patterns in a cell or tissue at any selected time. Appropriate examples include: changes in gene expression patterns due to developmental changes; changes in gene expression patterns due to cancerous transformation in cells; changes in gene expression patterns due to treatment of the cell or organism with a pharmaceutical compound; changes in gene expression patterns due to treatment of the cell or organism with a carcinogen. It is also contemplated that the method will be used for determining gene expression of a transcriptome at any selected time, for new gene discovery, and for diagnostic and/or prognostic purposes.

BRIEF DESCRIFIION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Preparation of genetag templates. The method is illustrated with the cDNA for annexin III.

FIG. 2A, FIG. 2B, FIG. 2C and FIG. 2D. Selective detection of expressed genes. A. COP primers specific for Brca1, Anx3 (annexin III), or an anonymous cDNA clone, 2C11B (U01139) were combined with B/A genetags prepared from murine keratinocytes and PCR amplification carried out for 27 cycles. PCR products were analyzed by polyacrylamide gel electrophoresis. Wedges above the lanes indicate increasing concentrations of template (0.15 to 1.2 ng for Anx3-specific reactions, 2 to 8 ng for Brca1- and 2C11B-specific reactions); -', no template controls; 'M', molecular size markers. B. The integrated intensities of the Anx3-specific amplimers in panel A were determined by densitometry, and are plotted as a function of template concentration. C. Anx3-specific COP reactions were carried out as described, but the number of PCR cycles was varied from 22 to 30. The natural logarithm of the integrated intensity is plotted as a function of the number of cycles. D. COP primers specific for HSPB1 (HSP27), RPS5 (ribosomal protein S5), or TRAF4 (MLN62 oncogene) were combined with A/B genetags prepared from normal human mammary epithelial cells, and PCR products were analyzed as in panel A. Amplimer intensities increased linearly with template concentration up to about 0.4 ng/reaction for HSP27 and S5, and up to at least 3.8 ng/reaction for MLN62.

Figure 3:
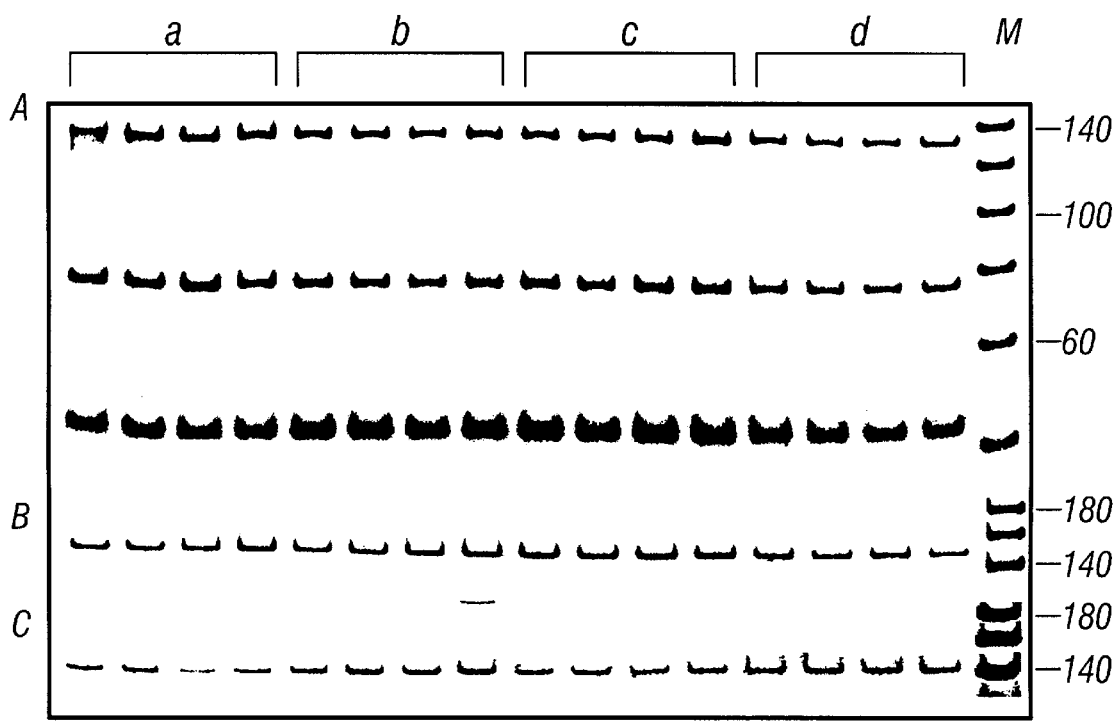

FIG. 3 Reproducibility of analyses. cDNA was prepared from normal human mammary epithelial cells, and 4 independent genetag templates (labeled a–d) were prepared. Quadruplicate PCR reactions were analyzed using primers specific for: A. CAPN4 (42 bp amplimer, Calpain); B. TRAF4 (151 bp amplimer, MLN62); or C. PSMD12 (146 bp amplimer, p55).

Figure 4:
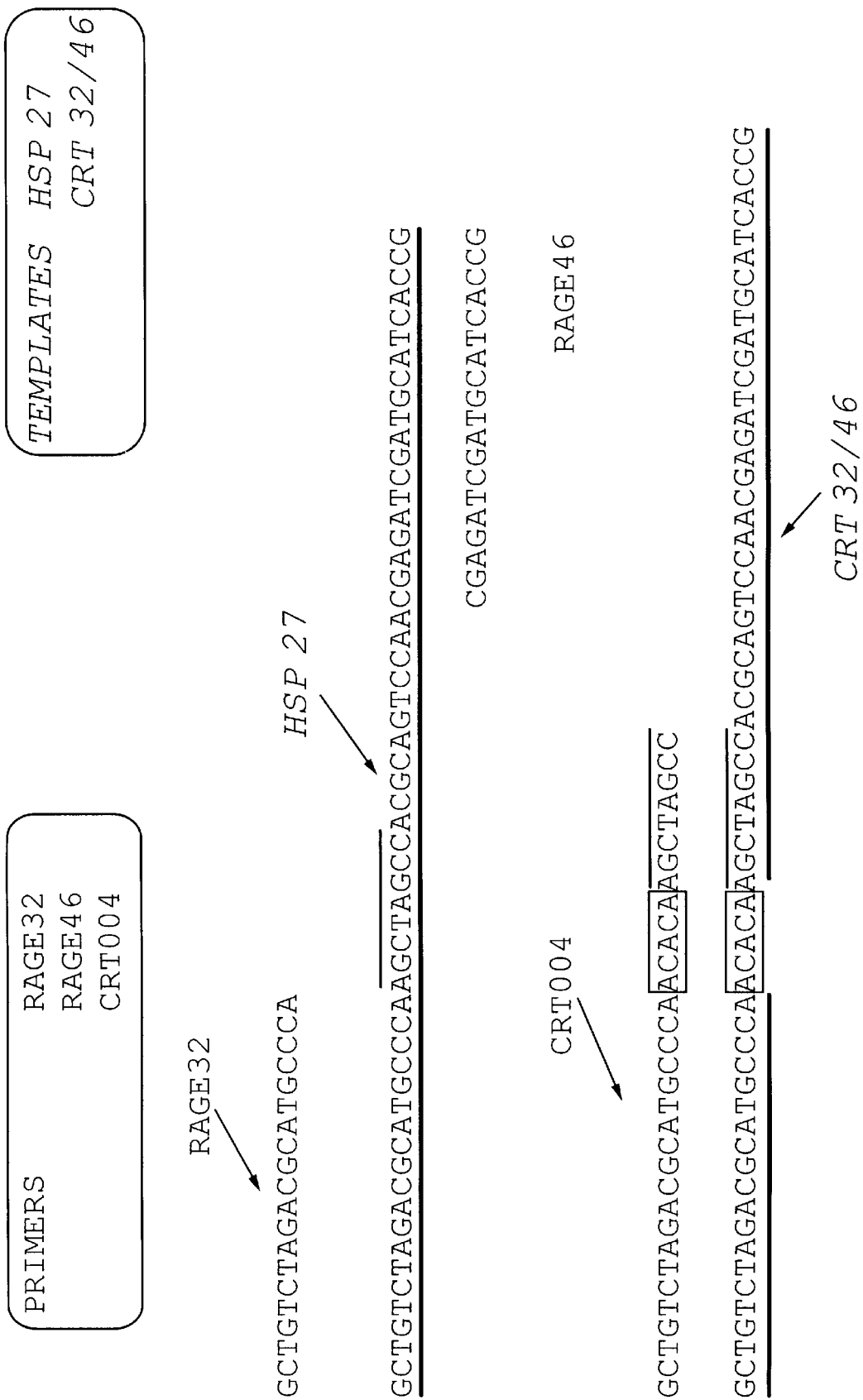

FIG. 4. Tactics for competitive RT-PCR™ with COP primers. The portion of the HSP27 cDNA sequence indicated with the heavy underline below can be amplified by the standard primers COP 32 and COP 46. Primer CRT004, containing the COP 32 sequence, a 5 bp insert (identified by the box), and the next 8 bp from HSP27 ("clamp" sequence, identified by overline) were synthesized. When CRT004 and COP 46 were used in a PCR™ reaction containing the HSP27 template, an amplimer identified as CRT32/46 was produced. As CRT32/46 contains all of the HSP27 sequences plus the 5 bp insert it can be used as a competitive template.

Figure 5:
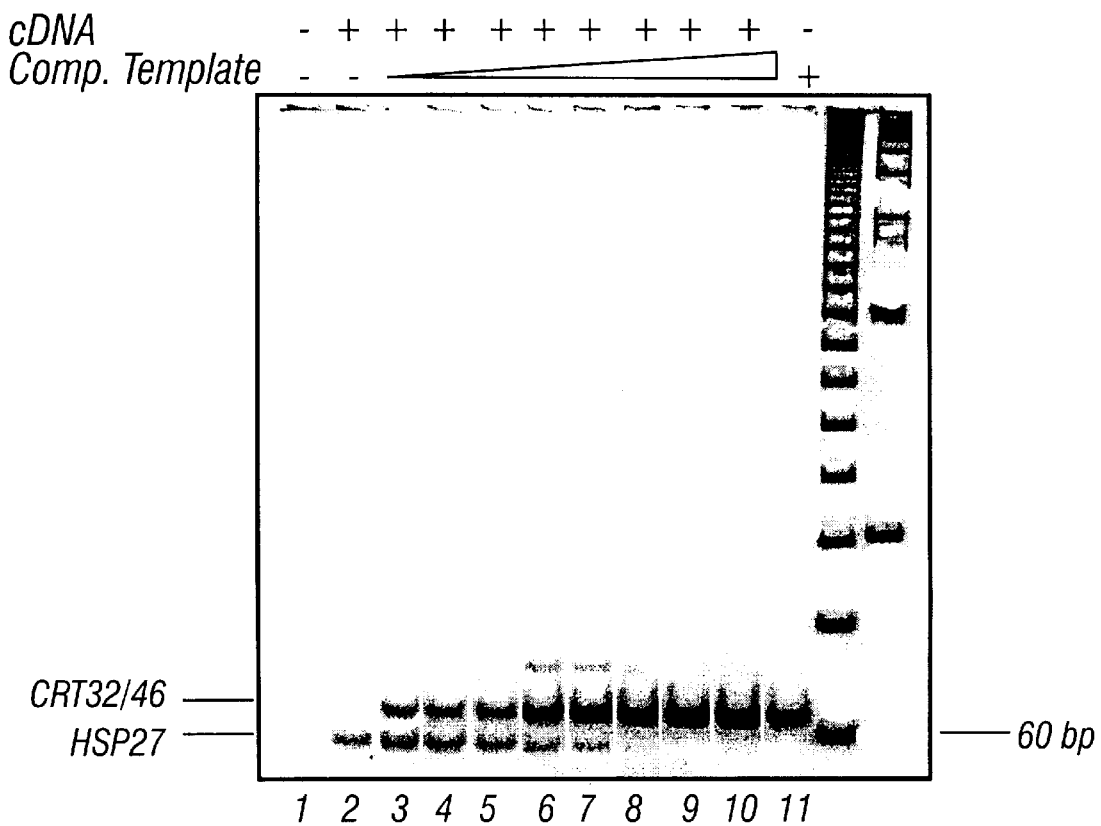

FIG. 5. Competitive RT-PCR™ with COP primers for HSP27. PCR™ reactions were set up with primers designed to assay HSP27 and 1.0 ng of cDNA derived from SKBR3 cells (lane 2–10) and no template was added to the control reaction (lane 1). The competitive template CRT32/46 was added in increasing amounts to reactions analyzed in lanes 3–10. The reaction analyzed in lane 11 contained only CRT32/46 as template. Reactions were analyzed on 5% polyacrylamide gels, stained with VistraGreen and visualized on a FluorImager.

Figure 6:
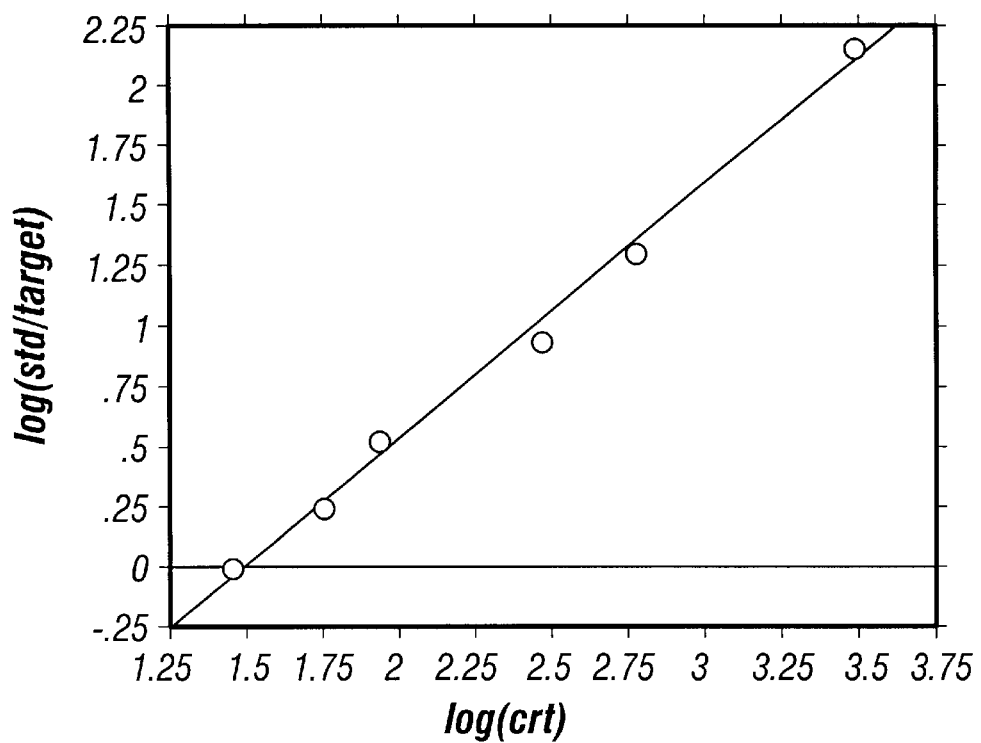

FIG. 6. Ouantitation of competitive RT-PCR™. The gel shown in FIG. 5 was quantitated, and the ratio of the standard intensity (ie., the CRT32/46 competitor) to the target intensity (ie., HSP27) was determined and plotted versus the standard concentration. The log-log plot is shown.

Figure 7A:
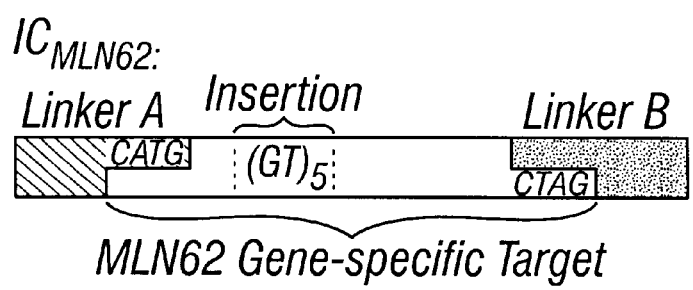
Figure 7B:
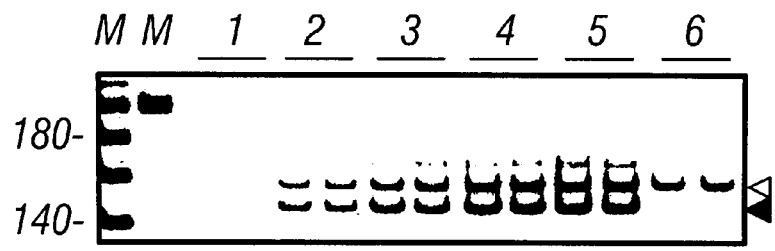
Figure 7C:
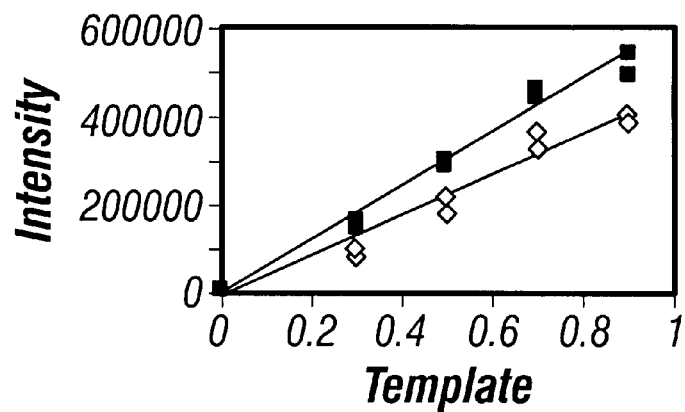

FIG. 7A, FIG. 7B, and FIG. 7C. Sensitivity of detection of MLN 62. A. The structure of the $IC_{MLN62}$ DNA is shown.

B. cDNA from normal human mammary epithelial cells (500 ng) was mixed with the $IC_{MLN62}$ DNA (25 pg), and genetags were prepared. The genetags were used as template for duplicate MLN62-specific COP reactions as follows: 1, no template; 2, 0.3 ng; 3, 0.5 ng; 4, 0.7 ng; 5, 0.9 ng. The reactions analyzed in lanes 6 contained 20 fg of $IC_{MLN62}$ as template. The intensity of the $IC_{MLN62}$-specific amplimer band (open arrowhead) increased linearly with template at least up to 80 fg/reaction (data not shown). C. The intensities of the endogenous MLN62-specific amplimer (151 bp, closed symbols) and the $IC_{MLN62}$-specific amplimer (161 bp, open symbols) were determined and are plotted as a function of genetag concentration. The ratio of the slopes of the two linear least-square fit lines was 1.28.

FIG. 8. Partial sequence of MLN 62 mRNA. Primers for COP are highlighted, and the poly(A) addition signal sequence is underlined. The A-end primer sequence (CATGCCTT), starting at position 1760, contains the CATG that is closest to the 3' end of the mRNA. The highlighted B-end primer sequence (TGAGATC), starting at position 1880, contains the first GATC following the A-end primer. Note that the actual B-end primer contains the reverse complement of the highlighted sequence (GATCTCA). This decreases the number of positions queried at the B-end by one, thus reducing the number of experiments by a factor of four.

Figure 9:
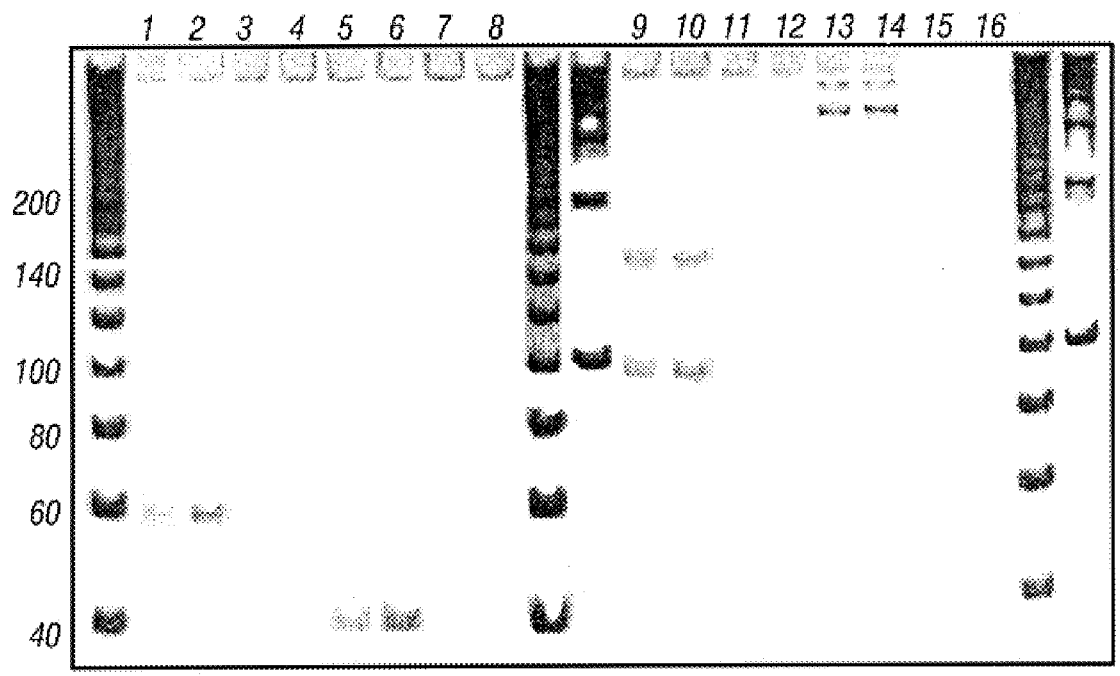

FIG. 9. COP analysis of four expressed genes in the SKBR3 cell line. PCR™ reactions were set up with 1.0 ng of cDNA derived from SKBR3 cells (lanes 1, 2, 5, 6, 9, 10, 13, and 14) or with no template (lanes 3, 4, 7, 9, 11, 12, 15, and 16) and COP primers designed for the four genes indicated in Table 2 as follows: lanes 1–4: HSP27; lanes 5–8: S5; lanes 9–12: MLN62; lanes 13–16: S16. After 28 cycles of amplification, samples were analyzed on a 5% polyacrylamide gel, stained with ethidium bromide and visualized on a UV light box. DNA size markers (20 and 100 bp ladders) were run for comparison in adjacent lanes.

Figure 10:
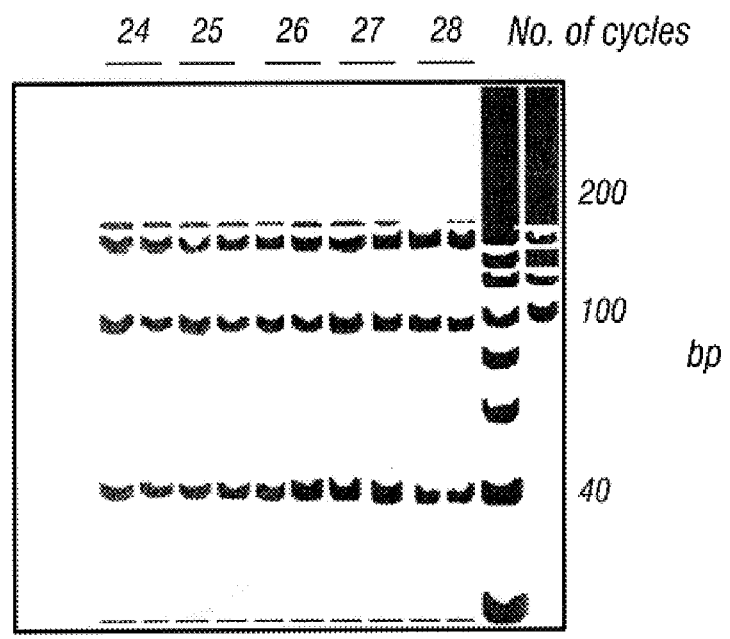

FIG. 10. Analysis of COP reactions: dependence on number of cycles. PCR™ reactions were set up with 1.0 ng of cDNA derived from SKBR3 cells and 80 ng of each of three COP primers that were selected to produce three major amplimers of approximately 40, 99 and 153 bp. Aliquots were removed after the indicated number of cycles and analyzed on a 5% polyacrylamide gel. The gel was stained with Vistra Green and visualized with a Pluorlinager. Marker DNAs (20 and 100 bp ladders) were loaded in the two right-hand lanes.

Figure 11:
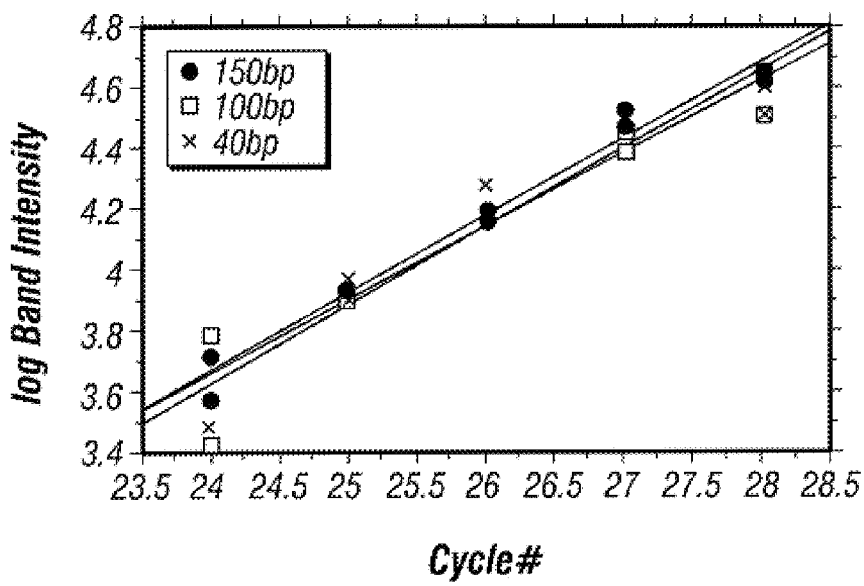

FIG. 11. Dependence of band intensity on number of cycles. The gel image in FIG. 10 was quantitated using Inage Quant software, and the logarithm of the intensity of each band was plotted versus the number of PCR™ cycles. All three bands exhibit an exponential increase at least for 27 cycles.

Figure 12:
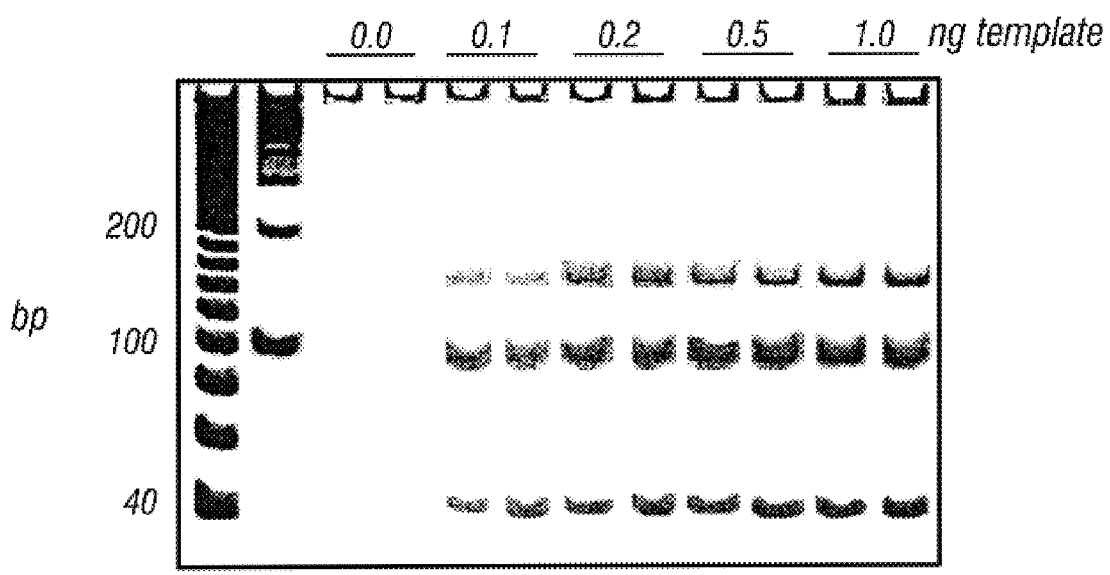

FIG. 12. Dependence on template concentration. PCR™ reactions were set up with the indicated amount of cDNA derived from SKBR3 cells and 80 ng each of three COP primers that were selected to produce three major amplimers of approximately 40, 99 and 153 bp. After 27 cycles, samples were analyzed on a 5% polyacrylamide gel. The gel was stained with Vistra Green and visualized with a FluorImager. Marker DNAs (20 and 100 bp ladders) were loaded in the two left lanes.

Figure 13:
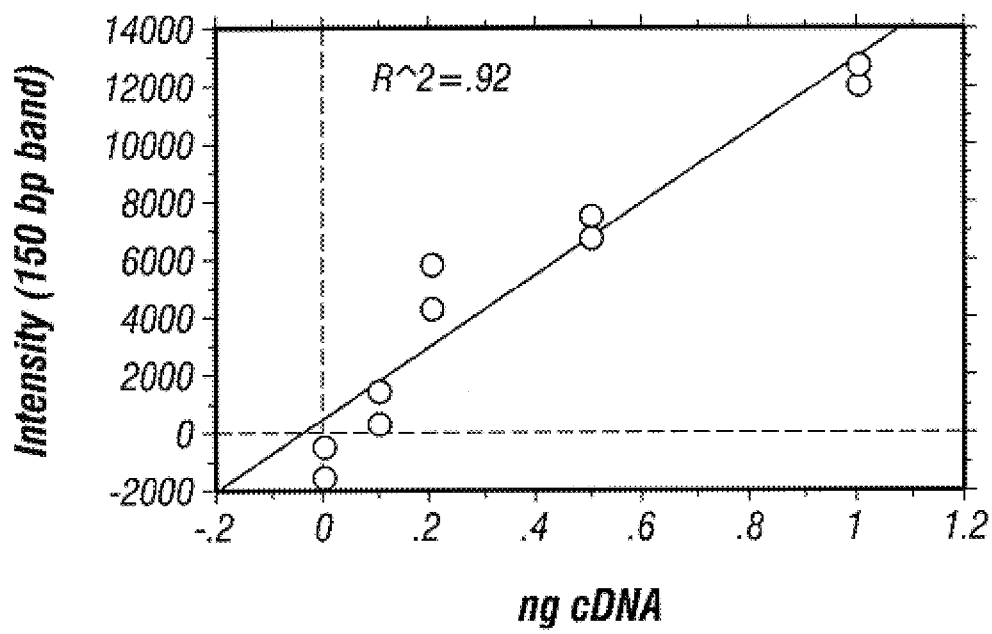

FIG. 13. Dependence of band intensity on template concentration. The gel image in FIG. 12 was quantitated using Image Quant software, and band intensity for the 150 bp band was plotted versus the amount of cDNA used as template in each PCR™ reaction. Similar data were also obtained for the 40 and 100 bp bands.

Figure 14:
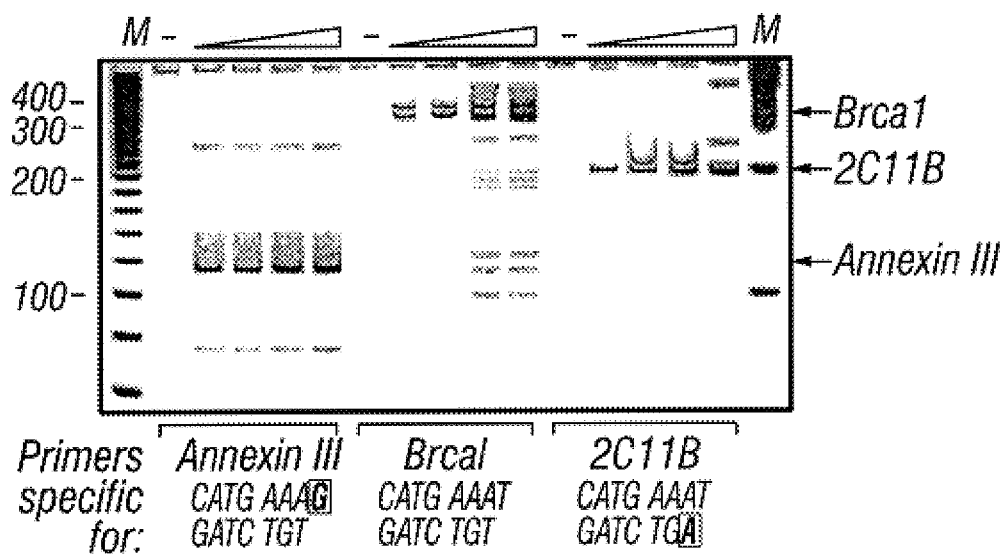

FIG. 14. Specificity of COP reactions for Annexin III, Brca1 and 2C11B.

Figure 15:
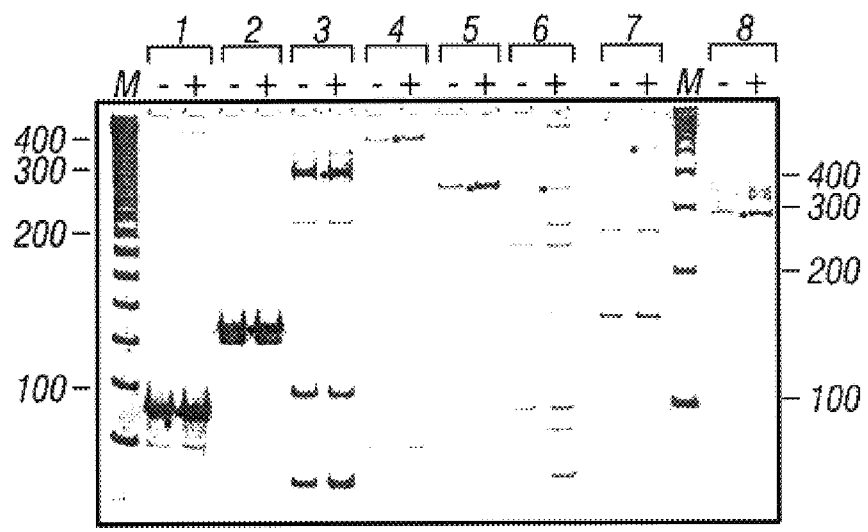

FIG. 15. E2F1-dedent chanm in expression of selected genes. COP PCR analysis was performed, using genetags prepared from wild-type or (−) or K5-E2F1 transgenic (+) keratinocytes. Reactions contained COP primers chosen to amplify specific genes and the expected amplimers are indicated in the Figure by black dots between the lanes. The selected genes and the size of the expected amplimers were: 1, Actg, 98 bp; 2, Rpl5, 130 bp; 3, Lmna, 291 bp; 4, Cdk7, 392 bp; 5, Yyl, 248 bp; 6, Hfh2, 254 bp; 7, Cdkn2a/p19$^{ARF}$, 508 bp; 8, Brca1, 291 bp.

Figure 16A:
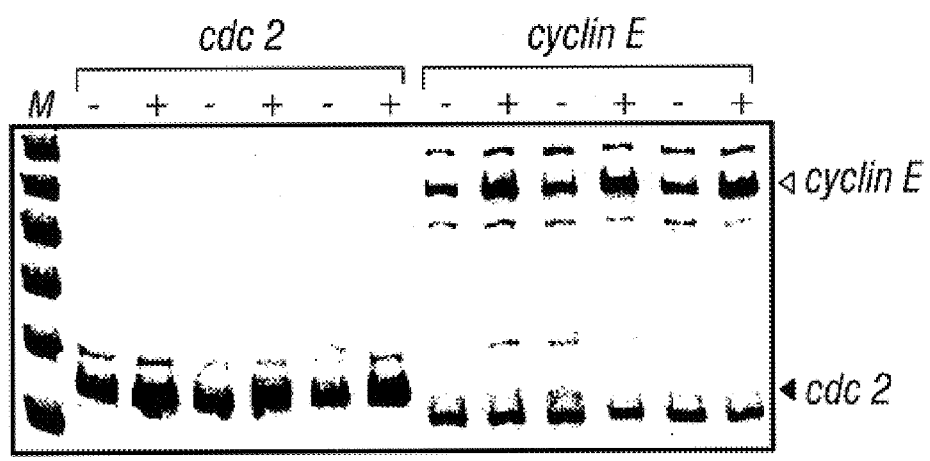
Figure 16B:
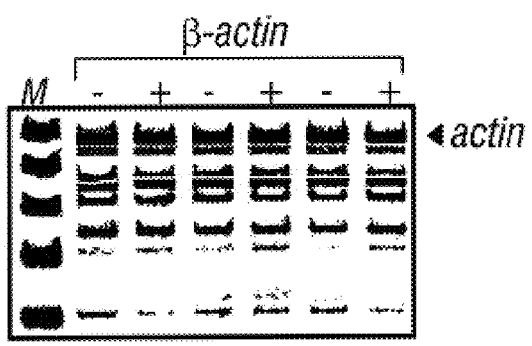

FIG. 16A and FIG. 16B. Changes in expression of E2F1-target genes. cDNA and genetags were prepared from keratinocyte cultures derived from newbomn wild-type mice (−) or their K5 E2F1 transgenic siblings (+). Replicate, paired PCR reactions were analyzed using primers specific for: A, Cdc2 and Ccne; B, Actb.

Figure 17A:
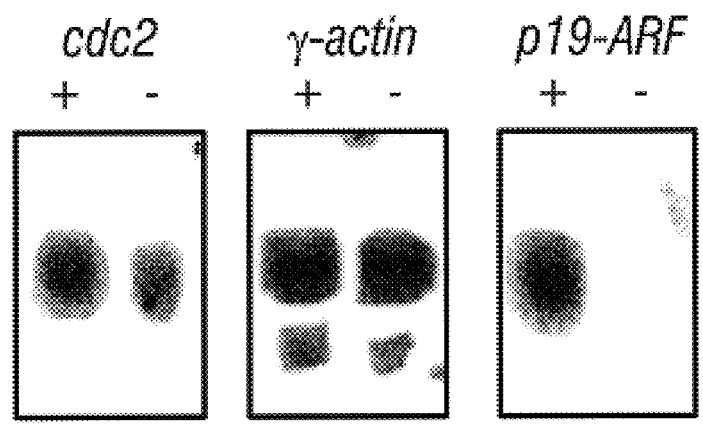
Figure 17B:
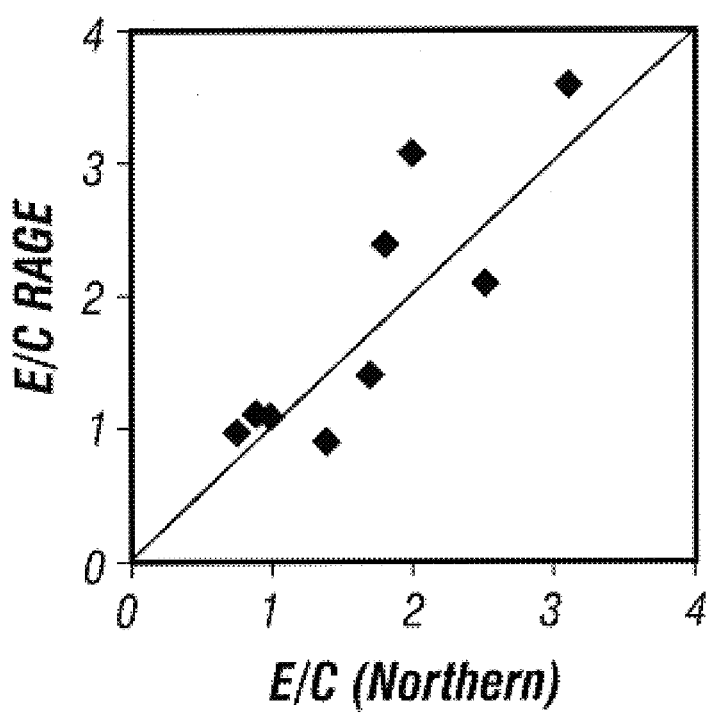

FIG. 17A and FIG. 17B. Validation of expression changes by Northern analyses. A. Northern analyses were performed using 20 μg of total RNA from wild type (−) or K5E2F1 transgenic (+) keratinocytes and probes specific for Cdkn2a/p19$^{ARF}$, Cdc2 or Actg. B. Similar analyses were canried out for 6 additional genes, and the expression ratio was determined after quantitation of the hybridized bands using a phosphorimager. The expression ratios for each of the 9 genes determined from Northern analysis (abcissa) is compared with the expression ratios obtained by COP analysis (ordinate). The line is that expected for perfect agreement between the two techniques.

Figure 18A:
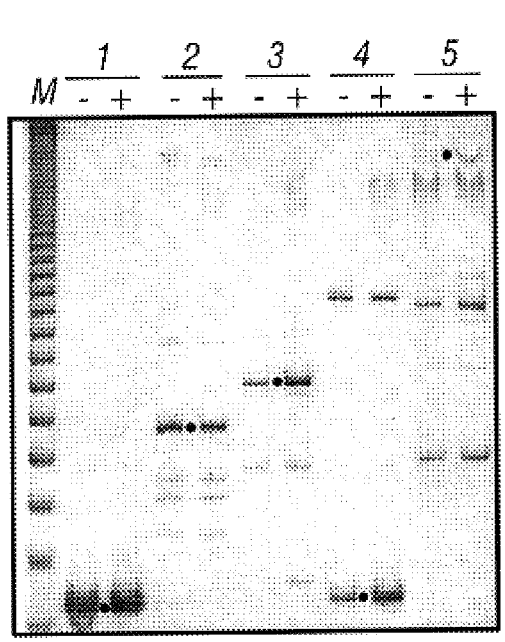
Figure 18B:
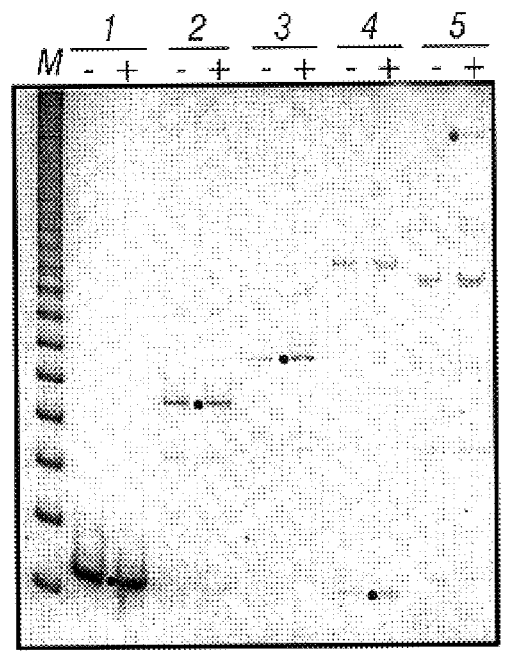
Figure 18C:
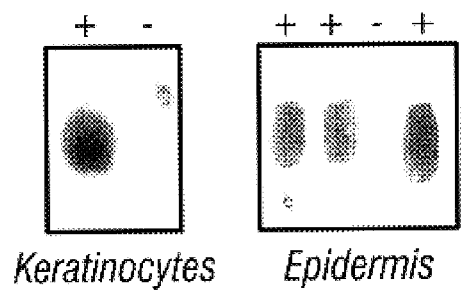

FIG. 18A, FIG. 18B and FIG. 18C. Expression changes in mouse skin and keratinocytes. RNA, cDNA & genetags were prepared from A. newborn keratinocytes or B. epidermal extracts derived from adult wild type (−) or K5 E2F1 transgenic (+) mice. In panels A & B, PCR reactions contained COP primers chosen to amplify: 1, Rps5, 108bp; 2, Actb, 176 bp; 3, Odc, 202 bp; 4, Ccng, 109 bp; 5, Cdkn2a/p19$^{ARF}$, 508 bp. Other symbols as in FIG. 6. C. Northern analyses were performed using 20 μg of total RNA from either newborn keratinocytes or adult skin of wild-type or transgenic mice and a probe specific for Cdkn2a/p19$^{ARF}$.

Figure 19:
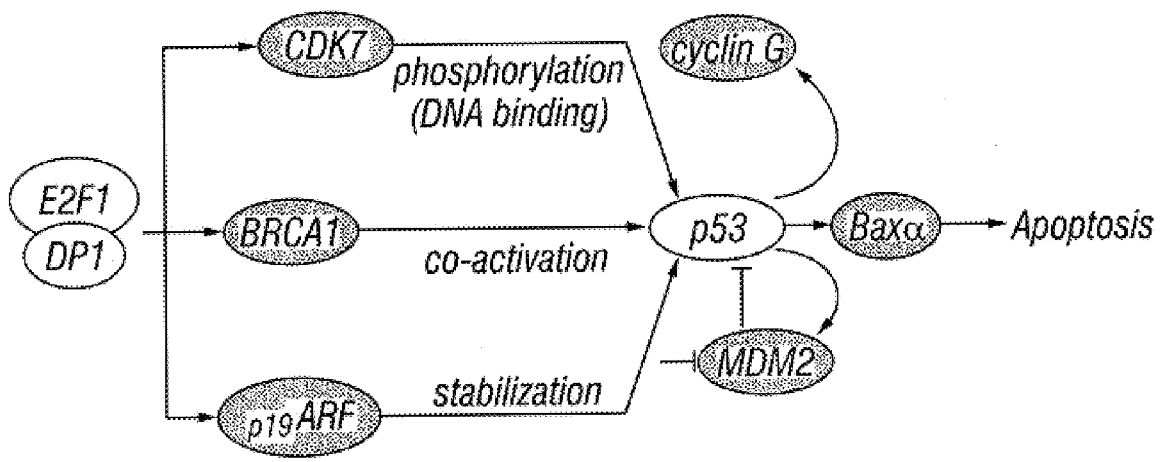

FIG. 19. Model for E2F1 effects on p53 and apoptosis. Darkened ovals represent genes that exhibit increased expression in the transgenic keratinocytes. Overexpression of E2F1 in keratinocytes leads to increased expression of CDK7, Brca1 and p19$^{ARF}$, which in turn increase p53 activity by the mechanisms indicated. This selectively increases the expression of three downstream targets of p53, Mdm2, cyclin G and Bax-α, but not in p21. This may predispose the cells to enter the apoptotic pathway under the influence of appropriate external stimuli, such as, carcinogen-induced DNA damage.

Figure 20:
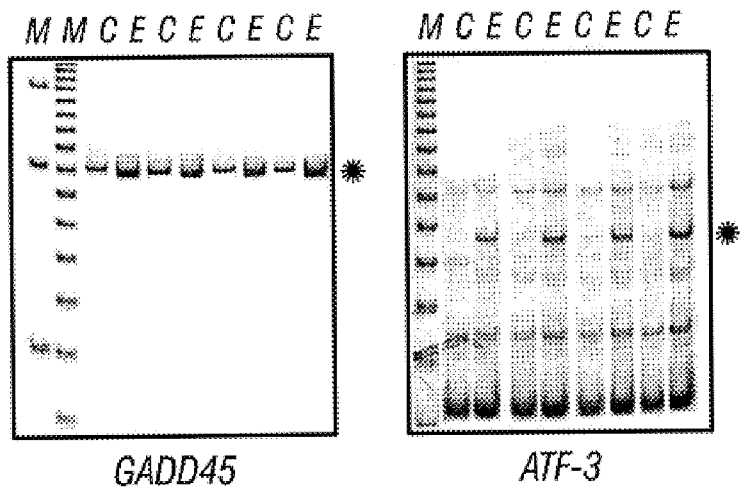

FIG. 20. COP analysis of GADD45 and ATF3 Genetags were prepared from HME87 cells 4 h after treatment with BPDE (lanes marked "E") or with solvent only (lanes marked "C"). Analyses in the left hand panel represent COP reactions with primers specific for the GADD45 gene product (expected length=204 bp). The band marked with the star was quantitated as GADD45. Lanes marked "M" contain DNA size markers. Analyses in the right hand panel represent COP reactions with primers specific for the ATF-3 gene product (expected length=155 bp). The band marked with the star was quantitated as ATF-3.

Figure 21:
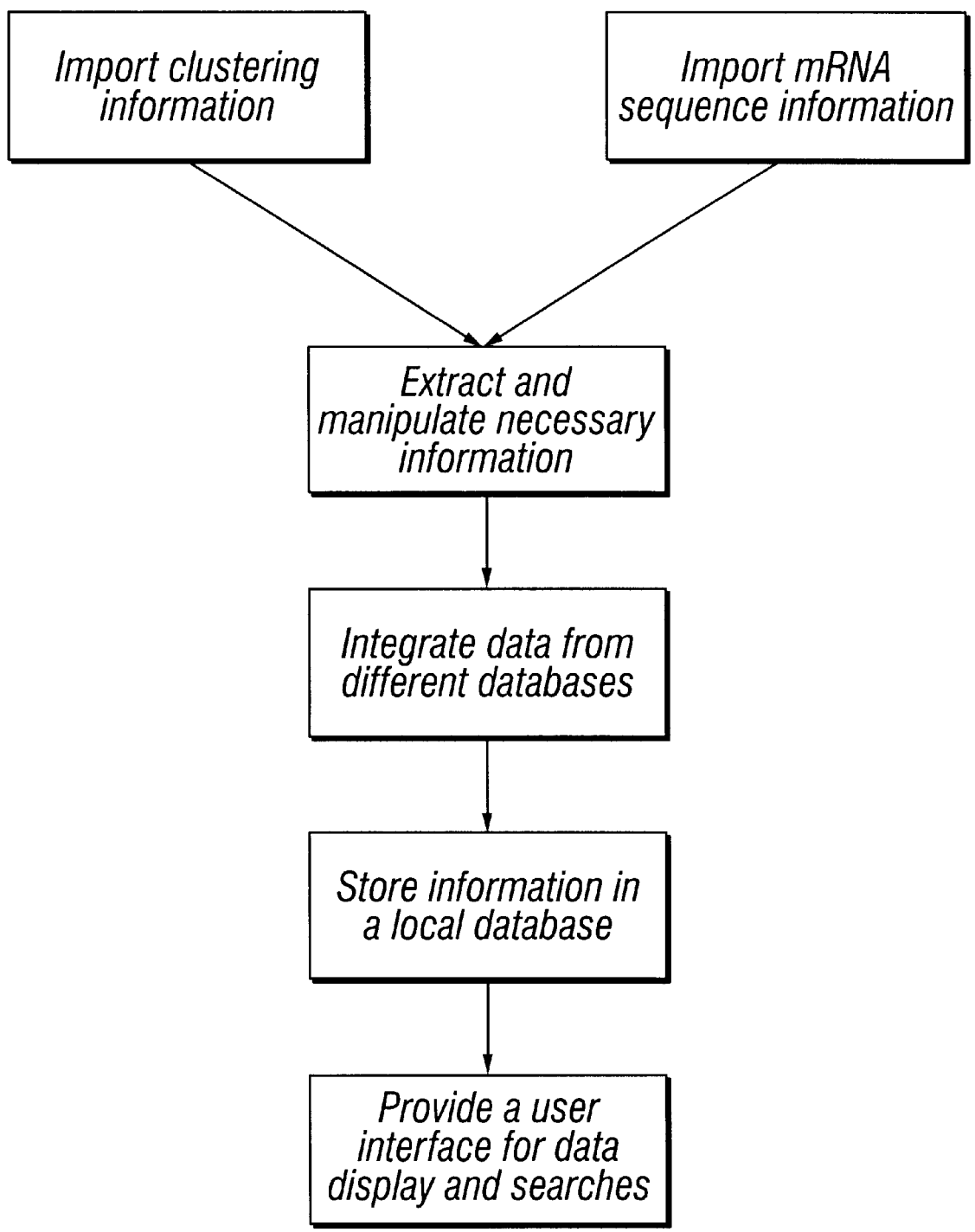

FIG. 21 Flow chart of one suitable embodiment of a computer program for analyzing COP data

DESCRIPTION OF ILLUSTRATIVE EMBODIMENTS

A. The Present Invention

Improved methods that allow rapid, detailed analysis of DNA, global expression patterns of genes, as well as expression patterns of defined sets of genes, are required. A preferred embodiment of the inventions comprises the ability to detect changes in the pattern of gene expression, for example, in the same cell type in different developmental stages, under different physiologic or pathologic conditions, when treated with different pharmaceuticals, mutagens, carcinogens, etc. allows the identification of genes as candidates for gene based therapies. It is however envisioned that the methods of the present invention may be utilized to analyze cellular DNA, genomic DNA, mitochondrial DNA, cDNA and synthetic DNA.

The present invention describes methods that allow rapid and quantitative detection of expression patterns of known as well as unknown genes. The overall strategy for these methods is described herein. In a preferred embodiment two common and frequently cutting restriction enzymes, such as 4-base-cutters, called for illustrating purposes A and B, are used to excise a unique fragment with defined sticky ends from each DNA. Short linker oligonucleotides, for example 12-mers with appropriate sticky ends, are added to each end, creating a collection of "genetags." It is an important feature of the present invention that when evaluating gene expression, no single molecular species of cDNA gives rise to more than one fragment in the collection of "genetags."

To ensure that a single, unique fragment is derived from each cDNA, prior to restriction digestion the cDNAs are immobilized through an attachment of one end of each cDNA to a solid substrate. For the purposes of illustration, this attachment may be through a biotin label incorporated at the 3' end of the cDNA. A substrate with covalently attached streptavidin can be utilized conveniently to immobilize the cDNA through specific, high affinity binding of biotin to streptavidin. In a preferred embodiment of the invention, the use of a biotinylated oligo dT for reverse transcription would also facilitate the isolation of the resulting cDNA molecule. Using biotinylated oligo dT allows for the isolation of labeled cDNA after it has been reverse transcribed from the mRNA, after an initial digestion or alternatively facilitates the initial isolation of mRNA on biotinylated oligo dT coated streptavidin beads followed by reverse transcription of the immobilized molecules. It is further envisioned that the DNA may be immobilized via its 5' end. In this embodiment, an anchorable moiety may be incorporated on the 5' end of the polynucleotide molecule through TdT incorporation of labeled nucleotides at the 5' terminus of the molecule (Ying, 1999).

In the context of the present invention, the inventors envision the term "immobilized" to encompass a meaning including; appended, attached, covalently or non-covalently bound, adhered, ligated, affixed, joined or fused. It is envisioned that the immobilizing may comprise an interaction between the DNA molecule and a substrate that may be either permanent or transitory. In the context of the present invention, the inventors envision the term anchorable moiety to encompass of a means of adherence or alternatively a means of immobilization.

The immobilized DNA is initially cut with restriction enzyme A, and the fragments that remain immobilized on the substrate are retained. These fragments contain only those sequences present in the original DNA between the last recognition sequence for restriction enzyme A, and the 3' end of the DNA molecule. These fragments are then cut with restriction enzyme B, and the fragments that are no longer immobilized are collected. Digestion in this fashion results in at most one unique fragment of each DNA molecule obtained in this procedure, with one A-specific sticky end, and one B-specific sticky end. Linker oligonucleotides of two different sequences are added to these fragments, producing a preparation called "A/B genetags," due to the use of restriction enzyme A prior to restriction enzyme B.

The use of 4-base cutter restriction enzymes in the preparation of genetags permits the analysis of virtually any DNA molecule since recognition sites for both the enzymes will be present in virtually any DNA. However, only about half of the DNAs will have a B recognition site closer to the 3' end than any A recognition site. Thus, after the first restriction cut, only about half of the retained DNAs will contain a B restriction recognition sequence, and thus produce a fragment in the A/B genetags. The remaining half of the DNAs will have an A recognition site closer to the 3' end than any B recognition site. In a preferred embodiment the order in which the A and B cuts are made is reversed, allowing appropriate fragments to be obtained from the other portion of the genome. After addition of linkers these figments are designated "B/A genetags." The combination of B/A and A/B genetags would therefore encompass virtually all of the expressed genes present in a given sample. In the context of evaluating gene expression, while effectively all of the message in a sample should be present in a combination of B/A and A/B genetags, the immobilization of the cDNA during digestion insures that each mRNA molecule is subsequently represented by only a single amplimer product.

It is further envisioned that to amplify the amplimer product, a first set of primers may be constructed for the A end of the genetag, containing the sequence of the A-end linker, the A restriction enzyme recognition sequence, and a specificity region extending 3–8 nucleotides past the A restriction enzyme recognition sequence. Primers containing all possible combinations of A, C, G and T at each position of the specificity region comprise the set of A-end primers. For the purposes of illustration, the specificity region can be constructed to be 4 nucleotides in length, producing a set of 256 different A-end primers (4×4×4×4=256), wherein each possible nucleotide is represented at each respective site in the specificity region.

A second set of primers may be constructed for the B end of the genetag, containing the sequence of the B-end linker, the B restriction enzyme recognition sequence, and a specificity region extending 3–8 nucleotides past the B restriction enzyme recognition sequence. Primers containing all possible combinations of A, C, G and T at each position of the specificity region comprise the set of B-end primers. For the purposes of illustration, the specificity region can be constructed to be 3 nucleotides in length, producing a set of 64 different B-end primers (4×4×4=64).

A particular pair of A-end and B-end primers is combined with either A/B or B/A, genetags, and PCR™ reactions are carried out under conditions where amplification is, proportional to the template concentration. An amplimer product is produced if a gene tag is present whose specificity region sequence corresponds to the sequences of the specificity regions of the A-end and B-end primers. These amplimers are quantitated by, means well known to practitioners of the art, and in the context of evaluating gene expression, the amount of a given amplimer is proportional to the level of expression of the corresponding gene in the cDNA preparation.

In order to standardize the amount of genetag from one sample to another, a set of amplification reactions will be carried out using pairs of primers that amplify known constitutively expressed genes. Because individual primers in each set have very similar base compositions, differing from each other only in the specificity regions, all amplification reactions can be carried out under the same conditions of ionic strength and annealing temperature, typically from 58–62° C. In reactions where the specificity regions of the primers are rich in A and T nucleotides, it is sometimes advantageous to use the lower annealing temperature (58° C). In reactions where the specificity regions of the primers are rich in G and C nucleotides, it is sometimes advantageous to use the higher annealing temperature (62° C).

In the illustrative example, the total number of unique reactions that can be performed is the product of the number of genetag preparations (2), the number of A-end primers (256) and the number of B-end primers: 2×256×64=32,768. Assuming the human genome contains about 60,000–90,000 genes, each unique reaction is expected to produce amplimers corresponding to 2–3 genes, on average.

To obtain a unique specification, further information can be obtained by size fractionation of the amplimer products or by testing for the presence of other restriction enzyme recognition sequences or by determining the sequence of the amplimer. Changes in the length of the two specificity regions, in an alternative embodiment, will alter the total number of unique reactions that must be performed to assay the entire genome. If n is the sum of the lengths of the two specificity regions, the number of unique reactions is $2 \times 4^N$.

In principle, relative measurements of the expression of all genes in the genome can be obtained with the method described above by carrying out all 32,768 unique reactions and measuring the amount of each amplimer formed. In practice, it often is desirable to measure the expression levels for a particular subset of known genes, for example, all known genes that code for cyclins. To do this, prior knowledge of the sequence of each mRNA is needed in order to predict the exact sequences of the primers to be used for its amplification, and to predict the length, or other identifying properties, of the corresponding amplimer.

Computer code that can be executed on a digital computer has been written and used to construct a database for this purpose. One method implementing such a program involves importing clustering information from publicly available databases of the National Library of Medicine, importing mRNA sequence information from publicly available databases of the National Library of Medicine. The necessary information is then extracted and manipulated and the data from the different databases integrated (primer locations and sequences, polyA signals, coding sequences, LocusLink and Unigene numbers, etc.). The information is then stored in a local database and a user interface provided for data display and searches (FIG. 21). With the benefit of the present disclosure, those having skill in the art will recognize that other methods for forming a computer program with the disclosed function are available.

All mRNA sequences existing in the publicly available GenBank database that are derived from human, mouse and rat, have been separately loaded into this database, and the positions, sequences, orientations and lengths of the corresponding genetags that would be obtained with two particular restriction enzymes, NlaII and DpnII, have been extracted from the sequence information, as well as the sequences of the A-end and B-end primers needed to amplify these genetags. In addition, computer code has been written and used to update the database each month, adding information from sequences that have recently been deposited in GenBank. Additionally, computer code has been written that allows individual GenBank files to be searched for the above information, and also that allows GenBank libraries to be searched for entries that would be amplified by a given pair of A-end and B-end primers.

Nucleic Acids

Genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the MiRNA must be transported into the cytoplasm for the process of translation, which converts the code of the mRNA into a sequence of amino acids to form protein. In order to direct transport into the cytoplasm, the 3' ends of mRNA molecules are post-transcriptionally modified by addition of several adenylate residues to form the "polyA" tail. This characteristic modification distinguishes gene expression products destined to make protein from other molecules in the cell, and thereby provides one means for detecting and monitoring the gene expression activities of a cell.

Some of the exemplary genes that may be monitored for expression are genes involved in cancer pathways, for example, oncogenes, tumor suppressor genes, DNA repair genes, genes involved in signal transduction, etc. Loss of control of cell-cycle regulatory genes, or genes controlling apoptotic pathways can lead to the development of cancers.

Other genes that may be monitored for changes in expression levels are genes that change in response to a pharmaceutical compound, or genes that are involved in metabolism and disposition of pharmaceutical compounds, hormones or toxicants. This can pinpoint genes involved in pathways of the pathological condition.

Yet other genes that can be monitored are genes that change in response to development and growth, or that are responsible for controlling developmental pathways. Studies directed towards aging for example can benefit vastly from these type of experiments.

Furthermore, gene expression changes may be monitored in response to treatment of cells or tissues with a host of chemical compounds such as mutagens, teratogens, carcinogens, pesticides, pollutants, etc., or biological compounds such as hormones, growth factors, cytokines, etc.

Patterns of expression for genes not connected with the pathways mentioned previously, as well as genes whose function is not yet identified, can be monitored for the purpose of establishing expression patterns that may be of diagnostic or prognostic values, or may be indicative of past or current exposure to certain pharmaceutical compounds, toxicants or drugs of abuse.

B. Detection of Nucleic Acids

1. Oligonucleotide Probes and Primers

Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of annealing to the nucleic acid segment being described under relatively stringent conditions such as those described herein.

Primers should be of sufficient length to provide specific annealing to a RNA or DNA tissue sample. The use of a primer of between about 10–14, 15–20, 21–30 or 31–40 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

Sequences of 17 bases long should occur only once in the human genome and, therefore, suffice to specify a unique target sequence. Although shorter oligomers are easier to make and increase m vivo accessibility, numerous other factors are involved in determining the specificity of hybridization. Both binding affinity and sequence specificity of an oligonucleotide to its complementary target increases with increasing length It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800, and longer are contemplated as well. Accordingly, nucleotide sequences may be selected for their ability to selectively form duplex molecules with complementary stretches of genes or RNAs or to provide primers for amplification of DNA or RNA from cells, cell lysates and tissues. The method of using probes and primers of the present invention is in the selective amplification and detection of genes, changes in gene expression, gene polymorphisms, single nucleotide polymorphisms, changes in mRNA expression wherein one could be detecting virtually any gene or genes of interest from any species. The target polynucleotide will be RNA molecules, mRNA, cDNA, DNA or amplified DNA. By varying the stringency of annealing, and the region of the primer, different degrees of homology may be discovered.

The particular amplification primers of the present invention will be specific oligonucleotides which encode particular features including the recognition site for frequently cutting restriction enzymes, primer sequences, and degenerate sequences of 3, 4, 5, 6, 7, 8 or more consecutive bases to ensure amplification of all target genes. Generally, the present invention may involve the use of a variety of other PCR™ primers which hybridize to a variety of other target sequences.

Amplification primers may be chemically synthesized by methods well known within the art (Agrawal, 1993). Chemical synthesis methods allow for the placement of detectable labels such as fluorescent labels, radioactive labels etc. to be placed virtually anywhere within the polynucleic acid sequence. Solid phase method of synthesis also may be used.

The amplification primers may be attached to a solid-phase, for example, a latex bead; or the surface of a chip. Thus, the amplification carried out using these primers will be on a solid support/surface.

Furthermore, some primers of the present invention will have a recognition moiety attached. A wide variety of appropriate recognition means are known in the art, including fluorescent labels, radioactive labels, mass labels, affinity labels, chromophores, dyes, electroluminescence, chemiluminescence, enzymatic tags, or other ligands, such as avidin/biotin, or antibodies, which are capable of being detected and are described below.

2. Amplification i. PCR™

In some embodiments, poly-A mRNA is isolated and reverse transcribed (referred to as RT) to obtain cDNA which is then used as a template for polymerase chain reaction (referred to as PCR™) based amplification. In other embodiments, cDNA may be obtained and used as a template for the PCR™ reaction. In PCR™, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred.

The primers are used in any one of a number of template dependent processes to amplify the target-gene sequences present in a given template sample. One of the best known amplification methods is PCR™ which is described in detail in U.S. Pat. No's. 4,683,195, 4,683,202 and 4,800,159, each incorporated herein by reference.

In PCR™, two primer sequences are prepared which are complementary to regions on opposite complementary strands of the target-gene(s) sequence. The primers will hybridize to form a nucleic-acid:primer complex if the target-gene(s) sequence is present in a sample. An excess of deoxyribonucleoside triphosphates are added to a reaction mixture along with a DNA polymerase, e.g., Taq polymerase, that facilitates template-dependent nucleic acid synthesis.

If the target-gene(s) sequence:primer complex has been formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles", are conducted until a sufficient amount of amplification product is produced.

Next, the amplification product is detected. In certain applications, the detection may be performed by visual means. Alternatively, the detection may involve indirect identification of the product via fluorescent labels, cherniluminescence, radioactive scintigraphy of incorporated radiolabel or incorporation of labeled nucleotides, mass labels or even via a system using electrical or thermal impulse signals (Affymax technology).

A reverse transcriptase PCR™ amplification procedure may be performed in order to quantify the amount of MnRNA amplified. Methods of reverse transcribing RNA into cDNA are well known and described in Sambrook et al., 1989. Alternative methods for reverse transcription utilize thermostable DNA polymerases. These methods are described in WO 90/07641, filed Dec. 21, 1990.

ii LCR

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

iii. Qbeta Replicase

Qbeta Replicase, described in PCT Patent Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected.

iv. Isothermal Amplification

An isothermal amplification method, in which restriction endonucleases and ligases are used to achieve the amplification of target molecules that contain nucleotide 5'-[α-thio]-triphosphates in one stand of a restriction site also may be useful in the amplification of nucleic acids in the present invention. Such an amplification method is described by Walker et al. 1992, incorporated herein by reference.

V. Strand Displacement Amplification

Strand Displacement Amplification (SDA) is another method of carrying out isothermal amplification of nucleic acids which involves multiple rounds of strand displacement and synthesis, ie., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

vi. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

vii. Transcription-Based Amplification

Other nucleic acid amplification procedures include transcription-based amplification systems (rAS), including nucleic acid sequence based amplification (NASBA) and 3SR, Kwoh et al., 1989; PCT Patent Application WO 88/10315 et al., 1989, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

viii. Other Amplification Methods

Other amplification methods, as described in British Patent Application No. GB 2,202,328, and in PCT Patent Application No. PCT/US89/01025, each incorporated herein by reference, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Davey et al., European Patent Application No. 329,822 (incorporated herein by reference) disclose a nucleic acid amplification process involving cyclically synthesizing single-stranded RNA ("ssRNA"), ssDNA, and double-stranded DNA (dsDNA), which may be used in accordance with the present invention.

The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, ie., new templates are not produced from the resultant RNA transcripts.

Other suitable amplification methods include "race" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention, Wu et al., 1989, incorporated herein by reference).

3. Restriction Enzymes

Restriction-enzymnes recognize specific short DNA sequences four to eight nucleotides long (see Table 1), and cleave the DNA at a site within this sequence. In the context of the present invention, restriction enzymes are used to cleave cDNA molecules at sites corresponding to various restriction-enzymne recognition sites. Frequently cutting enzymes, such as the four-base cutter enzymes, are preferred as this yields DNA fragments that are in the right size range for subsequent amplification reactions. Some of the preferred four-base cutters are NlaIII, DpnII, Sau3AI, Hsp92II, MboI, NdeII, Bsp1431, Tsp509 I, MhaI, HinP1I HpaII, MspI, Taq alphaI, MaeII or K2091.

As the sequence of the recognition site is known (see list below), primers can be designed comprising nucleotides corresponding to the recognition sequences. If the primer sets have in addition to the restriction recognition sequence, degenerate sequences corresponding to different combinations of nucleotide sequences, one can use the primer set to amplify DNA fragments that have been cleaved by the particular restriction enzyme. The list below exemplifies the currently known restriction enzymes that may be used in the invention.

TABLE 1

RESTRICTION ENZYMES

| Enzyme Name | Recognition Sequence |
|---|---|
| AatII | GACGTC |
| Acc65 I | GGTACC |
| Acc I | GTMKAC |
| Aci I | CCGC |
| Acl I | AACGTT |
| Afe I | AGCGCT |
| Afl II | CTTAAG |
| Afl III | ACRYGT |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| ApaL I | GTGCAC |
| Apo I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |
| Bcl I | TGATCA |
| Bfa I | CTAG |
| Bgl I | GCCNNNNNGGC |

TABLE 1-continued

RESTRICTION ENZYMES

| Enzyme Name | Recognition Sequence |
|---|---|
| Bgl II | AGATCT |
| Blp I | GCTNAGC |
| Bmr I | ACTGGG |
| Bpm I | CTGGAG |
| BsaA I | YACGTR |
| BsaB I | GATNNNNATC |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| Bsl I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC |
| BstB I | TTCGAA |

TABLE 1-continued

RESTRICTION ENZYMES

| Enzyme Name | Recognition Sequence |
|---|---|
| BstE II | GGTNACC |
| BstF5 I | GGATGNN |
| BstN I | CCWGG |
| BstU I | CGCG |
| BstX I | CCANNNNNNTGG |
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinPl I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |
| MspAl I | CMGCKG |
| Msp I | CCGG |
| Mwo I | GCNNNNNNNGC |
| Nae I | GCCGGC |
| Nar I | GGCGCC |
| Nci I | CCSGG |
| Nco I | CCATGG |
| Nde I | CATATG |
| NgoMI V | GCCGGC |
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| Ple I | GAGTC |

TABLE 1-continued

RESTRICTION ENZYMES

| Enzyme Name | Recognition Sequence |
|---|---|
| Pme I | GTTTAAAC |
| Pml I | CACGTG |
| PpuM I | RGGWCCY |
| PshA I | GACNNNNGTC |
| Psi I | TTATAA |
| PspG I | CCWGG |
| PspOM I | GGGCCC |
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |

TABLE 1-continued

RESTRICTION ENZYMES

| Enzyme Name | Recognition Sequence |
|---|---|
| Tli I | CTCGAG |
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTGG |
| Xho I | CTCGAG |
| Xma I | CCCGGG |
| Xmn I | GAANNNNTTC |

4. Other Enzymes

Other enzymes that may be used in conjunction with the invention include nucleic acid modifying enzymes listed in the following tables.

TABLE 2

POLYMERASES AND REVERSE TRANSCRIPTASES

Thermostable DNA Polymerases:

OmniBase ™ Sequencing Enzyme
Pfu DNA Polymerase
Taq DNA Polymerase
Taq DNA Polymerase, Sequencing Grade
TaqBead ™ Hot Start Polymerase
AmpliTaq Gold
Tfl DNA Polymerase
Tli DNA Polymerase
Tth DNA Polymerase DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T4 DNA Polymerase Reverse Transcriptases:

AMV Reverse Transcriptase
M-MLV Reverse Transcriptase

TABLE 3

DNA/RNA MODIFYING ENZYMES

Ligases:
T4 DNA Ligase
Kinases:
T4 Polynucleotide Kinase

5. Labels

Recognition moieties incorporated into primers, incorporated into the amplified product during amplification, or attached to probes are useful in identification of the amplified molecules. A number of different labels may be used for the purpose such as fluorophores, chromophores, radioisotopes, enzymatic tags, antibodies, chemniluminescence, electroluminescence, affinity labels, etc. One of skill in the art will recognize that these and other fluorophores not mentioned herein can also be used with success in this invention.

Examples of affinity labels include but are not limited to the following: an antibody, an antibody fragment, a receptor protein, a hormone, biotin, DNP, or any polypeptide/protein molecule that binds to an affinity label and may be used for separation of the amplified gene.

Examples of enzyme tag include enzymes such as such as urease, alkaline phosphatase or peroxidase to mention a few and colorimetric indicator substrates can be employed to provide a detection means visible to the human eye or spectrophotometrically, to identify specific hybridization with complementary nucleic acid-containing samples. All these examples are generally known in the art and the skilled artisan will recognize that the invention is not limited to the examples described above.

The following fluorophores are specifically contemplated to be useful in practicing the present invention. Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

6. Methods of Immobilization

Immobilization of the DNA may be achieved by a variety of methods involving either non-covalent or covalent interactions between the immobilized DNA comprising an anchorable moiety and an anchor. In a preferred embodiment of the invention immobilization consists of the non-covalent coating of a solid phase with streptavidin or avidin and the subsequent immobilization of a biotinylated polynucleotide (Holmstrom, 1993). It is further envisioned that immobilization may occur by precoating a polystyrene or glass solid phase with poly-L-Lys or poly L-Lys, Phe, followed by the covalent attachment of either amino- or sulfhydryl-modified polynucleotides using bifunctional crosslinking reagents (Running, 1990 and Newton, 1993).

Immobilization may also take place by the direct covalent attachment of short, 5'-phosphorylated primers to chemically modified polystyrene plates ("Covalink" plates, Nunc) Rasmussen, (1991). The covalent bond between the modified oligonucleotide and the solid phase surface is introduced by condensation with a water-soluble carbodiimide. This method facilitates a predominantly 5'-attachment of the oligonucleotides via their 5'-phosphates.

Nikiforov et al. (U.S. Pat. No. 5,610,287 incorporated herein by reference) describes a method of non-covalently immobilizing nucleic acid molecules in the presence of a salt or cationic detergent on a hydrophilic polystyrene solid support containing a hydrophilic moiety or on a glass solid support. The support is contacted with a solution having a pH of about 6 to about 8 containing the synthetic nucleic acid and a cationic detergent or salt. The support containing the immobilized nucleic acid may be washed with an aqueous solution containing a non-ionic detergent without removing the attached molecules.

Another commercially available method envisioned by the inventors to facilitate immobilization is the "Reacti-Bind.TM. DNA Coating Solutions" (see "Instructions—Reacti-Bind.TM. DNA Coating Solution" 1/1997). This product comprises a solution that is mixed with DNA and applied to surfaces such as polystyrene or polypropylene.

After overnight incubation, the solution is removed, the surface washed with buffer and dried, after which it is ready for hybridization. It is envisioned that similar products, i.e. Costar "DNA-BIND™" or. hmmobilon-AV Affinity Membrane (IAV, Millipore, Bedford, Mass.) are equally applicable to immobilize the respective fragment.

7. Separation and Quantitation Methods

Following amplification, it may be desirable to separate the amplification products of several different lengths from each other and from the template and the excess primer for the purpose analysis or more specifically for determining whether specific amplification has occurred.

i Gel electrophoresis

In one embodiment, amplification products are separated by agarose, agarose-acrylamide or polyacrylarnide gel electrophoresis using standard methods (Sambrook et al., 1989).

ii. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin or antigen can be captured with beads bearing avidin or antibody, respectively.

iii. Microfluidic Techniques

Microfluidic techniques include separation on a platform such as microcapillaries, designed by ACLARA Bio-Sciences Inc., or the LabChip™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487 and 5,296,375, discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

iv. Capillary Electrophoresis

In some embodiments, it may be desirable to provide an additional, or alternative means for analyzing the amplified genes. In these embodiment, micro capillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, for example, Woolley and Mathies, 1994. Microcapillary array electrophoresis generally provides a rapid method for size-based sequencing, PCR™ product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Micro-fabrication of microfluidic devices including microcapillary electrophoretic devices has been discussed in detail in, for example, Jacobsen et al., 1994; Effenhauser et al., 1994; Harrison et al., 1993; Effenhauser et al., 1993; Manz et al., 1992; and U.S. Pat. No. 5,904,824, here incorporated by reference. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

v. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the known in the art can be found summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include Schram, 1990 and Crain, 1990 here incorporated by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al. Biomedical Environmental Mass Spectrometry 14, 111–116 (1987)).

Two ionization/desorption techniques are electrospray/ionspray (ES) and matrix-assisted laser desorption/ionization (MALDI). ES mass spectrometry was introduced by Fenn, 1984; PCT Application No. WO 90/14148 and its applications are summarized in review articles, for example, Smith 1990 and Ardrey, 1992. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp 1990. Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williamns, 1989). More recently, this the use of infrared lasers (IR) in this technique (as opposed to UV-lasers) has been shown to provide mass spectra of larger nucleic acids such as, synthetic DNA, restriction enzyme fragments of plasmid DNA, and RNA transcripts upto a size of 2180 nucleotides (Berkenkamp, 1998). Berkenkamp also describe how DNA and RNA samples can be analyzed by limited sample purification using MALDI-TOF IR.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

vii Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, 1948. The distance between donor and acceptor dyes at which energy transfer efficiency is 50% is referred to as the Forster distance ($R_o$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Several formats for FET hybridization assays are reviewed in Nonisotopic DNA Probe Techniques (1992. Academic Press, Inc., pgs. 311–352).

Homogeneous methods employing energy transfer or other mechanisms of fluorescence quenching for detection of nucleic acid amplification have also been described. Higuchi, 1992, discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee, 1993, discloses a real-time detection method in which a doubly-labeled detector probe is cleaved in a target amplification-specific manner during PCR™. The detector probe is hybridized downstream of the amplification primer so that the 5'–3' exonuclease activity of Taq polymerase digests the detector probe, separating two fluorescent dyes which form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TALIC), FITC/Texas Red.™. Molecular Probes), FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and maybe routinely used to link the donor and acceptor dyes at their respective sites in the detector nucleic acid.

viii. Chip Technologies

Specifically contemplated by the present inventors are chip-based DNA technologies such as those described by Hacia et al., 1996 and Shoemaker et al., 1996. These techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization, Pease et al., 1994; Fodor et al., 1991.

In the present invention, the inventors contemplate the preparation of a high-density array of COP primers on a chip (or on any other solid surface) and conduct the DNA amplification on this solid-phase.

ix. OIA

The inventor's envision the use of BioStar's OIA technology to quantitate the amplified product. OIA uses the mirror-like surface of a silicon wafer as a substrate. A thin film optical coating and capture antibody is attached to the silicon wafer. White light reflected through the coating appears as a golden background color. This color does not change until the thickness of the optical molecular thin film is changed.

When a positive sample is applied to the wafer, binding occurs between the ligand and the antibody. When substrate is added to complete the mass enhancement, a corresponding change in color from gold to purple/blue results from the increased thickness in the molecular thin film.

x. Real time PCR

RNA or DNA may be quantitated using the Real-Time PCR technique (Higuchi, 1992). By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR products and the relative mRNA abundance is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundance of a RNA or DNA species can be determined by Real-Time PCR for a collection of RNA or DNA populations is that the concentrations of the amplified PCR products must be sampled when the PCR reactions are in the linear portion of their curves.

The second condition that must be met for an RT-PCR experiment to successfully determine the relative abundance of a particular MnRNA species is that relative concentrations of the amplifiable cDNAs must be normalized to some independent standard. The goal of an Real-Time PCR experiment is to determine the abundance of a particular RNA or DNA species relative to the average abundance of all RNA or DNA species in the sample.

xi. Luminex

The Luminex technology allows the quantitation of nucleic acid products immobilized on color coded microspheres. The magnitude of the biomolecular reaction is measured using a second molecule called a reporter. The reporter molecule signals the extent of the reaction by attaching to the molecules on the microspheres. As both the microspheres and the reporter molecules are color coded, digital signal processing allows the translation of signals into real-time, quantitative data for each reaction.

8. Identification Methods

Amplification products must be visualized in order to confirm amplification of the target-gene(s) sequences. One typical visualization method involves staining of a gel with for example, a flourescent dye, such as ethidium bromide or Vistra Green and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly, using a nucleic acid probe. Following separation of amplification products, a labeled, nucleic acid probe is brought into contact with the amplified gene(s) sequence. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ and Molecular Beacon™ probes. In still other embodiments, solid-phase capture methods combined with a standard probe may be used as well.

The type of label incorporated in PCR™ products is dictated by the method used for analysis. When using capillary electrophoresis, microfluidic electrophoresis, HPLC, or LC separations, either incorporated or intercalated fluorescent dyes are used to label and detect the PCR™ products. Samples are detected dynamically, in that fluorescence is quantitated as a labeled species moves past the detector. If any electrophoretic method, BPLC, or LC is used for separation, products can be detected by absorption of UV light, a property inherent to DNA and therefore not requiring addition of a label. If polyacrylamide gel or slab gel electrophoresis is used, primers for the PCR™ can be labeled with a fluorophore, a chromophore or a radioisotope, or by associated enzymatic reaction. Enzymatic detection involves binding an enzyme to primer, e.g., via a biotin:avidin interaction, following separation of PCR™ products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If PCR™ products are separated using a mass spectrometer no label is required because nucleic acids are detected directly.

A number of the above separation platforms can be coupled to achieve separations based on two different properties. For example, some of the PCR™ primers can be coupled with a moiety that allows affinity capture, and some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affmity chromatography column. The flow-through fraction is collected, and the bound fraction eluted (by chemical cleavage, salt elution, etc.). Each sample is then further fractionated based on a property, such as mass, to identify individual components.

9. Analysis of Data

Gathering data from the various analysis operations will typically be carried out using methods known in the arL For example, microcapillary arrays may be scanned using lasers to excite fluorescently labeled targets that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Scanning devices of this kind are described in U.S. Pat. Nos. 5,143,854 and 5,424,186.

Following the data gathering operation, the data will typically be reported to a data analysis operation. To facilitate the sample analysis operation, the data obtained by a reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like, as described in, eg., U.S. Pat. Nos. 4,683,194, 5,599,668 and 5,843,651 incorporated herein by reference.

10. Kits

The materials and reagents required for detecting and quantitating gene expression from a biological sample may be assembled together in a kit. The kits of the invention generally will comprise a set of restriction endonucleases used to digest the cDNA. Preferred kits will comprise frequent cutters such as four-base cutter, five base cutter or six base cutter restriction enzymes.

The kits of the invention also will generally comprise one or more preselected primer sets and/or probes that may be either specific or non-specific for the genes to be amplified. Preferably, the kits will comprise, in suitable container means, one or more nucleic acid probes and/or primer sets and means for detecting nucleic acids. In certain embodiments, such as in kits for use in amplification reactions, the means for detecting the nucleic acids may be a label, such as a fluorophore, a radiolabel, an enzyme tag, etc., that is linked to the nucleic acid primer or the nucleotides themselves. It is envisioned that kits may contain pairs of primers for standardization of gentags.

Preferred kits are those suitable for use in PCR™. In PCR™ kits, two primers will preferably be provided that have sequences from, and that hybridize to, spatially distinct regions of the target gene. Preferred pairs of primers will have two parts, a first subsequence, corresponding to a recognition-sequence of a four-base cutter and a second subsequence, corresponding to a specificity region designed to amplify any possible combination of nucleotides adjacent to the restriction site. Kits of this embodiment will be used to amplify all genes, unknown and/or known, that respond to certain treatments or stimuli. In other embodiments, the second subsequence following the restriction-enzyme sequence will correspond to a known gene or set of genes. The kits of this embodiment will be used to detect and quantitate all known genes that belong to a family or all known genes that respond to a treatment or stimulus. Other preferred pairs of primers for amplifying nucleic acids are selected to amplify the sequences specified herein. Also included in PCR™ kits may be enzymes suitable for amplifying nucleic acids, including various polymerases (RT, Taq, etc.), deoxynucleotides and buffers to provide the necessary reaction mixture for amplification.

The kits of the present invention, although containing at least one sequence corresponding to a restriction-enzyme recognition sequence, as disclosed herein, also may contain one or more of a variety of other target-gene sequences as described above. The kits of the present invention may also include the anchorable moiety, components necessary for second strand cDNA synthesis, linkers, ligase, and kinase.

In each case, the kits will preferably comprise distinct containers for each individual reagent and enzyme, as well as for each probe or primer pair. Each biological agent will generally be suitable aliquoted in their respective containers. The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

D. Differential Gene Expression Analyzed by COP

1. Description of the COP Technique

The details of the method are given in FIG. 1 using the cDNA for annexin III as an illustrative example. cDNA was synthesized with biotinylated oligo (dT) as first strand primer, digested with a frequent-cutting restriction endonuclease (DpnII), and the 3'-most fragment recovered by binding to a streptavidin-coated bead. To provide a common priming sequence, a 16-bp adapter with a DpnII compatible sticky end ("B-linker") was ligated onto the cDNA fragments. The fragments were then digested with a second frequent cutting restriction endonuclease, (NlaII) and a second common priming site ("A-linker") was added by ligation. This procedure resulted in a template preparation ("B/A genetags") that contained a single gene-specific target sequence from each cDNA, with common A and B linkers at the two ends. Because each of the two enzymes used has a recognition site on average every 256 bp, the average size of the gene-specific target sequences was expected to be about 128 bp. Thus, the sequence complexity of the genetag preparation was reduced by about 15-fold relative to the cDNA population, assuming an average mRNA size of about 2 kb.

The scheme illustrated in FIG. 1 will not produce an amplifiable genetag from cDNAs in which there is no NlaM restriction site between the last DpnII restriction site and the poly(A) tail. To prepare a template suitable for analysis of these cDNAs, a second preparation, A/B genetags, was made by reversing the order in which the DpnII and NlaIII cuts were made. cDNAs in which DpnII and NlaII restriction sites are absent or separated by less than 6 bp are refractory to this analysis; empirically this corresponds to about 5–10% of the transcriptome.

PCR™ reactions using primers containing only the A- and B-linker sequences would be expected to amplify all of the gene-specific targets in these genetag preparations. To provide specificity to the PCR™ reactions, COP primers were constructed containing the A-linker sequence (16 nt) followed by 4 variable nt (256 different primers) or the B-linker sequence (16 nt) followed by 3 variable nt (64 different primers). These primers can be combined pairwise with the two orientations of genetags to produce (256×64×2)=32,768 unique reactions. The presence of relatively long common regions in the COP primers allows near optimal amplification with all primers under a single set of PCR™ conditions. For cDNAs of known sequence, a single pair of primers that will amplify the gene-specific target in one genetag orientation can be predicted from the sequence, as well as the size of the resulting fragment (amplimer). Current estimates of the number of genes in the human transcriptome range from about 60,000 to 100,000. Since the COP method effectively divides the transcriptome randomly among 32,768 unique reactions, each pair of COP primers tested may give several amplimers (2–3 on average), only one of which corresponds to the gene being assayed. In general, these amplimers can be distinguished by size.

2. Specificity Of COP

As an example of the specificity of the method, reactions were performed with primers predicted to produce a 291 bp amplimer from the murine Brca1 gene. As template for these reactions, mRNA was prepared from cultures of mouse keratinocytes. Epidermal keratinocyte cultures were derived from newborn mice and maintained as described, Pierce et al., 1998a. Total RNA was prepared by extraction into a chaotropic salt solution and organic solvent extraction using either a QIAGEN (Valencia, Calif.). mRNA was prepared using a QIAGEN kit, and double-stranded cDNA was synthesized using a GIBCO/BRL kit but substituting biotinylated $p(dT)_{18}$ as the primer for first strand synthesis. Double stranded linkers with overhangs complementary to the ends created by restriction with Nla III (A-linker) and Dpn II (B-linker) were prepared separately by mixing equal amounts of the following oligonucleotides, warming to 90° C. for 2 min and slowly cooling to room temperature: A-linker—5'-CGTCTAGACAGC (previously phosphorylated with T4 polynucleotide kinase) and 5'- GCTGTCTA-GACGCATG; B-linker—5'-CGGTGATGCATC and 5'-GATCGATGCATCACCG (previously phosphorylated with T4 polynucleotide kinase).

cDNA (1.5 µg) was digested with Dpn II, the 3'-most Dpn II fragment of each cDNA was absorbed to streptavidin/magnetic beads (Dynal, Lake Success, N.Y.) and non-biotinylated fragments were removed. B-linker (217 ng) was added to the cDNA fragments bound to the beads, warmed to 50° C. for 2 min, cooled to room temperature for 15 min, then cooled on ice. Ligation was accomplished by adding 10 U T4 DNA ligase (GIBCO/BRL) and incubating in a fmal volume of 50 µL for 2 hr at 16° C. The preparation was then digested with NlaIII, and fragments released from the beads were recovered and ligated to the A-linker (217 ng) under similar conditions. These fragments of cDNA, containing the gene-specific targets ligated to the B and A linkers, are referred to as B/A genetags. A second preparation, A/B genetags, was obtained by performing Nla III restriction and A-linker ligation prior to Dpn II restriction and B-linker ligation.

To test the selectivity of the method, two pairs of primers that differed by a single nucleotide from the Brca1 primers were also chosen that were expected to produce amplimers of 117 and 197 bp from the genes for annexin III and an anonymous cDNA (clone 2C11B), respectively. Two sets of primers for COP PCR™ reactions were synthesized, corresponding to the A- and B-linkers above, but containing 3 or 4 nucleotide specificity regions at the 3' end. The sequences of these primer sets were:

A-end (256 primers)-5'-GCGTCTAGACGCATGNNNN;
B-end (64 primers)-5'-CGGTGATGCATCGATCNN.

PCR™ reactions contained (total volume, 25 µL) genetags equivalent to 0.1 to 4 ng cDNA, 40 pg of each COP primer, 0.25 µL AmpliTaq (Perkin Elmer Co.) and 1×"D" buffer (Epicentre Technologies, Madison Wis.). Reactions were run in a Stratagene RoboCycler with an initial denaturation of 5 min at 95° C., 2 min at 60° C. and 1 min at 72° C. followed by 26 cycles of 0.5 min at 95° C., 1 min at 60° C. and 1 min at 72° C. The final extension at 72° C. was increased to 6 min. After addition of 1/10 vol 10×sample buffer (7.0 M urea, 0.4% bromphenol blue, 50 mM Tris, 20 mM EDTA, pH 7.5), portions of the reactions were analyzed by electrophoresis on 8% polyacrylamide gels. DNA fragments were stained with Vistra Green (Molecular Probes, Eugene, Oreg.) and digitized fluorescent images were obtained with a FluorImager (Molecular Dynamics, Sunnyvale, Calif.). A relative measure of the amount of product in each of the bands ("amplimers") seen on the gel image was obtained by densitometry, using the volume integration facility of the ImageQuant software supplied with the FluorImager.

Figure 2A:
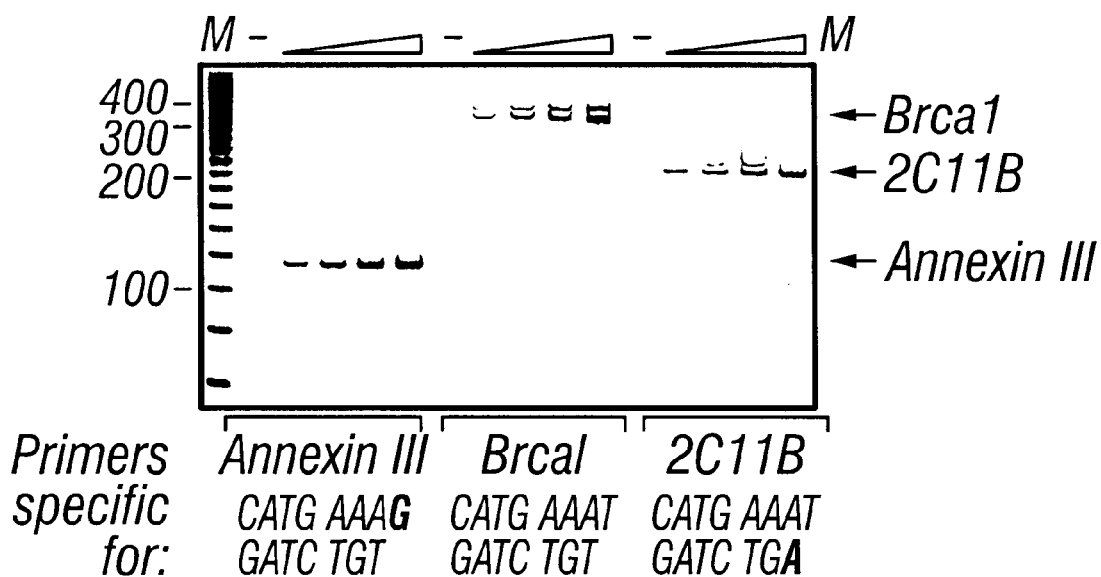
Figure 2B:
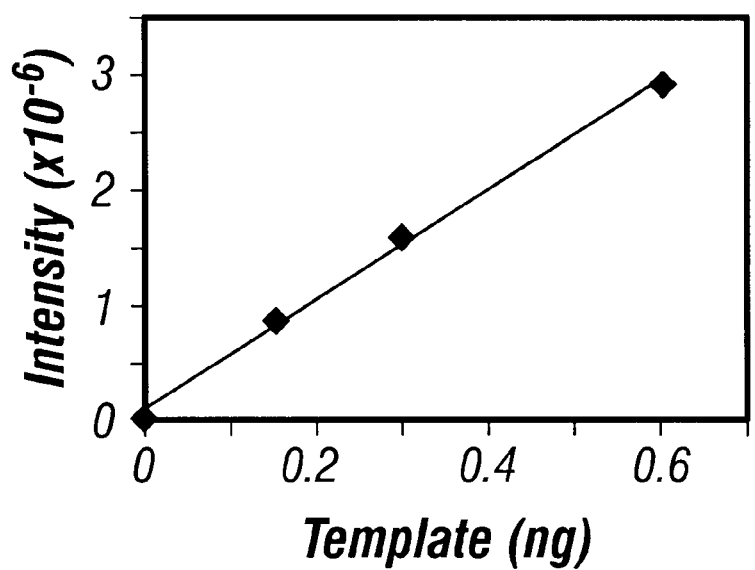
Figure 2C:
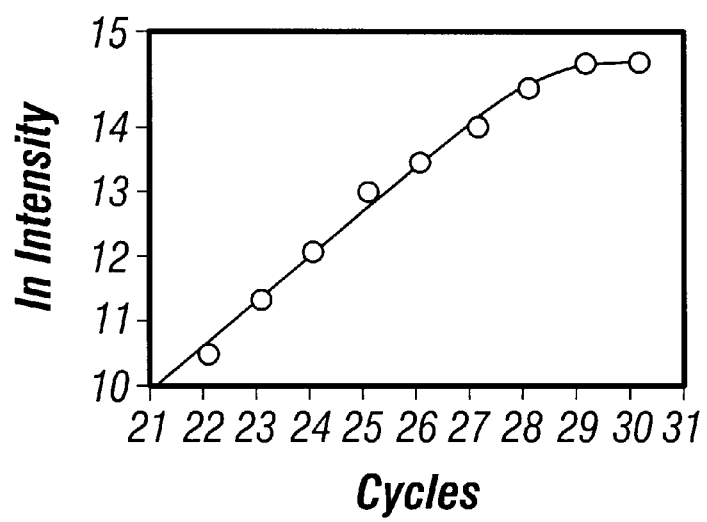
Figure 2D:
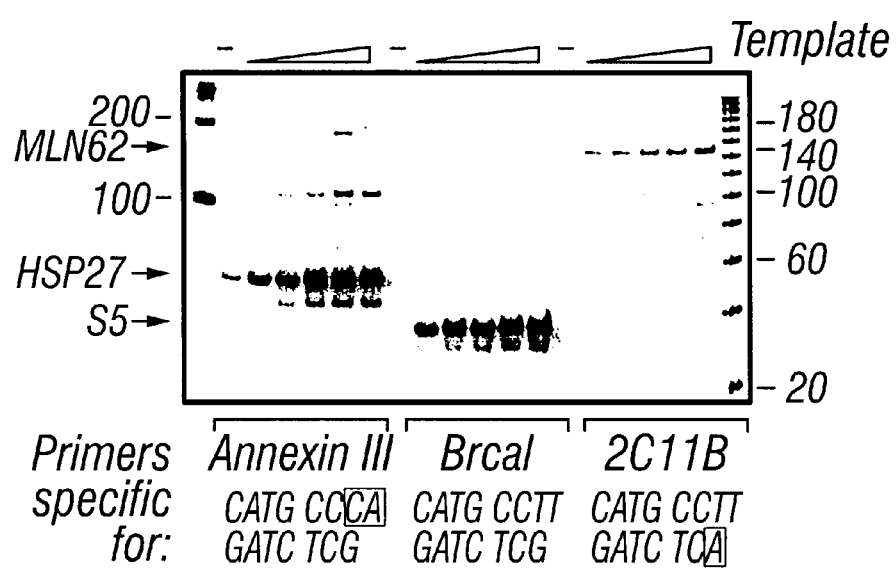

An amplimer of the expected size was produced in PCR™ reactions with each of these three pairs of primers (FIG. 2A), and in each case the expected amplimer was the major product. Significantly, production of the Brca1-specific amplimer was not detected in reactions designed to amplify annexin III or 2C11B, and vice versa. A similar experiment was carried out using the COP primers predicted for 3 human genes, HSP27, RPS5, and MLN62, with genetags prepared from the human breast cancer cell line SKBR3. SKBR3 human breast tumor cells were grown in DMEM containing 10% fetal bovine serum. Cell monolayers were rinsed with saline, and RNA isolated as described above for keratinocytes. Again the primers selectively gave rise to amplimers of the expected sizes (FIG. 2D), in each case the expected amplimer was the major product, and the HSP27-specific product was not obtained in reactions designed to amplify RPS5 and MLN62 and vice versa To verify that the products were indeed those expected, the 291 bp amplimer obtained with primers specific for the Brca1 gene (see FIG. 2A) was gel-purified and sequenced in both directions with the same primers used in the initial reaction; the experimentally determined sequence exactly matched the predicted sequence. To further validate the specificity of COP reactions, primer pairs were selected for 9 other murine genes, including several high abundance, housekeeping genes, Odc, Rp15, and Actg, and also lower abundance genes, Mdm2, Ccng, Cdkn2a, Cdk7 and transcription factors Yy1 and Hfh2. Similarly, primer pairs were selected for 14 human genes: HSPB1(the gene for HSP27), TRAF4 (the gene for MLN62), RPS5, RPS16, RPL31, CAPN4, XPC, IGFBP2 ARF3, PSMD12, CREB2 TOP3, TCEB3, ETR101. Reactions were run with the appropriate primer pairs and genetag templates, reaction products of the expected size were again gel-purified and sequenced, and in each case the sequence obtained was greater than 95% identical to the expected product 3. Quantitation with COP There are two major requirements that must be met to obtain quantitative data from PCR™ reactions: the signal must increase linearly with the amount of template and the PCR™ reactions must be in the exponential phase rather than the stationary phase, i.e. the signal must increase exponentially with cycle number. Densitometry of the stained gel shown in FIG. 2A indicated that the integrated intensity of the amplimer bands increased linearly with the amount of genetag template up to about 0.6 ng cDNA for annexin III and up to about 4 ng cDNA for Brca1 and 2C11B (FIG. 2B). In addition, when the number of PCR™ cycles was varied, the integrated intensities increased exponentially with increasing cycle number from 22 to 28 (FIG. 2C). Similarly for the experiment with human genes shown in FIG. 2D, the intensity of the bands increased linearly with template concentration over a defined range, and exponentially with PCR™ cycle number from 24 to 28 cycles.

To assess the reproducibility of the technique, replicate genetag preparations were assayed for the expression of three representative genes that displayed a wide range of expression. Four samples of A/B genetags were prepared independently from a single cDNA preparation from SKBR3 cells, and quadruplicate reactions were carried out using 3 non-overlapping pairs of COP primers specific for the small subunit of calpain (FIG. 3A), MLN62 (FIG. 3B), or the gene for the p55 component of the proteasome (FIG. 3C). The amplimers expected in these reactions, as well as 2 unidentified products of approximate lengths 76 and 130 bp seen in FIG. 3A, were quantitated. Although the relative expression levels for this group of amplimers varied over a 25-fold range, the overall coefficients of variation were all between 0.23 and 0.27. Analysis of these data by multiple ANOVA indicated that the overall dispersion is due to variance in repeated PCR™ measurements of a single genetag preparation, and to differences between the genetag preparations. By performing multiple analyses on selected genes of interest, statistical significance can be attained for changes in gene expression that extend below the 2-fold level . Power calculations (assuming a lognormal distribution of the ratio data) indicate that with a minimum of 4 observations, a two-fold difference in the expression ratio can be detected with a power of 95%. This power is similar to that of other techniques for differential gene expression analysis as is well known in the art.

4. Quantitation by competitive RT-PCR

However, it is widely felt that the ultimate quantitative method for PCR™ determination of mRNA levels is competitive RT-PCR™. In this technique, for each target gene that is analyzed, a competitive template must be made that is amplified by the same primers with approximately the same efficiency as the target. By co-amplifying a constant amount of unknown cDNA with different known amounts of the competitive template the concentration of the unknown target cDNA can be accurately evaluated. Generally, the competitive template is engineered to contain the same sequences as the target, with a small insertion or mutation built in that allows the products derived from the target and the competitor to be distinguished, either by size or by sensitivity to digestion by one or more restriction enzyme. Typically, a large amount of time and effort is expended to design, produce and validate the competitive template. In the present invention, the inventors have designed a general strategy for the production of competitive templates for target genes of known sequence using COP. A specific example of this strategy is outlined in FIG. 4, using the gene for HSP27 for illustration. The COP genetag sequence for HSP27 and the associated COP primers (COP32 and COP46) are shown in the center of FIG. 4. The inventors synthesized a primer (CRT004) that contains the COP32 sequence and 5 or more nucleotides of the target genetag sequence ("clamp"). Between the COP32 and clamp sequences the inventors inserted 5 bp of arbitrary sequence, in this case ACACA. When a PCR™ reaction was run using CRT004 and COP 46 as primers and a genetag preparation from SKBR3 cells known to contain the HSP27 target as the template, an amplimer was produced in high yield that contained the same sequences as the HSP27 genetag but with the insertion of 5 bp (ACACA). This was verified by direct sequencing. This amplimer, identified in FIG. 4 as CRT 32/46, was purified from polyacrylamide gels, quantitated by the PicoGreen assay, and used as a competitive template in reactions with COP32 and COP46 as primers and SKBR3 genetags as unknown template. As shown in FIG. 5, the target product obtained in the absence of competitor (lane 2) was easily distinguished from the 5 bp longer product obtained from the competitive template in the absence of genetags (lane 11). When increasing amounts of competitor were added to a constant amount of genetags (FIG. 5: lanes 3 through 10), the intensity of the longer band increased linearly. When the two bands are of equal intensity, the concentrations of the target genetag and the competitor are considered to be equal. This equivalence point can be estimated from linear plots of the ratio of the intensities of the two bands versus the concentration of competitor. However, some authorities recommend using log-log plots of the data to verify that the reactions are within the required parameters. Such plots should be linear with a slope of approximately 1. As shown in FIG. 6, the competitive log-log plot for the HSP27 assay is linear with a slope of 1 around the equivalence point. Note also that the assay is extremely sensitive—the equivalence point corresponds to the addition of 0.042 fg of competitive template to the PCR™ reaction. The inventors have also used this strategy for the preparation of a competitive RT-PCR™ assay for MLN62, but in this case the target amplimer was 153 bp and a 10 bp insert was introduced. Again, log-log plots were linear with a slope of about 1.

5. Sensitivity of COP analysis

To assess the sensitivity of the technique, an internal control template for the MLN62 gene ($IC_{MLN62}$) was constructed using methods analogous to those described in the previous section. This template contained (FIG. 7A) the gene-specific target for the MLN62 gene with a 10 bp insertion, the A-end and B-end linkers, and a biotin label at one end. As expected, amplification of this template with MLN62-specific COP primers gave rise to a product 10 bp longer than the MNL62-specific amplimer (FIG. 7B, lane 6, arrowheads). A normal human mammary epithelial cell line, HME87 (Gazdar et al., 1998), was grown in serum-free medium (MEGM, Clonetics, Walkersville, Md.) and cDNA was prepared as described above for SKBR3 cells.

The $IC_{MLN62}$ DNA was mixed with cDNA prepared from HME87 normal human mammary epithelial cells at a 1:20,000 weight ratio, and A/B genetags were prepared. PCR™ reactions were performed using the MLN-specific COP primers, and amplimers corresponding in size to the MLN62 cDNA (closed arrowhead) and to the $IC_{MLN62}$ (open arrowhead) were obtained (FIG. 7B, lanes 2–5). The intensity of both bands increased linearly with template concentration (FIG. 7C). From the ratio of intensities of these two bands in FIG. 7B and the known level of addition of the $IC_{MLN62}$ to the cDNA, the molar concentration of the endogenous MLN62-specific genetag could be calculated as 0.6 amol/ng cDNA. Assuming an average mRNA length of 2000 nt this corresponded to an mRNA abundance of ~0.07%. Expression levels at least 8-fold lower than that of MLN62 can easily be detected in this system (compare MLN62 with p55, FIG. 3), suggesting that the lower limit of detectability is less than 0.01% or about 30 molecules of mRNA per cell.

6. Standardization

One method by which COP experiments can be normalized is by the use of sets of control or standardization genes. This method uses essentially an external standard approach. A set of genes is identified whose expression is relatively constant among different biological samples. These are usually comprised of "housekeeping" genes, such as ribosomal protein genes and genes for intermediary metabolic enzymes. COP amplifications for these genes are performed in parallel with COP amplification for the genes of interest, and the results compared. Tables 4 and 5 give examples of sets of standardization genes for both orientations of human and mouse genetags, respectively.

TABLE 4

HUMAN STANDARDIZATION GENE SET FOR RAGE

| GENE | ACCESSION # | ORIENT | SIZE | Primer A | Primer B |
|---|---|---|---|---|---|
| MALIC ENZYME | M55905 | B/A | 570 | 185 | 314 |
| L3 | X06323 | B/A | 261 | 264 | 46 |
| S7 | M77233 | B/A | 278 | 170 | 323 |
| L35 | U12465 | B/A | 160 | 174 | 304 |
| S28 | U14973 | B/A | 158 | 218 | 306 |
| L8 | 728407 | B/A | 153 | 212 | 307 |
| S15a | X84407 | B/A | 136 | 118 | 67 |
| S26 | X69654 | B/A | 110 | 194 | 46 |
| S27 | U57847 | B/A | 108 | 88 | 45 |
| PHOSPHOGLYCERATE MUTASE | J04173 | B/A | 102 | 78 | 67 |
| PHOSPHOFRUCTOKINASE | D25238 | B/A | 211 | 103 | 289 |
| CYTOKERATIN | X98614 | B/A | 248 | 64 | 70 |

TABLE 4-continued

HUMAN STANDARDIZATION GENE SET
FOR RAGE

| GENE | ACCESSION # | ORIENT | SIZE | Primer A | Primer B |
|---|---|---|---|---|---|
| | | | 156 | | |
| | | | 200 | | |
| | | | 675 | | |
| LAMIN A | M13452 | B/A | 157 | 65 | 23 |
| BETA ACTIN | X00351 | B/A | 163 | 28 | 67 |
| | | | 34 | | |
| | | | 92 | | |
| C/EBP/epsilon | U48866 | B/A | 318 | 186 | 47 |
| | | | 220 | | |
| CYTOKERATIN 18 | X12883 | B/A | 103 | 59 | 69 |
| | | | 190 | | |
| | | | 270 | | |
| | | | 350 | | |
| NUCLEOPHOSMIN | M23613 | B/A | 314 | 248 | 47 |
| | | | 220 | | |
| | | | 190 | 186 | 290 |
| L23 | X53777 | NB | 55 | 100 | 68 |
| L23a | U37230 | NB | 232 | 85 | 300 |
| | | | 68 | | |
| | | | 315 | | |
| P0 | M17885 | NB | 311 | 161 | 67 |
| | | | 96 | 161 | 67 |
| | | | 110 | 161 | 67 |
| | | | 750 | 161 | 67 |
| L10 | L25899 | NB | 175 | 214 | 285 |
| L31 | X69181 | NB | 253 | 87 | 67 |
| | | | 171 | | |
| | | | 118 | | |
| | | | 63 | | |
| S11 | X06617 | NB | 67 | 248 | 23 |
| | | | 103 | | |
| | | | 127 | | |
| | | | 197 | | |
| L6 | X69391 | NB | 277 | 223 | 290 |
| S18 | X69150 | NB | 105 | 261 | 286 |
| | | | 73 | | |
| L12 | L06505 | NB | 108 | 8 | 310 |
| L26 | X69392 | NB | 241 | 32 | 332 |
| | | | 120 | | |
| L19 | X63527 | NB | 163 | 49 | 45 |
| L30 | M94314 | NB | 64 | 87 | 331 |
| | | | 119 | | |
| TRANSKETOLASE | U55017 | NB | 122 | 178 | 330 |
| | | | 75 | | |
| PHOSPHOGLYCERATE KINASE | V00572 | NB | 77 | 48 | 68 |
| | | | 120 | | |
| | | | 200 | | |
| | | | 345 | | |
| S6 | M20020 | NB | 596 | 178 | 329 |
| | | | 160 | | |
| S16 | M60854 | NB | 349 | 39 | 45 |
| | | | 900 | | |
| | | | 295 | | |
| | | | 170 | | |
| | | | 130 | | |
| | | | 98 | | |

TABLE 5

MOUSE STANDARDIZATION GENE SET
FOR COP

| GENE | ACCESSION # | ORIENT | SIZE | Primer A | Primer B |
|---|---|---|---|---|---|
| RPL8 | U67771 | B/A | 304 | 65 | 323 |
| S26 | U67770 | B/A | 110 | 194 | 302 |
| P1 | U29402 | B/A | 268 | 237 | 285 |
| L36 | X75895 | B/A | 70 | 185 | 306 |
| S4 | M73436 | B/A | 132 | 247 | 47 |
| S14 | Y08307 | B/A | 114 | 186 | 332 |

TABLE 5-continued

MOUSE STANDARDIZATION GENE SET FOR COP

| GENE | ACCESSION # | ORIENT | SIZE | Primer A | Primer B |
|---|---|---|---|---|---|
| S12 | Y11682 | B/A | 153 | 54 | 310 |
| L12 | L04280 | B/A | 80 | 103 | 71 |
| L3 | Y00225 | A/B | 68 | 58 | 332 |
| L29 | X05021 | A/B | 43 | 130 | 71 |
| P0 | X15267 | A/B | 61 | 165 | 67 |
| S24 | X60289 | A/B | 170 | 179 | 326 |
| A52 | U28917 | A/B | 103 | 110 | 331 |
| S11 | U93864 | A/B | 67 | 248 | 24 |
| S28 | U11248 | A/B | 185 | 62 | 295 |
| L29 | L08651 | A/B | 295 | 65 | 331 |
| S24 | X60289 | A/B | 170 | 179 | 326 |

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Use of COP for the Determining the Global Expression of Genes from the SKBR3 Cell-Line To develop the COP concept experimentally, the inventors used a human breast cancer cell line, SKBR3, for which global gene expression data had been previously obtained using the SAGE technique. Four genes, known to be expressed in SKBR3 cells on the basis of SAGE studies, were chosen for initial tests. The mRNA sequences for these genes were obtained from GenBank and analyzed to design COP primers. FIG. 8 shows a portion of the sequence of one of these genes, MLN62, and the location of the COP primers, and Table 6 shows the four genes chosen; their approximate expression levels from the SAGE data; the COP primers; and the lengths of the amplimers expected. Poly A(+)RNA was prepared from SKBR3 cells, and a genetag preparation with A/B orientation was made using the enzymes NlaIII and Dpn II PCR™ reactions (25 µL) were set up using the required primers and genetags were derived from 1.0 ng of cDNA per reaction. Aliquots of the PCR™ products were analyzed on 5% polyacrylamide gels and visualized by ethidium bromide staining. The results are shown in FIG. 9. For each pair of primers, reactions that lacked template gave no visible products. In the presence of the genetag template, each pair of primers produced a well-defined band ("amplimer") that matched the size expected for the corresponding gene. Although the primer pairs used differed from each other by 1, 2 or 3 nucleotides, in no case did a primer pair produce an amplimer that matched in size the amplimer expected from a different primer pair in this set (compare, for example, FIG. 9: lanes 5 and 6 with lanes 9 and 10). In some cases (for example, FIG. 9: lanes 9 and 10) one or more amplimers that did not match the expected size were also seen. This is not unexpected, since on the average each COP primer pair should amplify a unique fragment from 3–4 different genes, and these fragments are likely to be of different sizes. The identity of the 100 bp fragment seen in lanes 9 and 10 is currently unknown. For each of the four genes tested in this study, the amplimer band was excised from the gel, purified and sequenced. In all cases, the derived sequence matched the expected sequence. In Table 7 the inventors list 10 genes that have been tested to date and for which COP produces an amplimer of the expected size and sequence.

TABLE 6

GENES ANALYZED IN SKBR3 CELLS BY COP

| GENE | EXPRESSION LEVEL (%) | PRIMER A | PRIMER B | AMPLIMER LENGTH (BP) |
|---|---|---|---|---|
| RPS16 | 0.38 | CATGCCGT | GATCTCC | 351 |
| RPS5 | 0.19 | CATGCCTT | GATCTCG | 41 |
| HSP27 | 0.16 | CATGCCCA | GATCTCG | 60 |
| MLN62 | 0.03 | CATGCCTT | GATCTCA | 150 |

Expression level was determined in SKBR3 cells by SAGE analysis. Only the specificity regions of the A and B primers are listed.

TABLE 7

VALIDATION of COP SPECIFICITY

| Gene Description | Accession | Matches/Positions |
|---|---|---|
| γ-actin | M20826 | 69/69 |
| RPL5 | Z35311 | 106/106 |
| CDK7 | U11822 | 347/349 |
| Brca1 | U36475 | 267/267 |
| P19$^{ARF}$ | L76092 | 479/484 |
| MDM2 | U47934 | 61/61 |
| ODC | M12331 | 177/178 |
| Cyclin G | Z37110 | 85/85 |
| YY-1 | M73963 | 223/224 |
| Genesis | U41047 | 230/230 |

Quantitation with COP

The data shown above indicates that the amount of amplimer produced from a given template with a given pair of primers is fairly reproducible, specific and can be detected with a low background noise. Several other requirements must be met in order for the COP results to be considered quantitative reflections of the abundance of a given mRNA in the population. The literature on quantitative PCR™ yields two main prerequisites: the reactions must be analyzed during the exponential phase of the PCR™, and the amount of amplimer produced must be directly proportional to the concentration of template. To test these requirements, the inventors performed PCR™ reactions with SKBR3 genetags as the template and a combination of three COP primers that produced three strong amplimers, under varying number of cycles and varying template concentrations. Reaction products were analyzed as described above, except that staining was done with VistraGreen to obtain slightly better sensitivity. The stained gel was analyzed on a Fluorlmager (Molecular Dynamics) and the relevant bands were quantitated using ImageQuant software.

Results obtained when the number of PCR™ cycles were varied from 24 through 28 are shown in FIG. 10 and FIG. 11. For all three bands, an exponential increase in the amount of the amplimer was seen for at least the 25th through the 27th cycle. Results obtained when the template concentration were varied from 0.1 to 1.0 ng are shown in FIG. 12 and FIG. 13. For all three bands, the amount of amplimer produced increased linearly with template over this range. These studies demonstrate that COP is a quantitative procedure.

Informatics

The inventors have developed several kinds of bioinformatics tools needed to support the implementation of the methods described herein (FIG. 21). First they have developed several software programs that run on Macintosh digital computers. These include (1) a program to find the correct amplification primers for any given mRNA accession in GenBank; (2) a program to find all GenBank mRNA accessions that should be amplified from a suitable genetags preparation by a particular pair of amplification primers; (3) a program that analyzes and summarizes quantitative data obtained from COP experiments.

Second, they have constructed relational databases using commercially available software (Helix Express, FileMaker Pro) that support the design, execution and analysis of COP experiments. The first of these contains all mRNA sequence accessions from GenBank; databases have been created and are maintained for data from human, mouse and rat accessions. In formation on the identity and positions of the correct amplification primers for the mRNA, the length and sequence of the expected product, the positions of the coding sequence and the polya signal(s), and links to other databases are stored in the database. In addition, project-specific, laboratory information on cDNA preparations, genetag preparations, PCR reactions run and analyzed, and experimental data recorded can be stored and retrieved. Finally, experimentally observed amplimers can be compared to all possible amplimers predicted from the GenBank accession data, and matched on the basis of primer sequence, genetag orientation a aintaplimer length.

Example 2
Differential Gene Expression in K5E2F1 Transgenic Mice

The COP technique is envisioned to have wide applications, both as a screening tool and as a low-ost adjunct to other global gene expression technologies. In this example the inventors demonstrate the use of this technology to study changes in gene expression. Changes in expression levels of genes in transgenic mouse keratinocytes overexpressing the human E2F1 gene, including the upregulation of several genes that act to increase p53 activity were determined using COP. Two genes not previously reported to be regulated by E2F1: Brca1 and CDK7, were also found to have an increased expression.

Overexpression of the cell cycle-regulated transcription factor E2F1 can bypass growth arrest induced by a variety of methods. This is due to the ability of E2F1 to transactivate genes important for cell cycle progression, including genes for DNA biosynthetic enzymes, factors that control the initiation of DNA synthesis, cell cycle regulators, and several protooncogenes (Johnson and Schneider-Broussard, 1998; Slansky and Farnham, 1996). In contrast to its positive effects on cell growth, E2F1 has also been shown to have a role in apoptosis in some systems. It has recently been reported that E2F1 mediates the induction of apoptosis by several oncoproteins, and this effect is mediated by stabilization of p53, in part by an induction of p19$^{ARF}$ (Zindy et al., 1998; deStanchina et al., 1998; Bates et al., 1998). In other systems, however, p53 is not involved in the apoptotic response to E2F1, and in fact the transactivation domain of E2F1 may be dispensable (Phillips et al., 1997; Hsieh et al., 1997). Thus, it is not clear to what extent activation, derepression or repression of downstream target genes is involved in E2F1-mediated apoptosis.

The inventors recently described the generation of transgenic mice expressing E2F1 under the control of a keratin 5 (K5) promoter (Pierce et al., 1998a; Pierce et al., 1998b). Deregulated expression of E2F1 in basal keratinocytes results in epidermal hyperplasia, hyperproliferation and aberrant p53-dependent apoptosis. In the absence of functional p53, E2F1-induced apoptosis is significantly reduced while E2F1-induced hyperproliferation is unchanged. Significantly, K5 E2F1 transgenic mice that are deficient (heterozygous or nullizygous) for p53 develop spontaneous skin carcinomas. The inventors previously demonstrated that K5 E2F1 keratinocytes overexpress at least one endogenous E2F target, the cyclin E gene. To further explore the molecular mechanisms underlying the phenotype of these transgenic mice, the inventors applied the COP technology to determine in further detail changes in endogenous gene expression resulting from overexpression of the K5 E2F1 transgene.

The method developed herein allows expression changes to be determined in about 90% of the transcriptome in either a directed search of known genes, or an undirected survey of unknown genes. Unique, gene-specific targets are prepared from each cDNA by digestion with two restriction nucleases and poly(A) selection, ligated to common primer binding sites, and amplified by PCR™. The primers contain a common region, derived from the linker, plus a 3'-specificity region of 3 or 4 nucleotides, allowing them to selectively amplify cDNAs from a small number of genes. For known genes, the identity of the cDNA amplified can be deduced from the sequence of the primers and the length of the amplimer produced. The intensity of the amplimer band on the gel is a relative measure of the frequency of the corresponding mRNA in the total population of mRNAs. As in other forms of RT-PCR analysis, proportionality is expected under conditions where the intensity of the signal increases linearly with increasing template concentration and exponentially with the number of cycles.

The details of the method for preparing genetags are shown in FIG. 1 using the cDNA for annexin m as an illustrative example. The gene-specific targets are partially purified by cutting cDNA with one restriction enzyme, selecting the poly(A)-containing, 3'-most fragment, and then cutting with a second restriction enzyme. By ligating two different linkers (A and B) to the sticky ends produced by the restriction enzymes, only fragments containing the gene-specific target will contain both A and B linkers. The inventors call these fragments "genetags". This ensures that each cDNA molecule will give rise to only one "genetag", reducing the sequence complexity of the template population by an order of magnitude.

Preparation of GenetagTemplates cDNA was synthesized using biotinylated-(dT)$_{18}$ as the primer for first strand synthesis. Mice transgenic for the human E2F-1 gene, under the control of the bovine keratin 5 promoter, were maintained as heterozygotes. Epidermal keratinocyte cultures were derived from newborn mice carrying the transgene or from their wild type siblings as described. Total RNA was prepared by extraction into a chaotropic salt solution followed by organic solvent extraction using either a QIAGEN (Valencia, Calif.) or a GIBCO/BRL (Gaithersburg, Md.) kit. Total RNA was used directly for Northern analyses. Alternatively, mRNA was prepared using a QIAGEN kit, and double-stranded cDNA was synthesized using biotinylated p(dT)$_{18}$ as the primer for the first strand synthesis. cDNA was digested with Dpn II, the 3'-most Dpn II fragment of each cDNA was adsorbed to magnetic beads coated with streptavidin (Dynal, Lake Success, N.Y.) and non-biotinylated fragments were washed from the beads. cDNA fragments still bound to the beads were ligated to the B-inker, then digested with Nla III; and fragments released from the beads by this treatment were selected and ligated to the A-linker. Double stranded linkers with overhangs complementary to the ends created by restriction with Nla III (A-linker) and Dpn II (B-linker) were prepared separately by mixing equal amounts of the following oligonucleotides: warming to 90° C. for 2 min and slowly cooling to room temperature: A-linker—5'-CGTCTAGACAGC (previously phosphorylated with T4 polynucleotide kinase) and 5'-GCTGTCTAGACGCATG; B-inker—5'-CGGTGATGCATC and 5'-GATCGATGCATCACCG (previously phosphorylated with T4 polynucleotide kinase). Linkers (217 ng) were added to restricted cDNA fragments (initially 1.5 μg), warmed to 50° C. for 2 min, cooled to room temperature for 15 min, then cooled on ice. Ligation was accomplished by adding 10 U T4 DNA ligase (GIBCO/BRL) and incubating in a fmal volume of 50 μL for 2 h at 16° C. These fragments of cDNA, containing the gene-specific targets ligated to the B and A linkers, are referred to as B/A genetags. A second preparation, A/B genetags, is obtained when Nla III restriction and A-linker ligation preceded the Dpn II restriction and B-linker ligation. Also refer to FIG. 1.

The average gene specific target length is 128 bp, less than one-tenth the average mRNA length (2000 ntd). The scheme illustrated in FIG. 1 will not produce an amplifiable genetag from cDNAs in which there is no Nla III restriction site between the last Dpn II restriction site and the poly(A) tail. To analyze those genes, the inventors simply reverse the order in which the Dpn II and Nla III cuts are made. cDNAs that lack one or both enzyme recognition sites or in which the restriction sites are separated by less than 6 bp are refractory to this analysis. The inventors empirically found that this corresponds to about 5–10% of the transcriptome. To provide more specificity to the PCR™ reactions, COP primers were constructed containing the A-linker sequence (17 nucleotides) followed by 4 variable nucleotides (256 different primers) or the B-linker sequence (16 nucleotides) followed by 3 variable nucleotides (64 different primers). These primers can be combined pair-wise with the two orientations of genetags to produce (256×64×2)=32,768 unique reactions. The presence of relatively long common regions in the COP primers allows near optimal amplification with all primers under a single set of PCR™ conditions. PCR™ reactions contained (in a total volume of 25 μL): genetags equivalent to 0.1 to 2 ng cDNA; 40 pg of each primer, 0.25 μL AmpliTaq (Perkin Elmer Co.); and 1×"D" buffer (Epicentre Technologies, Madison Wis.). Reactions were run in a Stratagene RoboCycler with an initial denaturation of 5 min at 95° C., 2 min at 60° C. and 1 min at 72° C. followed by 26 cycles of 0.5 min at 95° C. 1 min at 60° C. and 1 min at 72° C. The final extension at 72° C. was increased to 6 min. For cDNAs of known sequence, a single pair of primers that will amplify the gene-specific target in one genetag orientation can be predicted from the sequence.

Specificity of COP is demonstrated herein with examples of the genes Brca1, annexin III and 2C11B. As shown in FIG. 14, along the bottom of the gel, primers specific for Brca1 (GenBank Accession No. U36475), annexin III (AJ001633), or 2C11B (U011139) were combined with B/A genetags and PCR™ amplification carried out for 27 cycles. PCR™ reactions contained (in a total volume of 25 μL): genetags equivalent to 0.1 to 2 ng cDNA, 40 pg of each primer, 0.25 μL AmpliTaq (Perkin Elmer Co.) and 1×"D" buffer (Epicentre Technologies, Madison Wis.). Reactions were run in a Stratagene RoboCycler with an initial denaturation of 5 min at 95° C., 2 min at 60° C. and 1 min at 72° C. followed by 26 cycles of 0.5 min at 95° C., 1 min at 60° C. and 1 min at 72° C. The final extension at 72° C. was increased to 6 min. The reactions were analyzed on 8% polyacrylamide gels, stained with Vistra Green (Molecular Probes, Eugene, Oreg.) and digitized fluorescent images were obtained with a FluorImager (Molecular Dynamics, Sunnyvale, Calif.). Arrows to the right indicate the expected molecular sizes of the three amplimers. Wedges above the lanes indicate increasing concentrations of template in the reactions (0.15 to 1.2 ng cDNA for annexin III specific reactions, 2 to 8 ng cDNA for Brca1- and 2C11B-specific reactions), no template controls; 'M', molecular size markers. The integrated intensity of the band corresponding in size to the expected amplimer was determined using ImageQuant software (Molecular Dynamics). For genetag concentrations in the linear range, the fluorescence intensity of the expected product increased exponentially with cycle number from 24–28 cycles.

To verify that the products were indeed those expected, the 291 bp Brca1 amplimer was gel-purified and sequenced in both directions with the same primers used in the initial reaction. The experimentally determined sequence exactly matched the predicted sequence. To further validate the specificity of COP reactions, primers were selected for 9 other genes that varied widely in their expected expression levels and in the lengths of the predicted amplimers. Reaction products of the expected size were again gel-purified and sequenced. All 10 of the amplimers analyzed gave greater than 95% sequence identity to the expected product. These included the gene-specific targets of several high abundance, housekeeping genes, including ribosomal protein L5 and γ-actin, and also lower abundance genes, including transcription factors YY-1 and Genesis.

To detect changes in gene expression due to overexpression of E2F1, paired reactions were performed with genetag preparations derived from wild type or K5 E2F1 transgenic keratinocytes. Mice transgenic for the human E2F-1 gene under the control of the bovine keratin 5 promoter were maintained as heterozygotes. Epidermal keratinocyte cultures were derived from newborn mice carrying the transgene or from their wild type siblings as described. Total RNA was prepared by extraction into a chaotropic salt solution followed by organic solvent extraction using either a QIAGEN (Valencia, Calif.) or a GIBCO/BRL (Gaithersburg, Md.) kit. Total RNA was used directly for Northern analyses. Alternatively, mRNA was prepared using a QIAGEN kit, and double-stranded cDNA was synthesized using biotinylated p(dT)$_{18}$ as the primer for first strand synthesis. The relative concentrations of wild type and transgenic genetags were adjusted to give approximately equal expression ratios for a set of control genes (ribosomal proteins L5 and S17, GAPDH, β-actin and γ-actin) whose expression was not expected to change significantly with E2F1 overexpression. In all, the inventors performed reactions for over 400 known murine genes, including genes previously shown to be regulated by E2F1 and other genes related to cell proliferation, apoptosis, transcriptional regulation and signal transduction. The inventors were able to detect the expected amplimers in reactions with 223 pairs of primers. The remaining genes may not be expressed in keratinocytes, or their expression levels may be below the detection limit of the COP technique. The amplimers produced by COP primers for several representative genes are shown in FIG. 15.

Eight genes previously shown to be transcriptionally regulated by E2F, Pierce et al., 1998a; Johnson ad Schneider-Broussard, 1998; Slansky and Famnham, 1996; Bates et al., 1998, were analyzed first. Replicate, paired analyses for 2 of these E2F1-inducible genes, cyclin E and cdc2, as well as analyses of a control gene, β-actin, are shown in FIG. 16. While production of the β-actin-specific amplimer was identical with the wild-type and transgenic templates, the cdc2-specific amplimer was about 2-fold more abundant in transgenic keratinocytes and the cyclin E-specific amplimer was increased about 5-fold. The 5-fold increase in expression of cyclin E seen here agrees well with a previous determination by Northern hybridization, Pierce et al., 1998a, (~6-fold). Recent studies have shown an upregulation of the ARF mRNA product of the Cdkn2a locus by E2F1 overexpression, and implicated this induction in E2F1-induced, p53-mediated apoptosis, Bates et al., 1998; Zindy et al., 1998; deStanchina et al., 1998. COP analyses indicated at least a 3-fold induction of Cdkn2a/p19$^{ARF}$ in the transgenic keratinocytes (FIG. 15, lane 7; Table 8). In all, six of the eight known E2F1-target genes exhibited 2–5-fold increases in steady-state expression in E2F1 transgenic keratinocytes (Table 8), while two more targets changed less than 2-fold. In addition, several other cell-cycle related genes, including Ccnb2, the cyclin activating kinase Cdk7 and Odc were upregulated 3–6-fold in the transgenic keratinocytes. Increased expression of the genes for several transcription factors (Hfh2 & Yy1) and the Brca1 tumor suppressor gene, genes not known to be E2F1-regulated, was also seen; several of these are illustrated in FIG. 15. The Brca1 gene has been shown to be cell cycle regulated, Vaughn et al., 1996; Gudas et al., 1996, and potential E2F sites are present in the Brca1 promoter. Evidence for cell cycle regulation of Cdk7 expression in fibroblasts has recently been presented, Iyer et al., 1999. Three of the known downstream targets for p53 transactivation, cyclin G, Bax-α and MDM2 (Levine, 1997), were also expressed at higher levels (2–4-fold increased) in E2F1 transgenic keratinocytes (Table 8). A fourth target of p53, p21, was unchanged in the transgenic cells and GADD45 was among the 10% of the genome that could not be assayed.

To confirm the magnitude of changes in expression seen with the COP technique, we compared the expression of several selected genes between wild-type and transgenic keratinocytes by Northern analyses. While the expression of Actg, the gene for g-actin, was approximately equal in wild type and transgenic keratinocytes, the genes for Cdc2 and Cdkn2a/p19ARF were upregulated by E2F1 overexpression (FIG. 17A), in good agreement with the COP results (FIG. 15 and FIG. 16, Table 8). Expression ratios were determined for 9 genes by both COP and Northern analyses, and the ratios were plotted as a scattergram (FIG. 17B). The data were well-fit by a straight line with slope close to 1.0, indicating a high degree of concordance between the two techniques.

TABLE 8

DETERMINATION OF GENE EXPRESSION CHANGES BY COP
The expression ratio is calculated as the band intensity seen with the transgenic template divided by the intensity seen with a paired reaction using wild type template. The statistical significance of alterations in this ratio for each gene in the first two groups compared to the expression ratio seen for the control genes was evaluated using unpaired t-tests. The differences were significant at the p <0.01 level for all genes listed with the exception of Ccna.

| E2F Target Genes | | Other Genes | | p53 Target Genes | | Control Genes | |
|---|---|---|---|---|---|---|---|
| Gene | Expression Ratio | Gene | Expression Ratio | Gene | Expression Ratio | Gene | Expression Ratio |
| Ccne | 5.1 ± 1.0 | Ccnb2 | 6.4 ± 4.1 | Ccng | 2.3 ± 0.5 | Actb | 1.1 ± 0.2 |
| Cdkn2a | 2.7 ± 0.6 | Hfh2 | 4.9 ± 3.3 | Bax | 2.0 ± 0.7 | Rps17 | 1.1 ± 0.1 |
| Tk1 | 2.6 ± 1.2 | Vegf | 3.7 ± 1.7 | Mdm2 | 2.0 ± 0.2 | Gapd | 1.0 ± 0.1 |
| Pola1 | 2.4 ± 0.4 | Odc | 3.6 ± 1.0 | Cdkn1a | 1.4 ± 0.2 | Hmg14 | 0.9 ± 0.1 |
| Cdc2 | 2.4 ± 0.9 | Yy1 | 3.1 ± 1.8 | | | Lmna | 1.1 ± 0.2 |
| Myb12 | 2.1 ± 0.2 | Cdk7 | 3.1 ± 0.3 | | | Actg | 1.1 ± 0.2 |
| Myc | 1.4 ± 0.2 | Brca1 | 2.6 ± 1.0 | | | Rp15 | 1.0 ± 0.2 |
| Ccna2 | 1.1 ± 0.1 | Casp7 | 2.4 ± 1.5 | | | | |
| | | Casp8 | 2.1 ± 0.3 | | | | |

COP analyses can also be conducted using tissue samples from experimental animals. To prepare mouse epidermal RNA, adult mice were sacrificed and dorsal skin was dissected, heated to 55° C. in DEPC-treated H2O for 30 s, and cooled to 40° C. for 30 s. Skin samples were placed epidermal side down in 5 ml Trizol (GIBCO/BRL) for 30 s, and the epidermal layer was then scraped into the Trizol with the edge of a glass microscope slide. RNA extraction proceeded as described above. RNA was prepared from the epidermis of wild type and E2F1 transgenic mice, and either used in Northern analyses or to prepare genetags for COP analysis. As shown in FIG. 18A and FIG. 18B, COP analysis indicated a dramatic upregulation of expression of several genes, including Odc, Ccng, and Cdkn2a/p19ARF, due to overexpression of the E2F1 transgene, in both newborn keratinocytes and adult epidermis. The increase in Cdkn2a/p19ARF was particularly striking, and this induction was confirmed by Northern analyses (FIG. 18C).

The expected effects of CDK7, Brca1 and p19$^{ARF}$ on p53 are indicated in the model of FIG. 19. Each has the potential to increase p53 activity by an independent post-translational mechanism, and therefore indicating that they may cooperate in p53 upregulation. Indeed, three downstream targets of p53, cyclin G, Bax-α and Mdm-2, are all modestly unregulated in the transgenic keratinocytes, while a fourth target-gene involved in growth arrest, p21, is unaffected. This indicates that not only is p53 activity increased, but it is increased in a differential manner, with some downstream targets induced more than others. Several p53 mutants are known in which the effect of p53 on apoptosis and growth arrest are uncoupled, Ludwig et al., 1996; Rowan et al. 1996; Friedlander et al., 1996; Aurelio et al., 1998, providing a precedent for the possibility of differential regulation.

Overexpression of E2F1 in mouse fibroblasts leads to p19$^{ARF}$ mediated apoptosis, Zindy et al., 1998; deStanchina et al., 1998; Bates et al., 1998, and Brca1 overexpression has also been linked to p53-dependent apoptosis, Zhang et al., 1998; Shao et al., 1996. The E2F1-mediated transcriptional effects on genes that modulate p53 activity and on downstream targets of p53 may be manifested as an increased propensity of the transgenic keratinocytes to enter apoptosis in response to other stimuli. This is consistent with the finding of areas of increased apoptosis in the epidermis of the transgenic mice, and the fact that apoptosis is reduced in a p53 null backgrounds, Pierce et al., 1998. Interestingly, while K5 E2F1/p53 null mice have an increased incidence of spontaneous skin tumors, the single transgenics are resistant to chemical carcinogenesis in the skin (Johnson et al., in preparation). It will be of interest to determine whether cells "initiated" by a chemical carcinogen in K5 E2F1 mice are more susceptible to elimination by apoptosis than their wild type counterparts.

Example 3
Gene Discovery by COP

As noted above, each COP reaction has the potential to amplify several genes, and many non-targeted amplimer bands were noted in the course of these studies (see for example reaction 7 in FIG. 15). Five non-targeted amplimer bands that exhibited changes in expression greater than three-fold in transgenic keratinocytes were identified (Table 9), and these amplimers were sequenced Two amplimer sequences matched several ESTs, exemplified by AA245406 for EIG-1 and AV076207 for EIG-5. Subsequent to sequencing of EIG-2, an apoptosis-related gene, AIP1 (Vito et al., 1999) was described (AF1 19955) that contains a sequence 99% identical to EIG-2. EIG-3 and -4 had no matches in GenBank.

TABLE 9

EXPRESSION CHANGES IN NON-TARGET GENES

| Gene | COP Primers | Amplimer Length | Expression Ratio | Database Match |
|---|---|---|---|---|
| EIG-1 | CATGGGG_/GATCCAG | 147 | 3.6 | EST AA24506 |
| EIG-2 | CATGCGCA/GATCTGA | 167 | 18.1 | AJ005073 (partial match) |
| EIG-3 | CATGCTTT/GATCCTG | 95 | 3.6 | No match |
| EIG-4 | CATGGCCA/GATCTTC | 157 | 6.1 | No match |
| EIG-5 | CATGATTT/GATCAGC | 132 | ~3 | EST AV076207 |

Example 4
Differential Gene Expression After Carcinogen Treatment

Previous studies have shown that several important transcription factors, including Sp1, E2F1 and E2F4, bind in vitro with high affinity to DNA that has been damaged by the carcinogen BPDE (Butler, 1997; Johnson, 1997; MacLeod, 1995; MacLeod, 1996; MacLeod, 1996). The data suggest that many transcription factors may behave similarly and that this may cause disruption of normal mechanisms that regulate gene expression shortly after carcinogen treatment. Indeed, disruption of Sp1 dependent transcription by BPDE-amaged DNA has been directly demonstrated in cell cultures transfected with damaged DNA (Butler, 1997). Very little is known about changes in gene expression that follow treatment of cells with BPDE. COP analysis has therefore been applied to an experimental system derived from normal human mammary tissue.

Cultures of the HME87 line of normal human mammary epithelial cells were treated for 30 min with the ultimate carcinogen BPDE (±7r,8t-dihydroxy-9,10t-epoxy-7,8,9,10-tetrahydro-benzof[a]pyrene, ChemSyn Laboratories, Lenexa, Kans.) in MEBM (Clonetics, San Diego, Calif.); the carcinogen was dissolved in tetrahydrofuran and the final concentration of tetrahydrofuran in the medium was 0.3%. Control cultures were treated with tetrahydrofuran only. The treatment with BPDE is not demonstrably toxic for at least 48 h, but induces a high level of DNA damage in the treated cells. After treatment, the cells were returned to growth medium (MEGM) and held under normal growth conditions (37° C., 1.7% CO2) for 4, 10 or 24 h before harvesting RNA. Preparation of mRNA, cDNA and genetags proceeded as described for SKBR3 cells. For each gene of interest, duplicate, paired PCR™ reactions were performed with appropriate primers and genetags from either control or BPDE-treated cultures. For selected genes, a total of at least 4 determinations were made since power calculations give this as the minimum number of determinations needed to reliably detect 2-fold differences in expression.

A total of over 450 genes have been analyzed at one or more time points in this system. The majority of the genes analyzed showed no significant changes in expression. Data for several control genes that were not expected to change (genes for ribosomal proteins, structural proteins, housekeeping enzymes) are given in Table 10. In addition, several transcription factors were assayed that did not demonstrate BPDE-related changes (Table 10 CEBPE, c-myc, BTF3, SL1, p53). Although p53 activity often increases in response to DNA damage, this is normally post-transcriptionally modulated and changes in the expression of the p53 gene are not expected.

TABLE 10

UNCHANGED GENE EXPRESSION AFTER CARCINOGEN TREATMENT

| Gene | E/C 4 h | E/C 10 h | E/C 24 h |
|---|---|---|---|
| RPS27 | 0.9 ± 0.3 | 1.2 ± 0.4 | 0.9 ± 0.2 |
| RPS15a | 1.0 ± 0.3 | 1.4 ± 0.6 | 1.2 ± 0.3 |
| RPS7 | 1.1 ± 0.2 | 1.4 ± 0.5 | 1.7 ± 0.8 |
| RPL35 | 1.2 ± 0.3 | 1.1 ± 0.4 | 1.2 ± 0.6 |
| RPS26 | 1.2 ± 0.3 | 1.3 ± 0.5 | 1.5 ± 0.6 |
| RPS29 | 1.1 ± 0.2 | 1.3 ± 0.6 | 1.7 ± 1.2 |
| RPP1 | 1.4 ± 0.1 | 1.0 ± 0.4 | 1.7 ± 1.0 |
| RPS16 | — | 0.8 ± 0.1 | 0.9 ± 0.2 |
| RPL23a | 0.6 ± 0.1 | 1.1 ± 0.3 | 1.0 ± 0.2 |
| RPL30 | 0.8 ± 0.1 | 1.0 ± 0.1 | 1.0 ± 0.2 |
| ACTB | 1.1 ± 0.2 | 0.9 ± 0.2 | 1.3 ± 0.4 |
| LMNA | 0.7 ± 0.2 | 1.1 ± 0.3 | 0.9 ± 0.3 |
| PGK | — | 1.0 ± 0.2 | 1.1 ± 0.2 |
| IMPD | — | — | 0.8 ± 0.2 |
| CEBPE | 0.9 ± 0.3 | — | 1.0 ± 0.3 |
| MYC | — | — | 1.2 ± 0.5 |
| BTF3 | — | 1.0 ± 0.2 | 0.9 ± 0.2 |
| NFKB | — | — | 1.5 ± 0.4 |
| SL1 | — | — | 1.0 ± 0.3 |
| TP53 | 1.1 ± 0.4 | 0.9 ± 0.1 | 0.8 ± 0.3 |

TABLE 11

GENE EXPRESSION CHANGES AFTER CARCINOGEN TREATMENT

| Gene | E/C 4 h | E/C 10 h | E/C 24 h |
|---|---|---|---|
| ATF3 | 7.8 ± 4.0 | 9.2 ± 3.9 | 2.4 ± 0.7 |
| p21 | 1.0 ± 0.1 | 1.1 ± 0.2 | 2.3 ± 0.7 |

TABLE 11-continued

GENE EXPRESSION CHANGES AFTER CARCINOGEN TREATMENT

| Gene | E/C 4 h | E/C 10 h | E/C 24 h |
|---|---|---|---|
| GADD45 | 2.1 ± 0.7 | 1.9 ± 0.7 | 0.8 ± 0.4 |
| Beclin | 2.1 ± 1.4 | 2.0 ± 1.1 | — |

Data for several genes whose expression did change at one or more time points is listed in Table 11 with two prominent examples shown in FIG. 20. The most dramatic change was in the expression of the transcription factor ATF3, which increased 8–9 fold at 4 and 10 h, then dropped to a 2.4-fold increase at 24 h. Changes in ATF3 expression in response to damage induced by BPDE or related compounds have not previously been described, and it will be very interesting to determine both the mechanism and the consequences of this induction. The p21/WAF1 gene, a downstream target of p53, is a mediator of G1 arrest in response to DNA damage (Levine, 1997). Interestingly, it is not induced at early times after BPDE treatment, but does increase about 2-fold at 24 h. Parallel measurements of cell cycle parameters in these cells have indicated that there is no G1 arrest at 4 and 10 h after BPDE treatment, but there does appear to be a G1 arrest by 24 h. The genes for several other interesting proteins, a transcription factor CP2, and a protein related to apoptosis (beclin), are also upregulated at one or more time points. Thus, the COP analyses performed in this system have given a variety of clues concerning mechanisms operative in cells soon after BPDE treatment.

The COP technique has proven to be of great utility in these studies. It provides expression information on selected genes that is reliable and semi-quantitative. The technique can be performed at a relatively low cost and with a high degree of flexibility. Simultaneously, information on non-targeted genes is obtained giving the possibility of identifying novel genes whose expression changes in the system being analyzed. By sequencing the novel amplifier enough information is generally obtained (the average gene specific target length is about 128 bp) to design primers that allow the entire cDNA to be obtained. The sets of genes target for analysis can easily be altered based on the results of initial studies with multiple time points or dose regimens. Indeed, COP may have utility as a complement to SAGE or microarray methods. Initial screens by these techniques can provide a focused set of genes that can then be studied in detail by COP in a cost-effective manner. The set of reagents that must be maintained for COP analyses (256 A-end primers and 64 B-end primers) is fairly small, can be generated easily by synthetic methods, and is the same for all species. This contrasts with microarray technologies where much larger sets of clones must be maintained, or even larger sets of oligonucleotides must be designed and tested, and where each set of reagents is species-specific. The inventors are currently working on ways to speed up the analyses of the amplimers, possibly allowing COP to be performed in a high-throughput mode in which the entire transcriptome could be analyzed in a short period of time.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams et al., *Nat Genet*, 4:373–80, 1993
Alwine et al., *Proc Nati Acad Sci U S A.*, 74:5350–4, 1977.
Ardrey, Electrospray Mass Spectrometry, Spectroscopy Europe, 4, 10–18 (1992).
Aurelio et al., *Cancer Res.*, 58:2190–5, 1998.
Bates et al., *Nature*, 395:124–125, 1998.
Bauer et al., Nucleic Acids Res., 21:4272–80, 1993
Berkenkamp et al., *Science*, 281:260–2, 1998
Bertioli et al., *Nucleic Acids Res.*, 23:4520–3, 1995
Butler et al., *Carcinogenesis* 18, 239–244, 1997.
Crain, *Mass Spectrometry Reviews*, 9: 505–554, 1990.
DE43 17414
DeRisi, et al., *Nature Genetics*, 14:457–460, 1996.
deStanchina et al., *Genes Dev.*, 12:2434–2442, 1998.
Effenhauser, et al *Anal. Chem.*, 66:2949–2953, 1994.
Effenhauser, et al. *Anal. Chem.*, 65:2637–2642, 1993.
EP No. 320,308
EP No. 329,822
Fenn et al., *J. Phys. Chem.* 88, 4451–59
Fodor et al., *Nature*, 364:555–556, 1993.
Forster, 1948. *Ann. Phys.* 2, 55–75
Friedlander, et al., *Mol Cell Biol.* 16:4961–71, 1996.
Freifelder, *Physical Biochemistry Applications to Biochemistry and Molecular Biology*, 2nd ed. Wm. Freeman and Co., New York, N.Y., 1982.
Frohman, In: *PCR Protocols: A Guide To Methods And Applications*, Academic Press, N.Y., 1990.
Gazdar, et al., *Int. J. Cancer*, 78:766–74, 1998.
GB 2,202,328
Gudas et al., *Cell Growth Differ.*, 7:717–723, 1996.
Habu, et al., *Biochem Biophys Res Commun.* 234(2):516–21, 1997.
Hacia, et al., *Nature Genet.*, 14:441–449, 1996.
Harrison et al., *Science*, 261:895–897, 1993.
Hedrick et al., *Nature*, 308:153–8 1984.
Higuchi, et al., *Biotechnology* 10:413–417 1992
Hillenkamp et al. "Matrix Assisted UV-Laser Desorption/Ionization: A New Approach to Mass Spectrometry of Large Biomolecules," in Biological Mass Spectrometry eds. Burlingame and McCloskey, Elsevier Science Publishers, Amsterdam, pp. 49–60, 1990.
Holmstrom, K. et al., *Anal. Biochem.* 209:278–283 (1993)).
Hsieh et al., *Genes Dev.*, 11:1840–1852, 1997.
Ito et al., *FEBS Lett*, 351:231–6, 1994.
Iyer et al., *Science*, 283:83–87, 1999.
Jacobson, et al., *Anal. Chem.*, 66:1107–1113, 1994
Johnson, et al., *Frontiers in Bioscience*, 3:447–458, 1998.
Johnson et al., *Carcinogenesis* 20, 216–223, 1997
J.P. No. 59-131909
Kamijo et al., *Proc. Nat'l Acad. Sci. USA*, 95:8292–8297, 1998.
Koster et al. *Biomedical Environmental Mass Spectrometry* 14: 111–116 (1987).

Kwoh et al., *Proc. Nat. Acad Sci. USA*, 86: 1173, 1989
Lee, et al., 1993. *Nuc. Acids Res.* 21, 3761–3766
Levine, *Cell*, 88:323–331, 1997.
Liang and Pardee, *Science*, 257:967–71, 1992.
Liang et al., *Nucleic Acids Res* 21:3269–75, 1993.
Lockhart, et al. *Nature Biotech.*, 14:1675–1680, 1996.
Lu, et al., *Mol. Cell. Biol.*, 17:5923–5934, 1997.
Ludwig et al., *Mol Cell Biol.*, 16(9):4952–60, 1996.
Manz, et al., *J. Chromatogr.*, 593:253–258, 1992.
MacLeod et al., *Carcinogenesis* 16, 975–983, 1995.
MacLeod Mol. *Carcinogenesis* 15, 241–250, 1996.
MacLeod et al., *Mol. Carcinogenesis* 16, 44–52, 1996
Methods in Enzymology, Vol. 193: "Mass Spectrometry" (J. A. McCloskey, editor), 1990, Academic Press, New York.
Newton, et al. *Nucl. Acids Res.* 21:1155–1162 (1993).
Ohara et al., *Proc. Nat'l Acad. Sci. USA*, 86:5673–5677, 1989.
Okubo et al., *Nat Genet.*, 2: 173–9. 1992.
Ouchi, et al., *Proc. Nat'l Acad. Sci. USA*, 95:2302–2306, 1998.
PCT/US87/00880
PCT/US89/01025
Pease et al., *Proc. Natl. Acad. Sci. USA*, 91:5022–5026, 1994.
Phillips, et al., *Genes Dev.*, 11:1853–1863, 1997.
Pierce, et al., *Proc. Nat'l Acad. Sci. USA*, 95:8858–8863, 1998b.
Pierce, et al, *Oncogene*, 16:1267–1276, 1998a.
Pomerantz, et al., *Cell*, 92:713–723, 1998.
Putney et al., *Nature*, 302: 718–21. 1983.
Rasmussen, et al., *Anal. Biochem*, 198:138–142, 1991.
Rowan et al. *EMBO J.*, 15:827–38, 1996.
Running. J. A. et al., *BioTechniques* 8:276–277, 1990.
Sambrook et al., "Molecular Cloning," *A Laboratory Manual*, 2d Ed., Cold Spring Harbor Laboratory Press, New York, 13.7–13.9:1989.
Schena, et al., *Science*, 270:467470, 1995.
Schram, *Methods Biochem Anal.*, 34: 203–287 1990.
Shimkets et al., *Nat Biotechnol.* 17:798–803, 1999.
Shoemaker et al., *Nature Genetics* 14:450–456, 1996.
Slansky and Famnham, *In: Current Topics in Microbiology and Immunology, Transcriptional Control of Cell Growth: The E2F Gene Family*, P. Farnham (ed.), Springer-Verlag, Berlin, 208:1–30, 1996.
Smith et al., *Anal. Chem.* 62, 882–89, 1990.
Song and Osborn, *Plant Mol Biol.* 26:1065–71. 1994.
Stone and Wharton, *Nucleic Acids Res.*, 22:2612–8, 1994.
Tsuda et al., *Anal. Chem.*, 62:2149–2152, 1990.
U.S. Pat. No. 5,904,824
U.S. Pat. No. 5,856,174
U.S. Pat. No. 5,866,330
U.S. Pat. No. 5,843,651.
U.S. Pat. No. 5,610,287
U.S. Pat. No. 5,599,668
U.S. Pat. No. 5,424,186
U.S. Pat. Nos. 5,304,487
U.S. Pat. Nos. 5,296,375
U.S. Pat. Nos. 5,143,854
U.S. Pat. Nos. 4,683,194
U.S. Pat. No. 4,683,195,
U.S. Pat. No. 4,683,202
U.S. Pat. No. 4,800,159
U.S. Pat. No. 4,883,750
Vaughn et al., *Cell Growth Differ.*, 7:711–715, 1996.
Velculescu, et al., *Science*, 270:484–487, 1995.
Velculescu, et al, *Cell*, 88:243–251, 1997.
Veres, et al. *Science* 1987 July 24;237(4813):415–7, 1987
Vito, et al., *Science*, 271:521–525, 1996.
Vito, et al., *J. Biol. Chem.*, 274:1533–40, 1999.
Wang and Feuerstein, Biotechniques, 18:448–53, 1995.
Williams et al., *Science*, 246: 1585–87, 1989
Woolley and Mathies, *Proc Natl Acad Sci USA*, 91:11348–52, 1994
WO 94/05414
WO 93/18176
WO 90/14148
WO 90/07641
WO 89/06700
WO 88/10315
Wu et al., *Genomics*, 4:560–569; 1989.
Ying, et al, *BioTechniques*, 27:410–414; 1999.
Zhang et al., *Oncogene*, 16:1713–1721,1998.
Zhang, et al., *Science*, 276:1268–1272, 1997.
Zhang, et al., *Cell*, 92:725–734, 1998a
Zindy et al., *Genes Dev.*, 12:2424–2433, 1998.
Zinn et al, *Cell*, 34(3):865–79. 1983

What is claimed is:

1. A method comprising:
   a) obtaining a DNA comprising an anchorable moiety;
   b) cleaving said DNA with a first restriction endonuclease;
   c) ligating a linker molecule to cleaved DNA produced in step b;
   d) immobilizing linker ligated DNA through said anchorable moiety;
   e) cleaving DNA immobilized in step d with a second restriction endonuclease;
   f) ligating a second linker molecule to DNA cleaved in step e;
   g) amplfying DNA ligated in step f.

2. The method of claim 1, wherein said DNA is immobilized prior to cleaving with said first endonuclease.

3. The method of claim 1, wherein said DNA is non-genomic DNA.

4. The method of claim 1, wherein said DNA is cDNA.

5. The method of claim 1, wherein said anchorable moiety comprises a means of adhering.

6. The method of claim 5, wherein said means of adhering comprises a means of establishing a non-covalent interaction.

7. The method of claim 5, wherein said means of adhering comprises a means of establishing a covalent interaction.

8. The method of claim 5, wherein said means of adhering comprises a ligand.

9. The method of claim 5, wherein said means of adhering is biotin.

10. The method of claim 5, wherein said means of adhering comprises an antibody.

11. The method of claim 1, wherein said anchorable moiety is located at the 3' end.

12. The method of claim 4, wherein said cDNA is reverse transcribed from messenger RNA.

13. The method of claim 12, wherein said reverse transcription is initiated at an oligo dT.

14. The method of claim 12, wherein said reverse transcription is initiated at a random hexamer.

15. The method of claim 13, wherein said oligo dT is biotinylated.

16. The method of claim 15 wherein said cDNA is immobilized on a substrate by means of said biotinylated oligo dT.

17. The method of claim 16, wherein said substrate is streptavidin.

18. The method of claim 1, wherein the order of said first and said second restriction endonucleases is reversed.

19. The method of claim 1, wherein said amplification is initiated at primers comprising a sequence complementary to said first and said second linkers respectively.

20. The method of claim 1, wherein amplification is carried out with a primer set comprising:
   a) a first amplification primer, wherein the 5' sequence of said primer is complementary to said first linker sequence and the 3' sequence comprises a specificity region;
   b) a second amplification primer, wherein the 5' sequence of said primer is complementary to said second linker sequence and the 3' sequence comprises a specificity region.

21. The method of claim 20, wherein said amplification is performed with an array of combinations of alternate amplification primers.

22. The method of claim 20 wherein said DNA fragment is preamplified.

23. The method of claim 1, further comprising identifying the amplified DNA.

24. The method of claim 23, wherein said identification is based upon length.

25. The method of claim 23, wherein said identification is performed by a computer program.

26. The method of claim 21, wherein said amplification is performed in a multi-well plate.

27. The method of claim 20, wherein the specificity region of the first amplification primer is 3,4,5,6,7 or 8 base pairs long.

28. The method of claim 20, wherein the specificity region of the second amplification primer is 3,4,5,6,7 or 8 base pairs long.

29. The method of claim 1, wherein said amplification comprises polymerase chain reaction, nucleic acid sequence based amplification, transcription mediated amplification, strand displacement amplification or ligase chain reaction.

30. The method of claim 1, wherein said first restriction endonuclease has a four base pair recognition site.

31. The method of claim 1, wherein said first restriction endonuclease has a recognition site of five, six, seven or eight base pairs.

32. The method of claim 30, wherein said first restriction endonuclease is NlaIII, DpnII, Sau3AI Hsp92II, MboI, NdeII, Bsp1431, Tsp509 I, HhaI, HinP1I, HpaII, MspI, TaqalphaI, MaeII or K2091.

33. The method of claim 1, wherein said second restriction endonuclease has a four base pair recognition site.

34. The method of claim 1, wherein said second restriction endonuclease has a recognition site of five, six, seven or eight base pairs.

35. The method of claim 33, wherein the restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091.

36. The method of claim 1, wherein a label is incorporated into said amplified DNA.

37. The method of claim 36, wherein said label is incorporated by means of a labeled primer.

38. The method of claim 36, further comprising partial nucleotide sequence identification of the amplified products by the identity of the label.

39. The method of claim 36, wherein said label is a chromophore.

40. The method of claim 36, wherein said label is a fluorophore.

41. The method of claim 36, wherein said label is an affinity label.

42. The method of claim 36, wherein said label is a dye.

43. The method of claim 37, wherein the 5' end of said primer comprises an amino moiety and a flurophore is covalently attached by the reaction of a succinimido ester of the flurophore to the 5' amino-modified primer.

44. The method of claim 40, wherein said fluorophore is Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, or Texas Red.

45. The method of claim 1, wherein the products of said amplification are analyzed.

46. The method of claim 45, wherein said analysis of amplification products is by polyacrylamide gel electrophoresis.

47. The method of claim 45, wherein said analysis of amplification products is by capillary gel electrophoresis.

48. The method of claim 45, wherein said analysis of amplification products is by mass spectrophotometry.

49. The method of claim 45, wherein said analysis of amplification products is by energy transfer.

50. The method of claim, 45, wherein said analysis of amplification products is by OIA technology.

51. The method of claim 45, wherein said analysis of amplification products utilizes fluorescently-labeled latex beads.

52. The method of claim 45, wherein said analysis of amplification products comprises quantifying amplification products.

53. The method of claim 52, wherein said quantifying is by measuring the ratio of each amplified product to a co-amplified reference-gene.

54. The method of claim 52, wherein said quantifying is by measuring the ratio of each amplified product to a panel of co-amplified reference-genes.

55. The method of claim 52, wherein said analysis of amplification products is by Real-Time PCR.

56. The method of claim 45, wherein said analysis of amplification products is performed in a multi-well plate.

57. The method of claim 45, wherein said analysis of amplification products is performed on a membrane.

58. The method of claim 45, wherein said analysis of amplification products is performed on a solid matrice.

59. The method of claim 58, wherein said solid matrice is a DNA chip.

60. The method of claim 1, performed on DNA derived from a normal cell or tissue and on DNA derived from a different cell or tissue.

61. The method of claim 1, performed on DNA derived from a normal cell or tissue and on DNA derived from a cancerous cell or tissue.

62. The method of claim 1, performed on DNA derived from a normal cell or tissue and on DNA derived a cell or tissue treated with a pharmaceutical compound.

63. The method of claim 1, performed on DNA derived from a normal cell or tissue and on DNA derived from a cell or tissue treated with a teratogenic compound.

64. The method of claim 1, performed on DNA derived from a normal cell or tissue and on DNA derived from a cell or tissue treated with a carcinogenic compound.

65. The method of claim 1, performed on DNA derived from a normal cell or tissue and on DNA derived from a cell or tissue treated with a toxic compound.

66. The method of claim 1, performed on DNA derived from a normal cell or tissue and on DNA derived from a cell or tissue treated with a biological response modifier.

67. The method of claim 1, performed on DNA derived from a normal cell or tissue and on DNA derived from a cell or tissue treated with a hormone, a hormone agonist or a hormone antagonist.

68. The method of claim 1, performed on DNA derived from a normal cell or tissue and on DNA derived from a cell or tissue treated with a cytokine.

69. The method of claim 1, performed on DNA derived from a normal cell or tissue and on DNA derived from a cell or tissue treated with a growth factor.

70. The method of claim 1, performed on DNA derived from a normal cell or tissue and on the DNA derived from a cell or tissue treated with the ligand of a known biological receptor.

71. The method of claim 1, performed on DNA derived from a cell or tissue type obtained from a different species.

72. The method of claim 1, performed on DNA derived from a cell or tissue type obtained from a different organism.

73. The method of claim 1, performed on DNA derived from a cell or tissue at different stages of development.

74. The method of claim 1, performed on DNA derived from a normal cell or tissue and on the DNA derived from a cell or tissue that is diseased.

75. The method of claim 1, performed on DNA derived from a cell or tissue cultured in vitro under different conditions.

76. The method of claim 1, performed on the DNA derived from a cell or tissue from two organisms of the same species with a known genetic difference.

77. A kit for detection of gene expression comprising:
a) a first restriction enzyme;
b) a second restriction enzyme;
c) a first, ligatable, oligonucleotide tag;
d) a second, ligatable, oligonucleotide tag;
e) a first amplification primer, wherein the 5' sequence of said primer is complementary to said first oligonucleotide tag and the 3' sequence comprises a specificity region;
f) a second amplification primer, wherein the 5' sequence of said primer is complementary to said second oligonucleotide tar and the 3' sequence comprises a specificity region;
g) software capable of analyzing data generated from said kit.

78. The kit of claim 77, wherein said first restriction enzyme is a four base pair cutter.

79. The kit of claim 78, wherein said first restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091.

80. The kit of claim 77, wherein said second restriction enzyme is a four base pair cutter.

81. The kit of claim 80, wherein said second restriction endonuclease is NlaII, DpnII, Sau3AI, Hsp92II, MboI, NdeII, Bsp1431, Tsp509 I, HhaI, HinP1I, HpaII, MspI, TaqalphaI, MaeII or K2091.

82. The kit of claim 77, wherein said first amplification primer comprises the sequence GCTGTCTAGACG (SEQ ID NO: 1).

83. The kit of claim 77, wherein said second amplification primer comprises the sequence CGGTGATGCATC (SEQ ID NO:2).

84. The method of claim 1, wherein said anchorable moiety is located at the 5' end.

* * * * *

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

Column 55,
Lines 25 and 26, please delete claim 2,

Column 58,
Line 66, please insert:

--84. A method comprising:
    a) obtaining a DNA comprising an anchorable moiety;
    b) immobilizing said DNA through said anchorable moiety;
    c) cleaving said DNA with a first restriction endonuclease;
    d) ligating a linker molecule to immobilized DNA produced in step c;
    e) cleaving DNA produced in step d with a second restriction endonuclease;
    f) ligating a second linker molecule to DNA cleaved in step e;
    g) amplifying DNA ligated in step f.

85. The method of claim 84, wherein said DNA is non-genomic DNA.

86. The method of claim 84, wherein said DNA is cDNA.

87. The method of claim 84, wherein said anchorable moiety comprises a means of adhering.

88. The method of claim 87, wherein said means of adhering comprises a means of establishing a non-covalent interaction.

89. The method of claim 87, wherein said means of adhering comprises a means of establishing a covalent interaction.

90. The method of claim 87, wherein said means of adhering comprises a ligand.

91. The method of claim 87, wherein said means of adhering is biotin.

92. The method of claim 87, wherein said means of adhering comprises an antibody.

93. The method of claim 84, wherein said anchorable moiety is located at the 3' end.

94. The method of claim 86, wherein said cDNA is reverse transcribed from messenger RNA.

95. The method of claim 94, wherein said reverse transcription is initiated at an oligo dT.

UNITED STATES PATENT AND TRADEMARK OFFICE
CERTIFICATE OF CORRECTION

| | |
|---|---|
| PATENT NO. : 6,221,600 B1 | |
| DATED : April 24, 2001 | |
| INVENTOR(S) : MacLeod et al. | |

It is certified that error appears in the above-identified patent and that said Letters Patent is hereby corrected as shown below:

<u>Column 58 (cont'd),</u>

96. The method of claim 94, wherein said reverse transcription is initiated at a random hexamer.

97. The method of claim 95, wherein said oligo dT is biotinylated.

98. The method of claim 97 wherein said cDNA is immobilized on a substrate by means of said biotinylated oligo dT.

99. The method of claim 98, wherein said substrate is streptavidin.

100. The method of claim 84, wherein the order of said first and said second restriction endonucleases is reversed.

108. The method of claim 103, wherein said amplification is performed in a multi-well plate.

109. The method of claim 102, wherein the specificity region of the first amplification primer set is 3,4,5,6,7 or 8 base pairs long.

110. The method of claim 102, wherein the specificity region of the second amplification primer set is 3,4,5,6,7 or 8 base pairs long.

111. The method of claim 84, wherein said amplification comprises polymerase chain reaction, nucleic acid sequence based amplification, transcription mediated amplification, strand displacement amplification or ligase chain reaction.

112. The method of claim 84, wherein said first restriction endonuclease has a four base pair recognition site.
113. The method of claim 84, wherein said first restriction endonuclease has a recognition site of five, six, seven or eight base pairs.

114. The method of claim 112, wherein said first restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091.

115. The method of claim 84, wherein said second restriction endonuclease has a four base pair recognition site.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

<u>Column 58 (cont'd),</u>

116. The method of claim 84, wherein said second restriction endonuclease has a recognition site of five, six, seven or eight base pairs.

117. The method of claim 115, wherein the restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091.

118. The method of claim 84, wherein a label is incorporated into said amplified DNA.

119. The method of claim 118, wherein said label is incorporated by means of a labeled primer.

120. The method of claim 118, further comprising partial nucleotide sequence identification of the amplified products by the identity of the label.

121. The method of claim 118, wherein said label is a chromophore.

122. The method of claim 118, wherein said label is a fluorophore.

123. The method of claim 118, wherein said label is an affinity label.

124. The method of claim 118, wherein said label is a dye.

125. The method of claim 119, wherein the 5' end of said primer comprises an amino moiety and a flurophore is covalently attached by the reaction of a succinimido ester of the flurophore to the 5' amino-modified primer.

126. The method of claim 122, wherein said fluorophore is Alexa 350, Alexa 430, AMCA, BODIPY 630/650, BODIPY 650/665, BODIPY-FL, BODIPY-R6G, BODIPY TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, or Texas Red.

127. The method of claim 84, wherein the products of said amplification are analyzed.

128. The method of claim 127, wherein said analysis of amplification products is by polyacrylamide gel electrophoresis.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

Column 58 (cont'd),

129. The method of claim 127, wherein said analysis of amplification products is by capillary gel electrophoresis.

130. The method of claim 127, wherein said analysis of amplification products is by mass spectrophotometry.

131. The method of claim 127, wherein said analysis of amplification products is by energy transfer.

132. The method of claim 127, wherein said analysis of amplification products is by OIA technology.

133. The method of claim 127, wherein said analysis of amplification products utilizes fluorescently-labeled latex beads.

134. The method of claim 127, wherein said analysis of amplification products comprises quantifying amplification products.

135. The method of claim 134, wherein said quantifying is by measuring the ratio of each amplified product to a co-amplified reference-gene.

136. The method of claim 134, wherein said quantifying is by measuring the ratio of each amplified product to a panel of co-amplified reference-genes.

137. The method of claim 134, wherein said analysis of amplification products is by Real-Time PCR.

138. The method of claim 127, wherein said analysis of amplification products is performed in a multi-well plate.

139. The method of claim 127, wherein said analysis of amplification products is performed on a membrane.

140. The method of claim 127, wherein said analysis of amplification products is performed on a solid matrice.

141. The method of claim 140, wherein said solid matrice is a DNA chip.

142. The method of claim 84, performed on DNA derived from a normal cell or tissue and on DNA derived from a different cell or tissue.

143. The method of claim 84, performed on DNA derived from a normal cell or tissue and on DNA derived from a cancerous cell or tissue.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

Column 58 (cont'd),

144. The method of claim 84, performed on DNA derived from a normal cell or tissue and on DNA derived from a cell or tissue treated with a pharmaceutical compound.

145. The method of claim 84, performed on DNA derived from a normal cell or tissue and on DNA derived from a cell or tissue treated with a teratogenic compound.

146. The method of claim 84, performed on DNA derived from a normal cell or tissue and on DNA derived from a cell or tissue treated with a carcinogenic compound.

147. The method of claim 84, performed on DNA derived from a normal cell or tissue and on DNA derived from a cell or tissue treated with a toxic compound.

148. The method of claim 84, performed on DNA derived from a normal cell or tissue and on DNA derived from a cell or tissue treated with a biological response modifier.

149. The method of claim 84, performed on DNA derived from a normal cell or tissue and on DNA derived from a cell or tissue treated with a hormone, a hormone agonist or a hormone antagonist.

150. The method of claim 84, performed on DNA derived from a normal cell or tissue and on DNA derived from a cell or tissue treated with a cytokine.

151. The method of claim 84, performed on DNA derived from a normal cell or tissue and on DNA derived from a cell or tissue treated with a growth factor.

152. The method of claim 84, performed on DNA derived from a normal cell or tissue and on the DNA derived from a cell or tissue treated with the ligand of a known biological receptor.

153. The method of claim 84, performed on DNA derived from a cell or tissue type obtained from a different species.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

Column 58 (cont'd),

154. The method of claim 84, performed on DNA derived from a cell or tissue type obtained from a different organism.

155. The method of claim 84, performed on DNA derived from a cell or tissue at different stages of development.

156. The method of claim 84, performed on DNA derived from a normal cell or tissue and on the DNA derived from a cell or tissue that is diseased.

157. The method of claim 84, performed on DNA derived from a cell or tissue cultured in vitro under different conditions.

158. The method of claim 84, performed on the DNA derived from a cell or tissue from two organisms of the same species with a known genetic difference.

159. The method of claim 84, wherein said anchorable moiety is located at the 5' end.--
therefor.

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

Column 55,
Lines 25 and 26, please delete claim 2,

Column 58,
Line 66, please insert:

--84.  A method comprising:
    a) obtaining a DNA comprising an anchorable moiety;
    b) immobilizing said DNA through said anchorable moiety;
    c) cleaving said DNA with a first restriction endonuclease;
    d) ligating a linker molecule to immobilized DNA produced in step c;
    e) cleaving DNA produced in step d with a second restriction endonuclease;
    f) ligating a second linker molecule to DNA cleaved in step e;
    g) amplifying DNA ligated in step f.

85. The method of claim 84, wherein said DNA is non-genomic DNA.

86. The method of claim 84, wherein said DNA is cDNA.

87. The method of claim 84, wherein said anchorable moiety comprises a means of adhering.

88. The method of claim 87, wherein said means of adhering comprises a means of establishing a non-covalent interaction.

89. The method of claim 87, wherein said means of adhering comprises a means of establishing a covalent interaction.

90. The method of claim 87, wherein said means of adhering comprises a ligand.

91. The method of claim 87, wherein said means of adhering is biotin.

92. The method of claim 87, wherein said means of adhering comprises an antibody.

93. The method of claim 84, wherein said anchorable moiety is located at the 3' end.

94. The method of claim 86, wherein said cDNA is reverse transcribed from messenger RNA.

95. The method of claim 94, wherein said reverse transcription is initiated at an oligo dT.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

<u>Column 58 (cont'd),</u>

96.  The method of claim 94, wherein said reverse transcription is initiated at a random hexamer.

97.  The method of claim 95, wherein said oligo dT is biotinylated.

98.  The method of claim 97 wherein said cDNA is immobilized on a substrate by means of said biotinylated oligo dT.

99.  The method of claim 98, wherein said substrate is streptavidin.

100.  The method of claim 84, wherein the order of said first and said second restriction endonucleases is reversed.

101.  The method of claim 85, wherein the order of said first and said second restriction endonucleases is reversed.

102.  The method of claim 85, wherein said amplification is initiated at primers comprising a sequence complementary to said first and said second linkers respectively.

103.  The method of claim 85, wherein amplification is carried out with a primer set comprising:
    a)    a first amplification primer, wherein the 5' sequence of said primer is complementary to said first linker sequence and the 3' sequence comprises a specificity region;
    b)    a second amplification primer, wherein the 5' sequence of said primer is complementary to said second linker sequence and the 3' sequence comprises a specificity region.

104.  The method of claim 103, wherein said amplification is performed with an array of combinations of alternate amplification primers.

105.  The method of claim 103, wherein said DNA fragment is preamplified.

106.  The method of claim 85, further comprising identifying the amplified DNA.

107.  The method of claim 106, wherein said identification is based upon length.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

<u>Column 58 (cont'd),</u>

108. The method of claim 103, wherein said amplification is performed in a multi-well plate.

109. The method of claim 102, wherein the specificity region of the first amplification primer set is 3,4,5,6,7 or 8 base pairs long.

110. The method of claim 102, wherein the specificity region of the second amplification primer set is 3,4,5,6,7 or 8 base pairs long.

111. The method of claim 84, wherein said amplification comprises polymerase chain reaction, nucleic acid sequence based amplification, transcription mediated amplification, strand displacement amplification or ligase chain reaction.

112. The method of claim 84, wherein said first restriction endonuclease has a four base pair recognition site.

113. The method of claim 84, wherein said first restriction endonuclease has a recognition site of five, six, seven or eight base pairs.

114. The method of claim 112, wherein said first restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091.

115. The method of claim 84, wherein said second restriction endonuclease has a four base pair recognition site.

116. The method of claim 84, wherein said second restriction endonuclease has a recognition site of five, six, seven or eight base pairs.

117. The method of claim 115, wherein the restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091.

118. The method of claim 84, wherein a label is incorporated into said amplified DNA.

119. The method of claim 118, wherein said label is incorporated by means of a labeled primer.

120. The method of claim 118, further comprising partial nucleotide sequence identification of the amplified products by the identity of the label.

UNITED STATES PATENT AND TRADEMARK OFFICE
CERTIFICATE OF CORRECTION

| | |
|---|---|
| PATENT NO. : 6,221,600 B1 | |
| DATED : April 24, 2001 | |
| INVENTOR(S) : MacLeod et al. | |

It is certified that error appears in the above-identified patent and that said Letters Patent is hereby corrected as shown below:

<u>Column 58 (cont'd),</u>

121. The method of claim 118, wherein said label is a chromophore.

122. The method of claim 118, wherein said label is a fluorophore.

123. The method of claim 118, wherein said label is an affinity label.

124. The method of claim 118, wherein said label is a dye.

125. The method of claim 119, wherein the 5' end of said primer comprises an amino moiety and a flurophore is covalently attached by the reaction of a succinimido ester of the flurophore to the 5' amino-modified primer.

126. The method of claim 122, wherein said fluorophore is Alexa 350, Alexa 430, AMCA, BODIPY 630/650, BODIPY 650/665, BODIPY-FL, BODIPY-R6G, BODIPY TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, or Texas Red.

127. The method of claim 84, wherein the products of said amplification are analyzed.

128. The method of claim 127, wherein said analysis of amplification products is by polyacrylamide gel electrophoresis.

129. The method of claim 127, wherein said analysis of amplification products is by capillary gel electrophoresis.

130. The method of claim 127, wherein said analysis of amplification products is by mass spectrophotometry.

131. The method of claim 127, wherein said analysis of amplification products is by energy transfer.

132. The method of claim 127, wherein said analysis of amplification products is by OIA technology.

133. The method of claim 127, wherein said analysis of amplification products utilizes fluorescently-labeled latex beads.

134. The method of claim 127, wherein said analysis of amplification products comprises quantifying amplification products.

UNITED STATES PATENT AND TRADEMARK OFFICE
CERTIFICATE OF CORRECTION

PATENT NO. : 6,221,600 B1
DATED : April 24, 2001
INVENTOR(S) : MacLeod et al.

It is certified that error appears in the above-identified patent and that said Letters Patent is hereby corrected as shown below:

Column 58 (cont'd),

135. The method of claim 134, wherein said quantifying is by measuring the ratio of each amplified product to a co-amplified reference-gene.

136. The method of claim 134, wherein said quantifying is by measuring the ratio of each amplified product to a panel of co-amplified reference-genes.

137. The method of claim 134, wherein said analysis of amplification products is by Real-Time PCR.

138. The method of claim 127, wherein said analysis of amplification products is performed in a multi-well plate.

139. The method of claim 127, wherein said analysis of amplification products is performed on a membrane.

140. The method of claim 127, wherein said analysis of amplification products is performed on a solid matrice.

141. The method of claim 140, wherein said solid matrice is a DNA chip.

142. The method of claim 84, performed on DNA derived from a normal cell or tissue and on DNA derived from a different cell or tissue.

143. The method of claim 84, performed on DNA derived from a normal cell or tissue and on DNA derived from a cancerous cell or tissue.

144. The method of claim 84, performed on DNA derived from a normal cell or tissue and on DNA derived from a cell or tissue treated with a pharmaceutical compound.

145. The method of claim 84, performed on DNA derived from a normal cell or tissue and on DNA derived from a cell or tissue treated with a teratogenic compound.

146. The method of claim 84, performed on DNA derived from a normal cell or tissue and on DNA derived from a cell or tissue treated with a carcinogenic compound.

147. The method of claim 84, performed on DNA derived from a normal cell or tissue and on DNA derived from a cell or tissue treated with a toxic compound.

148. The method of claim 84, performed on DNA derived from a normal cell or tissue and on DNA derived from a cell or tissue treated with a biological response modifier.

149. The method of claim 84, performed on DNA derived from a normal cell or tissue and on DNA derived from a cell or tissue treated with a hormone, a hormone agonist or a hormone antagonist.

150. The method of claim 84, performed on DNA derived from a normal cell or tissue and on DNA derived from a cell or tissue treated with a cytokine.

UNITED STATES PATENT AND TRADEMARK OFFICE
CERTIFICATE OF CORRECTION

PATENT NO.     : 6,221,600 B1
DATED          : April 24, 2001
INVENTOR(S)    : MacLeod et al.

It is certified that error appears in the above-identified patent and that said Letters Patent is hereby corrected as shown below:

<u>Column 58 (cont'd),</u>

151. The method of claim 84, performed on DNA derived from a normal cell or tissue and on DNA derived from a cell or tissue treated with a growth factor.

152. The method of claim 84, performed on DNA derived from a normal cell or tissue and on the DNA derived from a cell or tissue treated with the ligand of a known biological receptor.

153. The method of claim 84, performed on DNA derived from a cell or tissue type obtained from a different species.

154. The method of claim 84, performed on DNA derived from a cell or tissue type obtained from a different organism.

155. The method of claim 84, performed on DNA derived from a cell or tissue at different stages of development.

156. The method of claim 84, performed on DNA derived from a normal cell or tissue and on the DNA derived from a cell or tissue that is diseased.

157. The method of claim 84, performed on DNA derived from a cell or tissue cultured in vitro under different conditions.

158. The method of claim 84, performed on the DNA derived from a cell or tissue from two organisms of the same species with a known genetic difference.

159. The method of claim 84, wherein said anchorable moiety is located at the 5' end.--
therefor.

This certificate supersedes Certificate of Correction issued September 9, 2003.

Signed and Sealed this

Seventeenth Day of February, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,221,600 B1 |
| APPLICATION NO. | : 09/414847 |
| DATED | : April 24, 2001 |
| INVENTOR(S) | : Michael C. MacLeod et al. |

It is certified that error appears in the above-identified patent and that said Letters Patent is hereby corrected as shown below:

In column 1, lines 7-9, delete
"The government may own rights in the present invention pursuant to grant number P30ES07784-01 from NIEHS and grant number CA35581-12 from National Cancer Institute." and insert
--This invention was made with government support under grant number P30ES07784-01 awarded by the National Institute of Environmental Health Sciences and grant number CA35581-12 awarded by the National Cancer Institute. The government has certain rights in the invention.-- therefor.

Signed and Sealed this

Sixteenth Day of March, 2010

David J. Kappos
*Director of the United States Patent and Trademark Office*